(12) United States Patent
Liu et al.

(10) Patent No.: US 10,618,960 B2
(45) Date of Patent: Apr. 14, 2020

(54) CHIMERIC AND HUMANIZED ANTI-HUMAN CTLA4 MONOCLONAL ANTIBODIES AND USES THEREOF

(71) Applicants: ONCOIMMUNE, INC., Rockville, MD (US); Yang Liu, Washington, DC (US); Pan Zheng, Washington, DC (US); Martin Devenport, Gaithersburg, MD (US)

(72) Inventors: Yang Liu, Washington, DC (US); Pan Zheng, Washington, DC (US); Martin Devenport, Gaithersburg, MD (US)

(73) Assignee: ONCOIMMUNE, INC., Rockville, MD (US)

( * ) Notice: Subject to any disclaimer, the term of this patent is extended or adjusted under 35 U.S.C. 154(b) by 117 days.

(21) Appl. No.: 16/062,350

(22) PCT Filed: Dec. 14, 2016

(86) PCT No.: PCT/US2016/066698
§ 371 (c)(1),
(2) Date: Jun. 14, 2018

(87) PCT Pub. No.: WO2017/106372
PCT Pub. Date: Jun. 22, 2017

(65) Prior Publication Data
US 2019/0127468 A1    May 2, 2019

Related U.S. Application Data

(60) Provisional application No. 62/359,036, filed on Jul. 6, 2016, provisional application No. 62/309,169, filed on Mar. 16, 2016, provisional application No. 62/267,735, filed on Dec. 15, 2015.

(51) Int. Cl.
| | |
|---|---|
| C07K 16/28 | (2006.01) |
| A61K 39/395 | (2006.01) |
| A61K 39/00 | (2006.01) |
| A61P 35/00 | (2006.01) |

(52) U.S. Cl.
CPC .......... *C07K 16/2818* (2013.01); *A61K 39/00* (2013.01); *A61P 35/00* (2018.01); *C07K 16/2878* (2013.01); *A61K 2039/505* (2013.01); *A61K 2039/507* (2013.01); *A61K 2039/575* (2013.01); *C07K 2317/24* (2013.01); *C07K 2317/34* (2013.01); *C07K 2317/52* (2013.01); *C07K 2317/72* (2013.01); *C07K 2317/732* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 7,923,221 B1 | 4/2011 | Cabilly et al. |
| 2006/0228299 A1 | 10/2006 | Thorpe et al. |
| 2013/0136749 A1 | 5/2013 | Korman et al. |

FOREIGN PATENT DOCUMENTS

| | | | |
|---|---|---|---|
| CN | 101628940 | * | 1/2010 |
| CN | 101628940 A | | 1/2010 |

OTHER PUBLICATIONS

CN 101628940 English version, published Jan. 2010.*
International Search Report of PCT/US2016/06698 dated Apr. 20, 2017.
Written Opinion of PCT/US2016/06698 dated Apr. 20, 2017.

* cited by examiner

*Primary Examiner* — Laura B Goddard
(74) *Attorney, Agent, or Firm* — Polsinelli PC; Ron Galant

(57) ABSTRACT

This invention relates to compositions of chimeric and humanized antibodies that bind to the human CTLA4 molecule and their use in cancer immunotherapy and for reduction of autoimmune side effects compared to other immunotherapeutic agents.

14 Claims, 68 Drawing Sheets

Specification includes a Sequence Listing.

A. hIg
B. L3D10 + anti-PD1
C. 10D1 + anti-PD1

A-C: Kidney
D-F: Liver

A & D: hIg
B & E: L3D10 + anti-PD1
C & F: 10D1 + anti-PD1

L3D10 VH amino acid sequence (parental)
QVQLKESGPGLVAPSQSLSITCTVSGFSLTSYGLSWVRQPPGKGLEWLGVIWYDGNTHFNSALKSRLTISKDNSKSQVFLELNSLQTDDTATYYCAKTEGHYYGSNYGYYALDYWGQGTSVTVSS Heavy Chain Framework
QVQLQESGPGLVKPSETLSLTCTVS        WIRQPPGKGLEWIG        VTISVDTSKNQFSLKLSSVTAADTAVYYCAR        WGQGTLVTVSS Humanized VH amino acid sequence 1 (HC1)
QVQLQESGPGLVKPSETLSLTCTVSGFSLTSYGLSWIRQPPGKGLEWIGYIWYDGNPNPHPSLKSRVTISKDTSKNQFSLKLSSVTAADTAVYYCARTEGHYYGSNYGYYALDYWGQGTSVTVSS Humanized VH amino acid sequence 2 (HC2)
QVQLQESGPGLVKPSETLSLTCTVSGFSITSYGLSWIRQPPGKGLEWIGYIWYDGNTNFHESLKSRVTISKDTSKSQVSLKLSSVTAADTAVYYCARTEHYYGGNYGYYALDYWGQGTLVTVSS Humanized VH amino acid sequence 3 (HC3)
QVQLQESGPGLVKPSETLSLTCTVSGFSLTSYGLSWIRQPPGKGLEWIGYIWYDGNTHFSPLKSRVTISVDTSKNQFSLKLSSVTAADTAVYYCARTEGHYYGSNYGYYALDYWGQGTLVTVSS L3D10 VL amino acid sequence (parental)
DIQMTQSPASLSVSVGETVTITCRASENIYSNLAWYQQKQGKSPQLLVYAATNLADGVPSRFSGSGSGTQYSLKINSLQSEDFGTYFCQHLWGTPYTFGGGTKLEIK Light Chain Framework
DIQMTQSPSSLSASVGDRVTITC        WYQQKPGKAPKLLIY        GVPSRFSGSGSGTDFTLTISSLQPEDFATYYC        FGQGTKLEIK Humanized VL amino acid sequence 1 (LC1)
DIQMTQSPSSLSASVGDRVTITCRASENIYSNLAWYQQKPGKAPKLLIYAATNLQSGVPSRFSGSGSGTDFTLTISSLQPEDFATYYCQHLWGTPYTFGGGTKLEIK Humanized VL amino acid sequence 2 (LC2)
DIQMTQSPSSLSASVGDRVTITCRASENIYSNLAWYQQKQGKAPKLLIYAATNLQDGVPSRFSGSGSGTDYTLTISSLQPEDFATYFCQHLWGTPYTFGQGTKLEIK Humanized VL amino acid sequence 3 (LC3)
DIQMTQSPSSLSASVGDRVTITCRASENIYSNLAWYQQKPGKAPKLLIYAATSLQSGVPSRFSGSGSGTDFTLTISSLQPEDFATYYCQHLWGTPYTFGGGTKLEIK

FIG. 38

PP4631 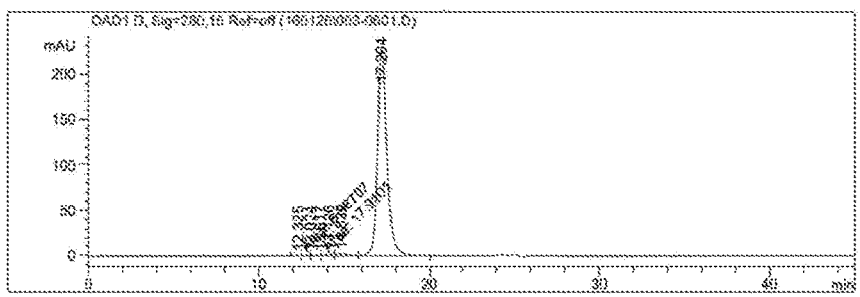
PP4637 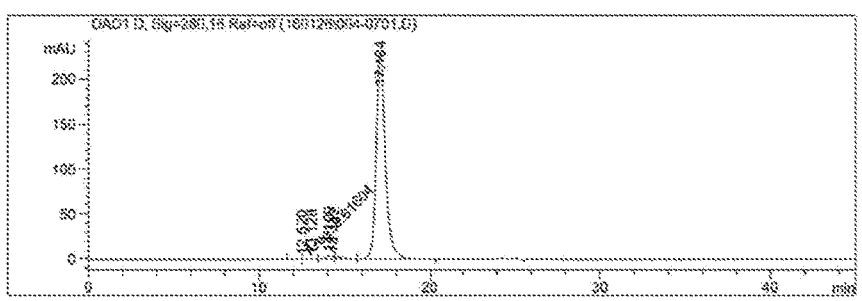
PP4638 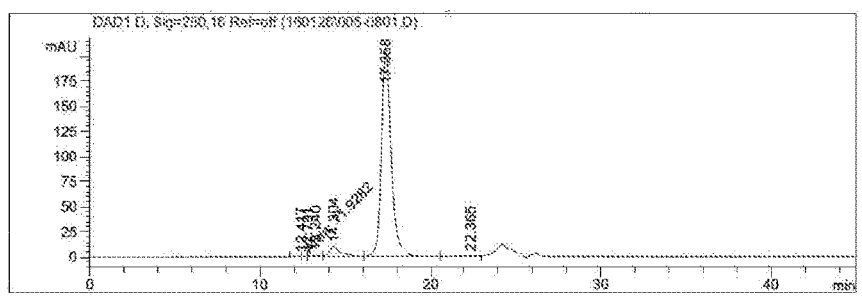
FIG. 51

```
             1.........10........20........30 ........40........50.......60
Hm       MEVAQPAVVLASSKGIASFVCEYASPGKAT EVRVTVLPQADSQVTEVCAATYMMGNELTF
Mk       -----------n-----------&------ ------------------------------
Ms       lqp-t---s----------hv---p--- ---sha-&------------tad-m------t-ftsk-tvg- Mut         M1           M2           M3              M4       M6   M5

.........70........80........90........100.......110.......120
Hm       LDDSICTGTSSGNQVNLTIQGLRAMDTGLYICKVELMYPPPYYLGIGNGTQIYVIDPEPC
Mk       -------------------------------------------m----------------
Ms       ---ypf-s---faes-------------v------l----------&Y-m----------

Mut          M7      M8            M9   M10        M11

...124
Hm       PDSD
Mk       ----
Ms       ----
```

FIG. 55

CTLA-4Fc WT

AMHVAQPAVVLASSRGIASFVCEYASPGKATEVRVTVLRQADSQVTEVCAATYMMGNELTFLDDSICTGTSSGNQVNLTIQGLRAMDTGLYICKVELMYPPPYYLGIGNGTQIYVIDPEPCP
DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M1 iqvtqPsVVLASSRGIASFVCEYASPGKATEVRVTVLRQADSQVTEVCAATYMMGNELTFLDDSICTGTSSGNQVNLTIQGLRAMDTGLYICKVELMYPPPYYLGIGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK CTLA-4Fc M2

AMHVAQPAVVLASSnGIASFkCEYASPGKATEVRVTVLRQADSQVTEVCAATYMMGNELTFLDDSICTGTSSGNQVNLTIQGLRAMDTGLYICKVELMYPPPYYLGIGNGTQIYVIDPEPCP
DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M3

AMHVAQPAVVLASSRGIASFVCEYASPsNnTdEVRVTVLRQADSQVTEVCAATYMMGNELTFLDDSICTGTSSGNQVNLTIQGLRAMDTGLYICKVELMYPPPYYLGIGNGTQIYVIDPEPC
PDSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M4

AMHVAQPAVVLASSRGIASFVCEYASPGKATEVRVTVLRtaDqsVTEVCAATYMMGNELTFLDDSICTGTSSGNQVNLTIQGLRAMDTGLYICKVELMYPPPYYLGIGNGTQIYVIDPEPCP
DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M5

AMHVAQPAVVLASSRGIASFVCEYASPGKATEVRVTVLRQADSQVTEVCAATftekntvgFLDDSICTGTSSGNQVNLTIQGLRAMDTGLYICKVELMYPPPYYLGIGNGTQIYVIDPEPCP
DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

FIG. 56A

CTLA-4Fc M6

AMHVAQPAVVLASSRGIASFVCEYASPGKATEVRVTVLRQADSQVTEVCA*TYMMGNELTFLDDSICTGTSSGNQVNLTIQGLRAMDTGLYICKVELMYPPPYYLGIGNGTQIYVIDPEPCP
DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M7

AMHVAQPAVVLASSRGIASFVCEYASPGKATEVRVTVLRQADSQVTEVCAATYMMGNELTFLDypicxsGTSSGNQVNLTIQGLRAMDTGLYICKVELMYPPPYYLGIGNGTQIYVIDPEPCP
DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK CTLA-4Fc M8

AMHVAQPAVVLASSRGIASFVCEYASPGKATEVRVTVLRQADSQVTEVCAATYMMGNELTFLDDSICTGTSneseVNLTIQGLRAMDTGLYICKVELMYPPPYYLGIGNGTQIYVIDPEPCP
DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK CTLA-4Fc M9

AMHVAQPAVVLASSRGIASFVCEYASPGKATEVRVTVLRQADSQVTEVCAATYMMGNELTFLDDSICTGTSSGNQVNLTIQGLRAMvDTGLYICKVELMYPPPYYLGIGNGTQIYVIDPEPC
PDSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M10

AMHVAQPAVVLASSRGIASFVCEYASPGKATEVRVTVLRQADSQVTEVCAATYMMGNELTFLDDSICTGTSSGNQVNLTIQGLRAMMDTGLYiCKVELMYPPPYYLGIGNGTQIYVIDPEPC
PDSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M11

AMHVAQPAVVLASSRGIASFVCEYASPGKATEVRVTVLRQADSQVTEVCAATYMMGNELTFLDDSICTGTSSGNQVNLTIQGLRAMDTGLYICKVELMYPPPYfvGssGNGTQIYVIDPEPCP
DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

FIG. 56B

CTLA-4Fc WT

AMHVAQPAVVLASSRGIASFVCEYASPGKATEVRVTVLRQADSQVTEVCAATYMMGNELTFLDDSICTGTSSGNQVNLTIQGLRAMDTGLYICKVELMYPPPYYLGIGNGTQIYVIDPEPCP
DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M12 iqvtqPsVVLASSRGIASFVCEYASPGKATEVRVTVLRQADSQVTEVCAATftekntvgFLDDSICTGTfnesrVNLTIQGLRAMDTGLYICKVELMYPPPYfvGmGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK CTLA-4Fc M13

MHVAQPAVVLASSRGIASFVCEYASPGKyTEVRVTVLRQADSQVTEVCAATYMMGNELTFLDDSICTGTSSGNQVNLTIQGLRAMDTGLYICKVELMYPPPYfvGmGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M14 iqvtqPsVVLASSRGIASFVCEYASPGKATEVRVTVLRQADSQVTEVCAATftekntvgFLDDSICTGTSSGNQVNLTIQGLRAMDTGLYICKVELMYPPPYfvGmGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK CTLA-4Fc M15

MHVAQPAVVLASSRGIASFVCEYASPGKyTEVRVTVLRQADSQVTEVCAATYMMGNELTFLDDSICTGTSSGNQVNLTIQGLRAMDTGLYICKVELMYPPPYYeGIGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M16 iqvtqPsVVLASSRGIASFVCEYASPGKATEVRVTVLRQADSQVTEVCAATftekntvgFLDDSICTGTfnesrVNLTIQGLRAMDTGLYICKVELMYPPPYfvGmGNGTQIYVIDPEPCPD
SDQEPKSSDKTHTSPPSPAPELLGGSSVFLFPPKPKDTLyItRePEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK CTLA-4Fc M17

MHVAQPAVVLASSRGIASFVCEYASPGKyTEVRVTVLRQADSQVTEVCAATYMMGNELTFLDDSICTGTSSGNQVNLTIQGLRAMDTGLYICKVELMYPPPYfeGmGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

SEQUENCE LISTING

```
<160> NUMBER OF SEQ ID NOS: 90

<210> SEQ ID NO 1
<211> LENGTH: 107
<212> TYPE: PRT
<213> ORGANISM: Mus musculus

<400> SEQUENCE: 1

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60
```

```
Ser Gly Ser Gly Thr Gln Tyr Ser Leu Lys Ile Asn Ser Leu Gln Ser
 65                  70                  75                  80

Glu Asp Phe Gly Thr Tyr Phe Cys Gln His Leu Trp Gly Thr Pro Tyr
                 85                  90                  95

Thr Phe Gly Gly Gly Thr Lys Leu Glu Ile Lys
                100                 105

<210> SEQ ID NO 2
<211> LENGTH: 125
<212> TYPE: PRT
<213> ORGANISM: Mus musculus

<400> SEQUENCE: 2

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Ser Tyr
                20                  25                  30

Gly Leu Ser Trp Val Arg Gln Pro Pro Gly Lys Gly Leu Glu Trp Leu
             35                  40                  45

Gly Val Ile Trp Tyr Asp Gly Asn Thr Asn Phe His Ser Ala Leu Ile
         50                  55                  60

Ser Arg Leu Thr Ile Ser Lys Asp Asn Ser Lys Ser Gln Val Phe Leu
 65                  70                  75                  80

Glu Leu Asn Ser Leu Gln Thr Asp Asp Thr Ala Thr Tyr Tyr Cys Ala
                 85                  90                  95

Lys Thr Glu Gly His Tyr Tyr Gly Ser Asn Tyr Gly Tyr Tyr Ala Leu
                100                 105                 110

Asp Tyr Trp Gly Gln Gly Thr Ser Val Thr Val Ser Ser
             115                 120                 125

<210> SEQ ID NO 3
<211> LENGTH: 329
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
             115                 120                 125

Lys Pro Lys Asp Thr Leu Met Ile Ser Arg Thr Pro Glu Val Thr Cys
         130                 135                 140

Val Val Val Asp Val Ser His Glu Asp Pro Glu Val Lys Phe Asn Trp
145                  150                 155                 160
```

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 4
<211> LENGTH: 329
<212> TYPE: PRT
<213> ORGANISM: Artificial Sequence
<220> FEATURE:
<223> OTHER INFORMATION: Engineered fragment

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ala Thr Tyr Arg Val Val Ser Val Leu Thr Val Leu
            180                 185                 190

```
            His Gln Asp Trp Leu Asn Gly Lys Glu Tyr Lys Cys Lys Val Ser Asn
                        195                 200                 205

Lys Ala Leu Pro Ala Pro Ile Ala Ala Thr Ile Ser Lys Ala Lys Gly
            210                 215                 220

Gln Pro Arg Glu Pro Gln Val Tyr Thr Leu Pro Pro Ser Arg Asp Glu
        225                 230                 235                 240

Leu Thr Lys Asn Gln Val Ser Leu Thr Cys Leu Val Lys Gly Phe Tyr
                        245                 250                 255

Pro Ser Asp Ile Ala Val Glu Trp Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
        305                 310                 315                 320

Gln Lys Ser Leu Ser Leu Ser Pro Gly
                        325

<210> SEQ ID NO 5
<211> LENGTH: 1437
<212> TYPE: DNA
<213> ORGANISM: Artificial Sequence
<220> FEATURE:
<223> OTHER INFORMATION: Optimized fragment

<400> SEQUENCE: 5
```

| | | | | | |
|---|---|---|---|---|---|
| atggacccca | agggcagcct | gagctggaga | atcctgctgt | tcctgagcct | ggccttcgag | 60 |
| ctgagctacg | ccaggtgca | gctgaaagag | tctggccctg | gcctggtggc | cccttcccag | 120 |
| tccctgtcta | tcacctgtac | cgtgtccggc | ttctccctga | cctcctacgg | cctgtcttgg | 180 |
| gtgcgacagc | ctcctggcaa | gggcctggaa | tggctgggag | tgatttggta | cgacggcaac | 240 |
| accaacttcc | actccgccct | gatctcccgg | ctgaccatct | ccaaggacaa | ctccaagtcc | 300 |
| caggtgttcc | tggaactgaa | ctccctgcag | accgacgaca | ccgccaccta | ctactgcgct | 360 |
| aagaccgagg | ccactacta | cggctccaac | tacggctact | acgccctgga | ctattgggc | 420 |
| cagggcaccct | ccgtgaccgt | gtcctctgct | agcaccaagg | gcccagcgt | gttccctctg | 480 |
| gcccccagca | gcaagagcac | cagcggcgga | accgccgccc | tgggctgcct | ggtgaaggac | 540 |
| tacttccccg | agcccgtgac | cgtgtcctgg | aacagcggcg | ctctgaccag | cggagtgcac | 600 |
| accttccctg | ccgtgctgca | gagcagcggc | ctgtactccc | tgagcagcgt | ggtgaccgtg | 660 |
| cccagcagca | gcctgggcac | ccagacctac | atctgcaacg | tgaaccacaa | gcccctccaac | 720 |
| accaaggtgg | acaagaaggt | ggagcctaag | agctgcgaca | agacccacac | ctgcccctcc | 780 |
| tgccccgccc | ccgagctgct | gggcggaccc | agcgtgttcc | tgttccctcc | caagcccaag | 840 |
| gacaccctgt | acatcacccg | gaacccgag | gtgacctgcg | tggtggtgga | cgtgagccac | 900 |
| gaggaccccg | aggtgaagtt | caactggtac | gtggacggcg | tggaggtgca | caacgccaag | 960 |
| accaagcctc | gggaggagca | gtacaacgcc | acctaccgcg | tggtgagcgt | gctgaccgtg | 1020 |
| ctgcaccagg | actggctgaa | cggcaaggag | tacaagtgca | aggtgagcaa | caaggccctg | 1080 |
| cccgctccca | tcgcagccac | catcagcaag | gccaagggcc | agccccggga | gcctcaggtg | 1140 |
| tacaccctgc | cccccagccg | cgacgagctg | accaagaacc | aggtgagcct | gacctgcctg | 1200 |
| gtgaagggct | tctaccctc | cgacatcgcc | gtggagtggg | agagcaacgg | ccagcctgag | 1260 |

```
aacaactaca agaccacccc tcccgtgctg acagcgacg gcagcttctt cctgtacagc    1320
aagctgaccg tggacaagtc ccggtggcag cagggcaacg tgttcagctg cagcgtgatg    1380
cacgaggccc tgcacaacca ctacacccag aagagcctga gcctgagccc cggatag       1437
```

<210> SEQ ID NO 6
<211> LENGTH: 478
<212> TYPE: PRT
<213> ORGANISM: Artificial Sequence
<220> FEATURE:
<223> OTHER INFORMATION: Optimized fragment

<400> SEQUENCE: 6

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Lys Glu Ser Gly
            20                  25                  30

Pro Gly Leu Val Ala Pro Ser Gln Ser Leu Ser Ile Thr Cys Thr Val
        35                  40                  45

Ser Gly Phe Ser Leu Thr Ser Tyr Gly Leu Ser Trp Val Arg Gln Pro
    50                  55                  60

Pro Gly Lys Gly Leu Glu Trp Leu Gly Val Ile Trp Tyr Asp Gly Asn
65                  70                  75                  80

Thr Asn Phe His Ser Ala Leu Ile Ser Arg Leu Thr Ile Ser Lys Asp
                85                  90                  95

Asn Ser Lys Ser Gln Val Phe Leu Glu Leu Asn Ser Leu Gln Thr Asp
            100                 105                 110

Asp Thr Ala Thr Tyr Tyr Cys Ala Lys Thr Glu Gly His Tyr Tyr Gly
        115                 120                 125

Ser Asn Tyr Gly Tyr Tyr Ala Leu Asp Tyr Trp Gly Gln Gly Thr Ser
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Tyr Ile Thr Arg Glu
        275                 280                 285

Pro Glu Val Thr Cys Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ala Thr Tyr Arg Val Val Ser
                325                 330                 335
```

```
Val Leu Thr Val Leu His Gln Asp Trp Leu Asn Gly Lys Glu Tyr Lys
                340                 345                 350

Cys Lys Val Ser Asn Lys Ala Leu Pro Ala Pro Ile Ala Ala Thr Ile
            355                 360                 365

Ser Lys Ala Lys Gly Gln Pro Arg Glu Pro Gln Val Tyr Thr Leu Pro
        370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly
465                 470                 475

<210> SEQ ID NO 7
<211> LENGTH: 705
<212> TYPE: DNA
<213> ORGANISM: Artificial Sequence
<220> FEATURE:
<223> OTHER INFORMATION: Optimized fragment

<400> SEQUENCE: 7
atggagaccg acaccctgct gctctgggtg ctgctgctct gggtgcccgg ctccaccgga      60
gacatccaga tgacccagtc ccccgcctcc ctgtctgtgt ctgtgggcga gacagtgacc     120
atcacctgtc gggcctccga gaacatctac tccaacctgg cctggtatca gcagaagcag     180
ggcaagtccc ctcagctgct ggtgtacgcc gccaccaatc tggctgatgg cgtgccctcc     240
agattctccg gctctggctc tggcacccag tactccctga gatcaactc cctgcagtcc      300 gaggacttcg gcacctactt ttgccagcac ctgtggggca cccccctaca ctttggcggc     360
ggaacaaagc tggaaatcaa gcggaccgtg gccgccccca gcgtgttcat cttccctccc     420
agcgacgagc agctgaagtc tggcaccgcc agcgtggtgt gcctgctgaa caacttctac     480
ccccgcgagg ccaaggtgca gtggaaggtg gacaacgccc tgcagagcgg caacagccag     540
gagagcgtga ccgagcagga ctccaaggac agcacctaca gcctgagcag caccctgacc     600
ctgagcaagg ccgactacga gaagcacaag gtgtacgcct gcgaggtgac ccaccaggga     660
ctgtctagcc ccgtgaccaa gagcttcaac cggggcgagt gctaa                    705

<210> SEQ ID NO 8
<211> LENGTH: 234
<212> TYPE: PRT
<213> ORGANISM: Artificial Sequence
<220> FEATURE:
<223> OTHER INFORMATION: Chimeric

<400> SEQUENCE: 8

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45
```

```
Ile Tyr Ser Asn Leu Ala Trp Tyr Gln Gln Lys Gln Gly Lys Ser Pro
 50                  55                  60
Gln Leu Leu Val Tyr Ala Ala Thr Asn Leu Ala Asp Gly Val Pro Ser
 65                  70                  75                  80
Arg Phe Ser Gly Ser Gly Ser Gly Thr Gln Tyr Ser Leu Lys Ile Asn
                 85                  90                  95
Ser Leu Gln Ser Glu Asp Phe Gly Thr Tyr Phe Cys Gln His Leu Trp
                100                 105                 110
Gly Thr Pro Tyr Thr Phe Gly Gly Gly Thr Lys Leu Glu Ile Lys Arg
                115                 120                 125
Thr Val Ala Ala Pro Ser Val Phe Ile Phe Pro Pro Ser Asp Glu Gln
130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
                180                 185                 190
Tyr Ser Leu Ser Ser Thr Leu Thr Leu Ser Lys Ala Asp Tyr Glu Lys
                195                 200                 205
His Lys Val Tyr Ala Cys Glu Val Thr His Gln Gly Leu Ser Ser Pro
210                 215                 220
Val Thr Lys Ser Phe Asn Arg Gly Glu Cys
225                 230

<210> SEQ ID NO 9
<211> LENGTH: 478
<212> TYPE: PRT
<213> ORGANISM: Artificial Sequence
<220> FEATURE:
<223> OTHER INFORMATION: Humanized antibody fragment

<400> SEQUENCE: 9

Met Asp Pro Lys Gly Ser Leu Ser Trp Arg Ile Leu Leu Phe Leu Ser
1               5                   10                  15
Leu Ala Phe Glu Leu Ser Tyr Gly Gln Val Gln Leu Gln Glu Ser Gly
                20                  25                  30
Pro Gly Leu Val Lys Pro Ser Glu Thr Leu Ser Leu Thr Cys Thr Val
                35                  40                  45
Ser Gly Phe Ser Leu Thr Ser Tyr Gly Leu Ser Trp Ile Arg Gln Pro
 50                  55                  60
Pro Gly Lys Gly Leu Glu Trp Ile Gly Tyr Ile Trp Tyr Asp Gly Asn
 65                  70                  75                  80
Thr Asn Phe His Pro Ser Leu Lys Ser Arg Val Thr Ile Ser Lys Asp
                 85                  90                  95
Thr Ser Lys Asn Gln Phe Ser Leu Lys Leu Ser Ser Val Thr Ala Ala
                100                 105                 110
Asp Thr Ala Val Tyr Tyr Cys Ala Lys Thr Glu Gly His Tyr Tyr Gly
                115                 120                 125
Ser Asn Tyr Gly Tyr Tyr Ala Leu Asp Tyr Trp Gly Gln Gly Thr Ser
                130                 135                 140
Val Thr Val Ser Ser Ala Ser Thr Lys Gly Pro Ser Val Phe Pro Leu
145                 150                 155                 160
Ala Pro Ser Ser Lys Ser Thr Ser Gly Gly Thr Ala Ala Leu Gly Cys
                165                 170                 175
```

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Tyr Ile Thr Arg Glu
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ala Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Ala Ala Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly
465                 470                 475

<210> SEQ ID NO 10
<211> LENGTH: 1440
<212> TYPE: DNA
<213> ORGANISM: Artificial Sequence
<220> FEATURE:
<223> OTHER INFORMATION: Humanized antibody fragment

<400> SEQUENCE: 10
atggacccca agggcagcct gagctggaga atcctgctgt tcctgagcct ggccttcgag      60
ctgagctacg ccaggtgca gctgcaggaa tctggccctg gcctcgtgaa gccctccgag     120
acactgtctc tgacctgcac cgtgtccggc ttctccctga cctcctacgg cctgtcttgg     180
atcagacagc ccctggcaa gggcctggaa tggatcggct acatttggta cgacggcaac     240
accaacttcc accccagcct gaagtccaga gtgaccatct ccaaggacac ctccaagaac     300
cagttctctc tgaagctgtc ctccgtgacc gccgctgaca ccgccgtgta ctactgtgct     360

```
aagaccgagg gccactacta cggctccaac tacggctact acgccctgga ctattggggc      420
cagggcacct ctgtgaccgt gtcctctgct agcaccaagg gccccagcgt gttccctctg      480
gcccccagca gcaagagcac cagcggcgga accgccgccc tgggctgcct ggtgaaggac      540
tacttccccg agcccgtgac cgtgtcctgg aacagcggcg ctctgaccag cggagtgcac      600
accttccctg ccgtgctgca gagcagcggc ctgtactccc tgagcagcgt ggtgaccgtg      660
cccagcagca gcctgggcac ccagacctac atctgcaacg tgaaccacaa gccctccaac      720
accaaggtgg acaagaaggt ggagcctaag agctgcgaca gacccacac ctgccctccc       780 tgccccgccc ccgagctgct gggcggaccc agcgtgttcc tgttccctcc caagcccaag      840
gacaccctgt acatcacccg gaacccgag gtgacctgcg tggtggtgga cgtgagccac       900
gaggaccccg aggtgaagtt caactggtac gtggacggcg tggaggtgca caacgccaag      960
accaagcctc gggaggagca gtacaacgcc acctaccgcg tggtgagcgt gctgaccgtg     1020
ctgcaccagg actggctgaa cggcaaggag tacaagtgca aggtgagcaa caaggccctg     1080
cccgctccca tcgcagccac catcagcaag gccaagggcc agccccggga gcctcaggtg     1140
tacaccctgc cccccagccg cgacgagctg accaagaacc aggtgagcct gacctgcctg     1200
gtgaagggct tctacccctc cgacatcgcc gtggagtggg agagcaacgg ccagcctgag     1260
aacaactaca agaccacccc tcccgtgctg gacagcgacg gcagcttctt cctgtacagc     1320
aagctgaccg tggacaagtc ccggtggcag cagggcaacg tgttcagctg cagcgtgatg     1380
cacgaggccc tgcacaacca ctacacccag aagagcctga gcctgagccc cggatagtaa     1440
```

<210> SEQ ID NO 11
<211> LENGTH: 478
<212> TYPE: PRT
<213> ORGANISM: Artificial Sequence
<220> FEATURE:
<223> OTHER INFORMATION: Humanized antibody fragment

<400> SEQUENCE: 11

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Glu Ser Gly
            20                  25                  30

Pro Gly Leu Val Lys Pro Ser Glu Thr Leu Ser Leu Thr Cys Thr Val
        35                  40                  45

Ser Gly Phe Ser Leu Thr Ser Tyr Gly Leu Ser Trp Ile Arg Gln Pro
    50                  55                  60

Pro Gly Lys Gly Leu Glu Trp Ile Gly Tyr Ile Trp Tyr Asp Gly Asn
65                  70                  75                  80

Thr Asn Phe His Ser Ser Leu Lys Ser Arg Val Thr Ile Ser Lys Asp
                85                  90                  95

Thr Ser Lys Ser Gln Val Ser Leu Lys Leu Ser Ser Val Thr Ala Ala
            100                 105                 110

Asp Thr Ala Val Tyr Tyr Cys Ala Lys Thr Glu Gly His Tyr Tyr Gly
        115                 120                 125

Ser Asn Tyr Gly Tyr Tyr Ala Leu Asp Tyr Trp Gly Gln Gly Thr Leu
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175
```

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
            195                 200                 205

Ser Gly Leu Tyr Ser Leu Ser Ser Val Val Thr Val Pro Ser Ser Ser
            210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
            245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Tyr Ile Thr Arg Glu
            275                 280                 285

Pro Glu Val Thr Cys Val Val Val Asp Val Ser His Glu Asp Pro Glu
            290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ala Thr Tyr Arg Val Val Ser
            325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Ala Ala Thr Ile
            355                 360                 365

Ser Lys Ala Lys Gly Gln Pro Arg Glu Pro Gln Val Tyr Thr Leu Pro
            370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
            450                 455                 460

His Asn His Tyr Thr Gln Lys Ser Leu Ser Leu Ser Pro Gly
465                 470                 475

<210> SEQ ID NO 12
<211> LENGTH: 1440
<212> TYPE: DNA
<213> ORGANISM: Artificial Sequence
<220> FEATURE:
<223> OTHER INFORMATION: Humanized antibody

<400> SEQUENCE: 12
atggacccca agggcagcct gagctggaga atcctgctgt tcctgagcct ggccttcgag      60
ctgagctacg gccaggtgca gctgcaggaa tctggccctg gcctcgtgaa gccctccgag     120
acactgtctc tgacctgcac cgtgtccggc ttctccctga cctcctacgg cctgtcttgg     180
atcagacagc ccctggcaa gggcctggaa tggatcggct acatttggta cgacggcaac     240
accaacttcc actcctccct gaagtccaga gtgaccatct ccaaggacac ctccaagtcc     300
caggtgtctc tgaagctgtc ctccgtgacc gccgctgaca ccgccgtgta ctactgtgct     360

```
aagaccgagg gccactacta cggctccaac tacggctact acgccctgga ctattggggc    420
cagggcaccc tcgtgaccgt gtcctctgct agcaccaagg ccccagcgt gttccctctg    480
gccccagca gcaagagcac cagcggcgga accgccgccc tgggctgcct ggtgaaggac    540
tacttccccg agcccgtgac cgtgtcctgg aacagcggcg ctctgaccag cggagtgcac    600
accttccctg ccgtgctgca gagcagcggc ctgtactccc tgagcagcgt ggtgaccgtg    660
cccagcagca gcctgggcac ccagacctac atctgcaacg tgaaccacaa gccctccaac    720
accaaggtgg acaagaaggt ggagcctaag agctgcgaca gacccacac ctgccctccc    780
tgccccgccc ccgagctgct gggcggaccc agcgtgttcc tgttccctcc caagcccaag    840
gacaccctgt acatcacccg gaacccgag gtgacctgcg tggtggtgga cgtgagccac    900
gaggaccccg aggtgaagtt caactggtac gtggacggcg tggaggtgca aacgccaag    960
accaagcctc gggaggagca gtacaacgcc acctaccgcg tggtgagcgt gctgaccgtg    1020
ctgcaccagg actggctgaa cggcaaggag tacaagtgca aggtgagcaa caaggccctg    1080
cccgctccca tcgcagccac catcagcaag gccaagggcc agccccggga gcctcaggtg    1140
tacaccctgc cccccagccg cgacgagctg accaagaacc aggtgagcct gacctgcctg    1200
gtgaagggct tctaccctc cgacatcgcc gtggagtggg agagcaacgg ccagcctgag    1260
aacaactaca agaccacccc tcccgtgctg gacagcgacg gcagcttctt cctgtacagc    1320
aagctgaccg tggacaagtc ccggtggcag cagggcaacg tgttcagctg cagcgtgatg    1380
cacgaggccc tgcacaacca ctacacccag aagagcctga gcctgagccc cggatagtaa  1440
```

<210> SEQ ID NO 13
<211> LENGTH: 478
<212> TYPE: PRT
<213> ORGANISM: Artificial Sequence
<220> FEATURE:
<223> OTHER INFORMATION: Humanized antibody

<400> SEQUENCE: 13

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Glu Ser Gly
            20                  25                  30

Pro Gly Leu Val Lys Pro Ser Glu Thr Leu Ser Leu Thr Cys Thr Val
        35                  40                  45

Ser Gly Phe Ser Leu Thr Ser Tyr Gly Leu Ser Trp Ile Arg Gln Pro
    50                  55                  60

Pro Gly Lys Gly Leu Glu Trp Ile Gly Tyr Ile Trp Tyr Asp Gly Asn
65                  70                  75                  80

Thr Asn Phe His Ser Pro Leu Lys Ser Arg Val Thr Ile Ser Val Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Lys Thr Glu Gly His Tyr Tyr Gly
        115                 120                 125

Ser Asn Tyr Gly Tyr Tyr Ala Leu Asp Tyr Trp Gly Gln Gly Thr Leu
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175
```

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Tyr Ile Thr Arg Glu
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ala Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Ala Ala Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly
465                 470                 475

<210> SEQ ID NO 14
<211> LENGTH: 1440
<212> TYPE: DNA
<213> ORGANISM: Artificial Sequence
<220> FEATURE:
<223> OTHER INFORMATION: Humanized antibody

<400> SEQUENCE: 14
atggacccca agggcagcct gagctggaga atcctgctgt tcctgagcct ggccttcgag     60
ctgagctacg ccaggtgca gctgcaggaa tctggccctg gcctcgtgaa gccctccgag    120
acactgtctc tgacctgcac cgtgtccggc ttctccctga cctcctacgg cctgtcttgg    180
atcagacagc ccctggcaa gggcctggaa tggatcggct acatttggta cgacggcaac    240
accaacttcc actccccact gaagtccaga gtgaccatct ccgtggacac ctccaagaac    300
cagttctctc tgaagctgtc ctccgtgacc gccgctgaca ccgccgtgta ctactgtgct    360

```
aagaccgagg gccactacta cggctccaac tacggctact acgccctgga ctattggggc    420
cagggcaccc tcgtgaccgt gtcctctgct agcaccaagg ccccagcgt gttccctctg      480 gcccccagca gcaagagcac cagcggcgga accgccgccc tgggctgcct ggtgaaggac    540
tacttccccg agcccgtgac cgtgtcctgg aacagcggcg ctctgaccag cggagtgcac    600
accttccctg ccgtgctgca gagcagcggc ctgtactccc tgagcagcgt ggtgaccgtg    660
cccagcagca gcctgggcac ccagacctac atctgcaacg tgaaccacaa gccctccaac    720
accaaggtgg acaagaaggt ggagcctaag agctgcgaca gacccacac ctgccctccc      780 tgccccgccc ccgagctgct gggcggaccc agcgtgttcc tgttccctcc caagcccaag    840
gacaccctgt acatcacccg gaacccgag gtgacctgcg tggtggtgga cgtgagccac      900
gaggaccccg aggtgaagtt caactggtac gtggacggcg tggaggtgca aacgccaag      960 accaagcctc gggaggagca gtacaacgcc acctaccgcg tggtgagcgt gctgaccgtg   1020
ctgcaccagg actggctgaa cggcaaggag tacaagtgca aggtgagcaa caaggccctg    1080
cccgctccca tcgcagccac catcagcaag gccaagggcc agccccggga gcctcaggtg    1140
tacaccctgc cccccagccg cgacgagctg accaagaacc aggtgagcct gacctgcctg    1200
gtgaagggct tctacccctc cgacatcgcc gtggagtggg agagcaacgg ccagcctgag    1260
aacaactaca agaccacccc tcccgtgctg gacagcgacg gcagcttctt cctgtacagc    1320
aagctgaccg tggacaagtc ccggtggcag caggggcaacg tgttcagctg cagcgtgatg    1380
cacgaggccc tgcacaacca ctacacccag aagagcctga gcctgagccc cggatagtaa   1440
```

```
<210> SEQ ID NO 15
<211> LENGTH: 234
<212> TYPE: PRT
<213> ORGANISM: Artificial Sequence
<220> FEATURE:
<223> OTHER INFORMATION: Humanized antibody

<400> SEQUENCE: 15

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Glu Asn
            35                  40                  45

Ile Tyr Ser Asn Leu Ala Trp Tyr Gln Gln Lys Pro Gly Lys Ala Pro
        50                  55                  60

Lys Leu Leu Leu Tyr Ala Ala Thr Asn Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln His Leu Trp
                100                 105                 110

Gly Thr Pro Tyr Thr Phe Gly Gly Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175
```

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 16
<211> LENGTH: 705
<212> TYPE: DNA
<213> ORGANISM: Artificial Sequence
<220> FEATURE:
<223> OTHER INFORMATION: Humanized antibody

<400> SEQUENCE: 16

| | | |
|---|---|---|
| atggagaccg acaccctgct gctctgggtg ctgctgctct gggtgcccgg ctccaccgga | 60 |
| gacatccaga tgacccagtc ccctccagc ctgtctgcct ctgtgggcga cagagtgacc | 120 |
| atcacctgtc gggcctccga gaacatctac tccaacctgg cctggtatca gcagaagccc | 180 |
| ggcaaggccc ctaagctgct gctgtacgcc gccaccaatc tgcagtctgg cgtgccctcc | 240 |
| agattctccg gctctggctc tggcaccgac tttaccctga ccatcagctc cctgcagccc | 300 |
| gaggacttcg ccacctacta ctgccagcat ctgtggggca ccccctacac ctttggcgga | 360 |
| ggcaccaagc tggaaatcaa gcggaccgtg gccgccccca gcgtgttcat cttccctccc | 420 |
| agcgacgagc agctgaagtc tggcaccgcc agcgtggtgt gcctgctgaa caacttctac | 480 |
| ccccgcgagg ccaaggtgca gtggaaggtg gacaacgccc tgcagagcgg caacagccag | 540 |
| gagagcgtga ccgagcagga ctccaaggac agcacctaca gcctgagcag caccctgacc | 600 |
| ctgagcaagg ccgactacga gaagcacaag gtgtacgcct gcgaggtgac ccaccaggga | 660 |
| ctgtctagcc ccgtgaccaa gagcttcaac cggggcgagt gctaa | 705 |

<210> SEQ ID NO 17
<211> LENGTH: 234
<212> TYPE: PRT
<213> ORGANISM: Artificial Sequence
<220> FEATURE:
<223> OTHER INFORMATION: Humanized Antibody

<400> SEQUENCE: 17

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asn
        35                  40                  45

Ile Tyr Ser Asn Leu Ala Trp Tyr Gln Gln Lys Gln Gly Lys Ala Pro
    50                  55                  60

Lys Leu Leu Leu Tyr Ala Ala Thr Asn Leu Gln Asp Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Phe Cys Gln His Leu Trp
            100                 105                 110

Gly Thr Pro Tyr Thr Phe Gly Gln Gly Thr Lys Leu Glu Ile Lys Arg

```
                115                 120                 125
Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230
```

<210> SEQ ID NO 18
<211> LENGTH: 705
<212> TYPE: DNA
<213> ORGANISM: Artificial Sequence
<220> FEATURE:
<223> OTHER INFORMATION: Humanized antibody

<400> SEQUENCE: 18

```
atggagaccg acaccctgct gctctgggtg ctgctgctct gggtgcccgg ctccaccgga        60
gacatccaga tgacccagtc ccctccagc ctgtctgcct ctgtgggcga cagagtgacc       120
atcacctgtc gggcctccga gaacatctac tccaacctgg cctggtatca gcagaagcag      180
ggcaaggccc ctaagctgct gctgtacgcc gccaccaatc tgcaggatgg cgtgccctcc      240
agattctccg gctctggctc tggcaccgac tacaccctga ccatcagctc cctgcagccc      300
gaggacttcg ccacctactt ctgccagcat ctgtggggca cccccctaca ctttggccag      360
ggcaccaagc tggaaatcaa gcggaccgtg gccgccccca gcgtgttcat cttccctccc      420
agcgacgagc agctgaagtc tggcaccgcc agcgtggtgt gcctgctgaa caacttctac      480
ccccgcgagg ccaaggtgca gtggaaggtg gacaacgccc tgcagagcgg caacagccaa      540
gagagcgtga ccgagcagga ctccaaggac agcacctaca gcctgagcag caccctgacc      600
ctgagcaagg ccgactacga gaagcacaag gtgtacgcct gcgaggtgac ccaccaggga      660
ctgtctagcc ccgtgaccaa gagcttcaac cggggcgagt gctaa                     705
```

<210> SEQ ID NO 19
<211> LENGTH: 234
<212> TYPE: PRT
<213> ORGANISM: Artificial Sequence
<220> FEATURE:
<223> OTHER INFORMATION: Humanized antibody

<400> SEQUENCE: 19

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asn
        35                  40                  45

Ile Tyr Ser Asn Leu Ala Trp Tyr Gln Gln Lys Pro Gly Lys Ala Pro
    50                  55                  60
```

```
Lys Leu Leu Ile Tyr Ala Ala Thr Ser Leu Gln Ser Gly Val Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Phe Ala Thr Tyr Tyr Cys Gln His Leu Trp
            100                 105                 110

Gly Thr Pro Tyr Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 20
<211> LENGTH: 705
<212> TYPE: DNA
<213> ORGANISM: Artificial Sequence
<220> FEATURE:
<223> OTHER INFORMATION: Humanized antibody

<400> SEQUENCE: 20
atggagaccg acaccctgct gctctgggtg ctgctgctct gggtgcccgg ctccaccgga      60
gacatccaga tgacccagtc ccctccagc ctgtctgcct ctgtgggcga cagagtgacc     120
atcacctgtc gggcctccga gaacatctac tccaacctgg cctggtatca gcagaagccc     180
ggcaaggccc ctaagctgct gatctacgcc gccaccagtc tgcagtctgg cgtgccctcc     240
agattctccg gctctggctc tggcaccgac tttaccctga ccatcagctc cctgcagccc     300
gaggacttcg ccacctacta ctgccagcat ctgtggggca ccccctacac ctttggcgga     360
ggcaccaagg tggaaatcaa gcggaccgtg gccgccccca gcgtgttcat cttccctccc     420
agcgacgagc agctgaagtc tggcaccgcc agcgtggtgt gcctgctgaa caacttctac     480
ccccgcgagg ccaaggtgca gtggaaggtg gacaacgccc tgcagagcgg caacagccag     540
gagagcgtga ccgagcagga ctccaaggac agcacctaca gcctgagcag caccctgacc     600
ctgagcaagg ccgactacga gaagcacaag gtgtacgcct gcgaggtgac ccaccaggga     660
ctgtctagcc ccgtgaccaa gagcttcaac cggggcgagt gctaa                    705

<210> SEQ ID NO 21
<211> LENGTH: 11
<212> TYPE: PRT
<213> ORGANISM: Artificial Sequence
<220> FEATURE:
<223> OTHER INFORMATION: Peptide fragment

<400> SEQUENCE: 21

Arg Ala Ser Glu Asn Ile Tyr Ser Asn Leu Ala
1               5                   10
```

<210> SEQ ID NO 22
<211> LENGTH: 7
<212> TYPE: PRT
<213> ORGANISM: Artificial Sequence
<220> FEATURE:
<223> OTHER INFORMATION: Peptide fragment

<400> SEQUENCE: 22

Ala Ala Thr Asn Leu Ala Asp
1               5

<210> SEQ ID NO 23
<211> LENGTH: 9
<212> TYPE: PRT
<213> ORGANISM: Artificial Sequence
<220> FEATURE:
<223> OTHER INFORMATION: Peptide fragment

<400> SEQUENCE: 23

Gln His Leu Trp Gly Thr Pro Tyr Thr
1               5

<210> SEQ ID NO 24
<211> LENGTH: 10
<212> TYPE: PRT
<213> ORGANISM: Artificial Sequence
<220> FEATURE:
<223> OTHER INFORMATION: Peptide fragment

<400> SEQUENCE: 24

Gly Phe Ser Leu Thr Ser Tyr Gly Leu Ser
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Peptide fragment

<400> SEQUENCE: 25

Val Ile Trp Tyr Asp Gly Asn Thr Asn Phe His Ser Ala Leu Ile Ser
1               5                   10                  15

Arg

<210> SEQ ID NO 26
<211> LENGTH: 17
<212> TYPE: PRT
<213> ORGANISM: Artificial Sequence
<220> FEATURE:
<223> OTHER INFORMATION: Peptide fragment

<400> SEQUENCE: 26

Thr Glu Gly His Tyr Tyr Gly Ser Asn Tyr Gly Tyr Tyr Ala Leu Asp
1               5                   10                  15

Tyr

<210> SEQ ID NO 27
<211> LENGTH: 149
<212> TYPE: PRT
<213> ORGANISM: Artificial Sequence
<220> FEATURE:
<223> OTHER INFORMATION: Humanized antibody

<400> SEQUENCE: 27

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Glu Ser Gly
            20                  25                  30

Pro Gly Leu Val Lys Pro Ser Glu Thr Leu Ser Leu Thr Cys Thr Val
        35                  40                  45

Ser Gly Phe Ser Leu Thr Ser Tyr Gly Leu Ser Trp Ile Arg Gln Pro
    50                  55                  60

Pro Gly Lys Gly Leu Glu Trp Ile Gly Tyr Ile Trp Tyr Asp Gly Asn
65                  70                  75                  80

Thr Asn Phe His Pro Ser Leu Lys Ser Arg Val Thr Ile Ser Lys Asp
            85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Lys Thr Glu Gly His Tyr Tyr Gly
            115                 120                 125

Ser Asn Tyr Gly Tyr Tyr Ala Leu Asp Tyr Trp Gly Gln Gly Thr Ser
    130                 135                 140

Val Thr Val Ser Ser
145

<210> SEQ ID NO 28
<211> LENGTH: 149
<212> TYPE: PRT
<213> ORGANISM: Artificial Sequence
<220> FEATURE:
<223> OTHER INFORMATION: Humanized antibody

<400> SEQUENCE: 28

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Glu Ser Gly
            20                  25                  30

Pro Gly Leu Val Lys Pro Ser Glu Thr Leu Ser Leu Thr Cys Thr Val
        35                  40                  45

Ser Gly Phe Ser Leu Thr Ser Tyr Gly Leu Ser Trp Ile Arg Gln Pro
    50                  55                  60

Pro Gly Lys Gly Leu Glu Trp Ile Gly Tyr Ile Trp Tyr Asp Gly Asn
65                  70                  75                  80

Thr Asn Phe His Ser Ser Leu Lys Ser Arg Val Thr Ile Ser Lys Asp
            85                  90                  95

Thr Ser Lys Ser Gln Val Ser Leu Lys Leu Ser Ser Val Thr Ala Ala
            100                 105                 110

Asp Thr Ala Val Tyr Tyr Cys Ala Lys Thr Glu Gly His Tyr Tyr Gly
            115                 120                 125

Ser Asn Tyr Gly Tyr Tyr Ala Leu Asp Tyr Trp Gly Gln Gly Thr Leu
    130                 135                 140

Val Thr Val Ser Ser
145

<210> SEQ ID NO 29
<211> LENGTH: 149
<212> TYPE: PRT
<213> ORGANISM: Artificial Sequence
<220> FEATURE:
<223> OTHER INFORMATION: Humanized antibody

<400> SEQUENCE: 29

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Glu Ser Gly
                20                  25                  30

Pro Gly Leu Val Lys Pro Ser Glu Thr Leu Ser Leu Thr Cys Thr Val
            35                  40                  45

Ser Gly Phe Ser Leu Thr Ser Tyr Gly Leu Ser Trp Ile Arg Gln Pro
    50                  55                  60

Pro Gly Lys Gly Leu Glu Trp Ile Gly Tyr Ile Trp Tyr Asp Gly Asn
65              70                  75                  80

Thr Asn Phe His Ser Pro Leu Lys Ser Arg Val Thr Ile Ser Val Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Lys Thr Glu Gly His Tyr Tyr Gly
        115                 120                 125

Ser Asn Tyr Gly Tyr Tyr Ala Leu Asp Tyr Trp Gly Gln Gly Thr Leu
    130                 135                 140

Val Thr Val Ser Ser
145

<210> SEQ ID NO 30
<211> LENGTH: 127
<212> TYPE: PRT
<213> ORGANISM: Artificial Sequence
<220> FEATURE:
<223> OTHER INFORMATION: Humanized antibody

<400> SEQUENCE: 30

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Glu Asn
            35                  40                  45

Ile Tyr Ser Asn Leu Ala Trp Tyr Gln Gln Lys Pro Gly Lys Ala Pro
    50                  55                  60

Lys Leu Leu Leu Tyr Ala Ala Thr Asn Leu Gln Ser Gly Val Pro Ser
65              70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln His Leu Trp
            100                 105                 110

Gly Thr Pro Tyr Thr Phe Gly Gly Gly Thr Lys Leu Glu Ile Lys
        115                 120                 125

<210> SEQ ID NO 31
<211> LENGTH: 127
<212> TYPE: PRT
<213> ORGANISM: Artificial Sequence
<220> FEATURE:
<223> OTHER INFORMATION: Humanized antibody

<400> SEQUENCE: 31

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asn
        35                  40                  45

Ile Tyr Ser Asn Leu Ala Trp Tyr Gln Gln Lys Gln Gly Lys Ala Pro
    50                  55                  60

Lys Leu Leu Tyr Ala Ala Thr Asn Leu Gln Asp Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Phe Cys Gln His Leu Trp
                100                 105                 110

Gly Thr Pro Tyr Thr Phe Gly Gln Gly Thr Lys Leu Glu Ile Lys
            115                 120                 125

<210> SEQ ID NO 32
<211> LENGTH: 127
<212> TYPE: PRT
<213> ORGANISM: Artificial Sequence
<220> FEATURE:
<223> OTHER INFORMATION: Humanized antibody

<400> SEQUENCE: 32

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asn
        35                  40                  45

Ile Tyr Ser Asn Leu Ala Trp Tyr Gln Gln Lys Pro Gly Lys Ala Pro
    50                  55                  60

Lys Leu Leu Ile Tyr Ala Ala Thr Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln His Leu Trp
                100                 105                 110

Gly Thr Pro Tyr Thr Phe Gly Gly Gly Thr Lys Val Glu Ile Lys
            115                 120                 125

<210> SEQ ID NO 33
<211> LENGTH: 17
<212> TYPE: PRT
<213> ORGANISM: Artificial Sequence
<220> FEATURE:
<223> OTHER INFORMATION: Peptide fragment

<400> SEQUENCE: 33

Tyr Ile Trp Tyr Asp Gly Asn Thr Asn Phe His Pro Ser Leu Lys Ser
1               5                   10                  15

Arg

<210> SEQ ID NO 34
<211> LENGTH: 17
<212> TYPE: PRT
<213> ORGANISM: Artificial Sequence
<220> FEATURE:
<223> OTHER INFORMATION: Peptide fragment

<400> SEQUENCE: 34

```
Tyr Ile Trp Tyr Asp Gly Asn Thr Asn Phe His Ser Ser Leu Lys Ser
1               5                   10                  15

Arg

<210> SEQ ID NO 35
<211> LENGTH: 17
<212> TYPE: PRT
<213> ORGANISM: Artificial Sequence
<220> FEATURE:
<223> OTHER INFORMATION: Peptide fragment

<400> SEQUENCE: 35

Tyr Ile Trp Tyr Asp Gly Asn Thr Asn Phe His Ser Pro Leu Lys Ser
1               5                   10                  15

Arg

<210> SEQ ID NO 36
<211> LENGTH: 7
<212> TYPE: PRT
<213> ORGANISM: Artificial Sequence
<220> FEATURE:
<223> OTHER INFORMATION: Peptide fragment

<400> SEQUENCE: 36

Ala Ala Thr Asn Leu Gln Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Peptide

<400> SEQUENCE: 37

Ala Ala Thr Asn Leu Gln Asp
1               5

<210> SEQ ID NO 38
<211> LENGTH: 7
<212> TYPE: PRT
<213> ORGANISM: Artificial Sequence
<220> FEATURE:
<223> OTHER INFORMATION: Peptide

<400> SEQUENCE: 38

Ala Ala Thr Ser Leu Gln Ser
1               5

<210> SEQ ID NO 39
<211> LENGTH: 358
<212> TYPE: PRT
<213> ORGANISM: Artificial Sequence
<220> FEATURE:
<223> OTHER INFORMATION: Fusion protein

<400> SEQUENCE: 39

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
                20                  25                  30

Val Arg Val Thr Val Leu Arg Gln Ala Asp Ser Gln Val Thr Glu Val
            35                  40                  45
```

```
Cys Ala Ala Thr Tyr Met Met Gly Asn Glu Leu Thr Phe Leu Asp Asp
     50                  55                  60

Ser Ile Cys Thr Gly Thr Ser Ser Gly Asn Gln Val Asn Leu Thr Ile
 65                  70                  75                  80

Gln Gly Leu Arg Ala Met Asp Thr Gly Leu Tyr Ile Cys Lys Val Glu
                 85                  90                  95

Leu Met Tyr Pro Pro Pro Tyr Leu Gly Ile Gly Asn Gly Thr Gln
                100                 105                 110

Ile Tyr Val Ile Asp Pro Glu Pro Cys Pro Asp Ser Asp Gln Glu Pro
             115                 120                 125

Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
             180                 185                 190

Val Glu Val His Asn Ala Lys Thr Lys Pro Arg Glu Glu Gln Tyr Asn
             195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
             260                 265                 270

Gln Val Ser Leu Thr Cys Leu Val Lys Gly Phe Tyr Pro Ser Asp Ile
             275                 280                 285

Ala Val Glu Trp Glu Ser Asn Gly Gln Pro Glu Asn Asn Tyr Lys Thr
             290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
                340                 345                 350

Ser Leu Ser Pro Gly Lys
            355

<210> SEQ ID NO 40
<211> LENGTH: 357
<212> TYPE: PRT
<213> ORGANISM: Artificial Sequence
<220> FEATURE:
<223> OTHER INFORMATION: Fusion protein

<400> SEQUENCE: 40

Ile Gln Val Thr Gln Pro Ser Val Val Leu Ala Ser Ser Arg Gly Ile
 1               5                  10                  15

Ala Ser Phe Val Cys Glu Tyr Ala Ser Pro Gly Lys Ala Thr Glu Val
                 20                  25                  30

Arg Val Thr Val Leu Arg Gln Ala Asp Ser Gln Val Thr Glu Val Cys
             35                  40                  45
```

```
Ala Ala Thr Tyr Met Met Gly Asn Glu Leu Thr Phe Leu Asp Asp Ser
 50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
            115                 120                 125

Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 41
<211> LENGTH: 358
<212> TYPE: PRT
<213> ORGANISM: Artificial Sequence
<220> FEATURE:
<223> OTHER INFORMATION: Fusion protein

<400> SEQUENCE: 41

Ala Met His Val Ala Gln Pro Ala Val Val Leu Ala Ser Ser His Gly
 1               5                  10                  15

Leu Ala Ser Phe Pro Cys Glu Tyr Ala Ser Pro Gly Lys Ala Thr Glu
                 20                  25                  30

Val Arg Val Thr Val Leu Arg Gln Ala Asp Ser Gln Val Thr Glu Val
                 35                  40                  45
```

Cys Ala Ala Thr Tyr Met Met Gly Asn Glu Leu Thr Phe Leu Asp Asp
    50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Leu Gly Ile Gly Asn Gly Thr Gln
            100                 105                 110

Ile Tyr Val Ile Asp Pro Glu Pro Cys Pro Asp Ser Asp Gln Glu Pro
            115                 120                 125

Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
            165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
            195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
            245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
            290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
            325                 330                 335

Ser Val Met His Glu Ala Leu His Asn His Tyr Thr Gln Lys Ser Leu
            340                 345                 350

Ser Leu Ser Pro Gly Lys
            355

<210> SEQ ID NO 42
<211> LENGTH: 359
<212> TYPE: PRT
<213> ORGANISM: Artificial Sequence
<220> FEATURE:
<223> OTHER INFORMATION: Fusion protein

<400> SEQUENCE: 42

Ala Met His Val Ala Gln Pro Ala Val Val Leu Ala Ser Ser Arg Gly
1               5                   10                  15

Ile Ala Ser Phe Val Cys Glu Tyr Ala Ser Pro Ser His Asn Thr Asp
                20                  25                  30

Glu Val Arg Val Thr Val Leu Arg Gln Ala Asp Ser Gln Val Thr Glu
            35                  40                  45

Val Cys Ala Ala Thr Tyr Met Met Gly Asn Glu Leu Thr Phe Leu Asp
 50                  55                  60

Asp Ser Ile Cys Thr Gly Thr Ser Ser Gly Asn Gln Val Asn Leu Thr
 65                  70                  75                  80

Ile Gln Gly Leu Arg Ala Met Asp Thr Gly Leu Tyr Ile Cys Lys Val
                 85                  90                  95

Glu Leu Met Tyr Pro Pro Tyr Tyr Leu Gly Ile Gly Asn Gly Thr
            100                 105                 110

Gln Ile Tyr Val Ile Asp Pro Glu Pro Cys Pro Asp Ser Asp Gln Glu
             115                 120                 125

Pro Lys Ser Ser Asp Lys Thr His Thr Ser Pro Pro Ser Pro Ala Pro
130                 135                 140

Glu Leu Leu Gly Gly Ser Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 43
<211> LENGTH: 358
<212> TYPE: PRT
<213> ORGANISM: Artificial Sequence
<220> FEATURE:
<223> OTHER INFORMATION: Fusion protein

<400> SEQUENCE: 43

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
                20                  25                  30

Val Arg Val Thr Val Leu Arg Thr Asn Asp Gln Met Val Thr Glu Val
            35                  40                  45

Cys Ala Ala Thr Tyr Met Met Gly Asn Glu Leu Thr Phe Leu Asp Asp
 50                  55                  60

Ser Ile Cys Thr Gly Thr Ser Ser Gly Asn Gln Val Asn Leu Thr Ile
 65                  70                  75                  80

Gln Gly Leu Arg Ala Met Asp Thr Gly Leu Tyr Ile Cys Lys Val Glu
                 85                  90                  95

Leu Met Tyr Pro Pro Pro Tyr Leu Gly Ile Gly Asn Gly Thr Gln
                100                 105                 110

Ile Tyr Val Ile Asp Pro Glu Pro Cys Pro Asp Ser Asp Gln Glu Pro
                115                 120                 125

Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
                180                 185                 190

Val Glu Val His Asn Ala Lys Thr Lys Pro Arg Glu Glu Gln Tyr Asn
                195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
                260                 265                 270

Gln Val Ser Leu Thr Cys Leu Val Lys Gly Phe Tyr Pro Ser Asp Ile
                275                 280                 285

Ala Val Glu Trp Glu Ser Asn Gly Gln Pro Glu Asn Asn Tyr Lys Thr
                290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
                340                 345                 350

Ser Leu Ser Pro Gly Lys
            355

<210> SEQ ID NO 44
<211> LENGTH: 358
<212> TYPE: PRT
<213> ORGANISM: Artificial Sequence
<220> FEATURE:
<223> OTHER INFORMATION: Fusion protein

<400> SEQUENCE: 44

Ala Met His Val Ala Gln Pro Ala Val Val Leu Ala Ser Ser Arg Gly
1               5                  10                  15

Ile Ala Ser Phe Val Cys Glu Tyr Ala Ser Pro Gly Lys Ala Thr Glu
                20                  25                  30

Val Arg Val Thr Val Leu Arg Gln Ala Asp Ser Gln Val Thr Glu Val
                35                  40                  45

Cys Ala Ala Thr Phe Thr Glu Lys Asn Thr Val Gly Phe Leu Asp Asp
 50                  55                  60

Ser Ile Cys Thr Gly Thr Ser Ser Gly Asn Gln Val Asn Leu Thr Ile
 65                  70                  75                  80

Gln Gly Leu Arg Ala Met Asp Thr Gly Leu Tyr Ile Cys Lys Val Glu
                 85                  90                  95

Leu Met Tyr Pro Pro Pro Tyr Leu Gly Ile Gly Asn Gly Thr Gln
                100                 105                 110

Ile Tyr Val Ile Asp Pro Glu Pro Cys Pro Asp Ser Asp Gln Glu Pro
                115                 120                 125

Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
                180                 185                 190

Val Glu Val His Asn Ala Lys Thr Lys Pro Arg Glu Glu Gln Tyr Asn
                195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
                260                 265                 270

Gln Val Ser Leu Thr Cys Leu Val Lys Gly Phe Tyr Pro Ser Asp Ile
                275                 280                 285

Ala Val Glu Trp Glu Ser Asn Gly Gln Pro Glu Asn Asn Tyr Lys Thr
                290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
                340                 345                 350

Ser Leu Ser Pro Gly Lys
                355

<210> SEQ ID NO 45
<211> LENGTH: 358
<212> TYPE: PRT
<213> ORGANISM: Artificial Sequence
<220> FEATURE:
<223> OTHER INFORMATION: Fusion protein

<400> SEQUENCE: 45

Ala Met His Val Ala Gln Pro Ala Val Val Leu Ala Ser Ser Arg Gly
 1               5                  10                  15

Ile Ala Ser Phe Val Cys Glu Tyr Ala Ser Pro Gly Lys Ala Thr Glu
                 20                  25                  30

Val Arg Val Thr Val Leu Arg Gln Ala Asp Ser Gln Val Thr Glu Val
                 35                  40                  45

```
Cys Ala Thr Thr Tyr Met Met Gly Asn Glu Leu Thr Phe Leu Asp Asp
 50                  55                  60

Ser Ile Cys Thr Gly Thr Ser Ser Gly Asn Gln Val Asn Leu Thr Ile
 65                  70                  75                  80

Gln Gly Leu Arg Ala Met Asp Thr Gly Leu Tyr Ile Cys Lys Val Glu
                 85                  90                  95

Leu Met Tyr Pro Pro Pro Tyr Leu Gly Ile Gly Asn Gly Thr Gln
            100                 105                 110

Ile Tyr Val Ile Asp Pro Glu Pro Cys Pro Asp Ser Asp Gln Glu Pro
            115                 120                 125

Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
            195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
            355

<210> SEQ ID NO 46
<211> LENGTH: 358
<212> TYPE: PRT
<213> ORGANISM: Artificial Sequence
<220> FEATURE:
<223> OTHER INFORMATION: Fusion protein

<400> SEQUENCE: 46

Ala Met His Val Ala Gln Pro Ala Val Val Leu Ala Ser Ser Arg Gly
 1               5                  10                  15

Ile Ala Ser Phe Val Cys Glu Tyr Ala Ser Pro Gly Lys Ala Thr Glu
                 20                  25                  30

Val Arg Val Thr Val Leu Arg Gln Ala Asp Ser Gln Val Thr Glu Val
             35                  40                  45
```

Cys Ala Ala Thr Tyr Met Met Gly Asn Glu Leu Thr Phe Leu Asp Tyr
            50                  55                  60

Pro Phe Cys Ser Gly Thr Ser Ser Gly Asn Gln Val Asn Leu Thr Ile
 65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Leu Gly Ile Gly Asn Gly Thr Gln
                100                 105                 110

Ile Tyr Val Ile Asp Pro Glu Pro Cys Pro Asp Ser Asp Gln Glu Pro
            115                 120                 125

Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
            195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
            290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
                340                 345                 350

Ser Leu Ser Pro Gly Lys
            355

<210> SEQ ID NO 47
<211> LENGTH: 358
<212> TYPE: PRT
<213> ORGANISM: Artificial Sequence
<220> FEATURE:
<223> OTHER INFORMATION: Fusion protein

<400> SEQUENCE: 47

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
                20                  25                  30

Val Arg Val Thr Val Leu Arg Gln Ala Asp Ser Gln Val Thr Glu Val
            35                  40                  45

```
Cys Ala Ala Thr Tyr Met Met Gly Asn Glu Leu Thr Phe Leu Asp Asp
 50                  55                  60
Ser Ile Cys Thr Gly Thr Phe Asn Glu Ser Arg Val Asn Leu Thr Ile
 65                  70                  75                  80
Gln Gly Leu Arg Ala Met Asp Thr Gly Leu Tyr Ile Cys Lys Val Glu
                 85                  90                  95
Leu Met Tyr Pro Pro Pro Tyr Leu Gly Ile Gly Asn Gly Thr Gln
                100                 105                110
Ile Tyr Val Ile Asp Pro Glu Pro Cys Pro Asp Ser Asp Gln Glu Pro
                115                 120                 125
Lys Ser Ser Asp Lys Thr His Thr Ser Pro Pro Ser Pro Ala Pro Glu
130                 135                 140
Leu Leu Gly Gly Ser Ser Val Phe Leu Phe Pro Pro Lys Pro Lys Asp
145                 150                 155                 160
Thr Leu Met Ile Ser Arg Thr Pro Glu Val Thr Cys Val Val Val Asp
                165                 170                 175
Val Ser His Glu Asp Pro Glu Val Lys Phe Asn Trp Tyr Val Asp Gly
                180                 185                 190
Val Glu Val His Asn Ala Lys Thr Lys Pro Arg Glu Glu Gln Tyr Asn
                195                 200                 205
Ser Thr Tyr Arg Val Val Ser Val Leu Thr Val Leu His Gln Asp Trp
210                 215                 220
Leu Asn Gly Lys Glu Tyr Lys Cys Lys Val Ser Asn Lys Ala Leu Pro
225                 230                 235                 240
Ala Pro Ile Glu Lys Thr Ile Ser Lys Ala Lys Gly Gln Pro Arg Glu
                245                 250                 255
Pro Gln Val Tyr Thr Leu Pro Pro Ser Arg Asp Glu Leu Thr Lys Asn
                260                 265                 270
Gln Val Ser Leu Thr Cys Leu Val Lys Gly Phe Tyr Pro Ser Asp Ile
                275                 280                 285
Ala Val Glu Trp Glu Ser Asn Gly Gln Pro Glu Asn Asn Tyr Lys Thr
                290                 295                 300
Thr Pro Pro Val Leu Asp Ser Asp Gly Ser Phe Phe Leu Tyr Ser Lys
305                 310                 315                 320
Leu Thr Val Asp Lys Ser Arg Trp Gln Gln Gly Asn Val Phe Ser Cys
                325                 330                 335
Ser Val Met His Glu Ala Leu His Asn His Tyr Thr Gln Lys Ser Leu
                340                 345                 350
Ser Leu Ser Pro Gly Lys
            355

<210> SEQ ID NO 48
<211> LENGTH: 359
<212> TYPE: PRT
<213> ORGANISM: Artificial Sequence
<220> FEATURE:
<223> OTHER INFORMATION: Fusion protein

<400> SEQUENCE: 48

Ala Met His Val Ala Gln Pro Ala Val Val Leu Ala Ser Ser Arg Gly
 1               5                  10                  15
Ile Ala Ser Phe Val Cys Glu Tyr Ala Ser Pro Gly Lys Ala Thr Glu
                 20                  25                  30
Val Arg Val Thr Val Leu Arg Gln Ala Asp Ser Gln Val Thr Glu Val
                 35                  40                  45
```

```
Cys Ala Ala Thr Tyr Met Met Gly Asn Glu Leu Thr Phe Leu Asp Asp
     50                  55                  60
Ser Ile Cys Thr Gly Thr Ser Ser Gly Asn Gln Val Asn Leu Thr Ile
 65                  70                  75                  80
Gln Gly Leu Arg Ala Met Val Asp Thr Gly Leu Tyr Ile Cys Lys Val
                 85                  90                  95
Glu Leu Met Tyr Pro Pro Pro Tyr Leu Gly Ile Gly Asn Gly Thr
            100                 105                 110
Gln Ile Tyr Val Ile Asp Pro Glu Pro Cys Pro Asp Ser Asp Gln Glu
            115                 120                 125
Pro Lys Ser Ser Asp Lys Thr His Thr Ser Pro Pro Ser Pro Ala Pro
130                 135                 140
Glu Leu Leu Gly Gly Ser Ser Val Phe Leu Phe Pro Pro Lys Pro Lys
145                 150                 155                 160
Asp Thr Leu Met Ile Ser Arg Thr Pro Glu Val Thr Cys Val Val Val
                165                 170                 175
Asp Val Ser His Glu Asp Pro Glu Val Lys Phe Asn Trp Tyr Val Asp
            180                 185                 190
Gly Val Glu Val His Asn Ala Lys Thr Lys Pro Arg Glu Glu Gln Tyr
            195                 200                 205
Asn Ser Thr Tyr Arg Val Val Ser Val Leu Thr Val Leu His Gln Asp
210                 215                 220
Trp Leu Asn Gly Lys Glu Tyr Lys Cys Lys Val Ser Asn Lys Ala Leu
225                 230                 235                 240
Pro Ala Pro Ile Glu Lys Thr Ile Ser Lys Ala Lys Gly Gln Pro Arg
                245                 250                 255
Glu Pro Gln Val Tyr Thr Leu Pro Pro Ser Arg Asp Glu Leu Thr Lys
            260                 265                 270
Asn Gln Val Ser Leu Thr Cys Leu Val Lys Gly Phe Tyr Pro Ser Asp
            275                 280                 285
Ile Ala Val Glu Trp Glu Ser Asn Gly Gln Pro Glu Asn Asn Tyr Lys
            290                 295                 300
Thr Thr Pro Pro Val Leu Asp Ser Asp Gly Ser Phe Phe Leu Tyr Ser
305                 310                 315                 320
Lys Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
            340                 345                 350
Leu Ser Leu Ser Pro Gly Lys
            355

<210> SEQ ID NO 49
<211> LENGTH: 359
<212> TYPE: PRT
<213> ORGANISM: Artificial Sequence
<220> FEATURE:
<223> OTHER INFORMATION: Fusion protein

<400> SEQUENCE: 49

Ala Met His Val Ala Gln Pro Ala Val Val Leu Ala Ser Ser Arg Gly
 1               5                  10                  15
Ile Ala Ser Phe Val Cys Glu Tyr Ala Ser Pro Gly Lys Ala Thr Glu
                20                  25                  30
Val Arg Val Thr Val Leu Arg Gln Ala Asp Ser Gln Val Thr Glu Val
            35                  40                  45
```

```
Cys Ala Ala Thr Tyr Met Met Gly Asn Glu Leu Thr Phe Leu Asp Asp
 50                  55                  60

Ser Ile Cys Thr Gly Thr Ser Ser Gly Asn Gln Val Asn Leu Thr Ile
 65                  70                  75                  80

Gln Gly Leu Arg Ala Met Met Asp Thr Gly Leu Tyr Leu Cys Lys Val
                 85                  90                  95

Glu Leu Met Tyr Pro Pro Pro Tyr Leu Gly Ile Gly Asn Gly Thr
            100                 105                 110

Gln Ile Tyr Val Ile Asp Pro Glu Pro Cys Pro Asp Ser Asp Gln Glu
            115                 120                 125

Pro Lys Ser Ser Asp Lys Thr His Thr Ser Pro Pro Ser Pro Ala Pro
130                 135                 140

Glu Leu Leu Gly Gly Ser Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
            195                 200                 205

Asn Ser Thr Tyr Arg Val Val Ser Val Leu Thr Val Leu His Gln Asp
210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
            275                 280                 285

Ile Ala Val Glu Trp Glu Ser Asn Gly Gln Pro Glu Asn Asn Tyr Lys
290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
            355

<210> SEQ ID NO 50
<211> LENGTH: 358
<212> TYPE: PRT
<213> ORGANISM: Artificial Sequence
<220> FEATURE:
<223> OTHER INFORMATION: Fusion protein

<400> SEQUENCE: 50

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
                20                  25                  30

Val Arg Val Thr Val Leu Arg Gln Ala Asp Ser Gln Val Thr Glu Val
            35                  40                  45
```

```
Cys Ala Ala Thr Tyr Met Met Gly Asn Glu Leu Thr Phe Leu Asp Asp
 50                  55                  60

Ser Ile Cys Thr Gly Thr Ser Ser Gly Asn Gln Val Asn Leu Thr Ile
 65                  70                  75                  80

Gln Gly Leu Arg Ala Met Asp Thr Gly Leu Tyr Ile Cys Lys Val Glu
                 85                  90                  95

Leu Met Tyr Pro Pro Pro Tyr Phe Val Gly Met Gly Asn Gly Thr Gln
                100                 105                 110

Ile Tyr Val Ile Asp Pro Glu Pro Cys Pro Asp Ser Asp Gln Glu Pro
            115                 120                 125

Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 51
<211> LENGTH: 357
<212> TYPE: PRT
<213> ORGANISM: Artificial Sequence
<220> FEATURE:
<223> OTHER INFORMATION: Fusion protein

<400> SEQUENCE: 51

Ile Gln Val Thr Gln Pro Ser Val Val Leu Ala Ser Ser Arg Gly Ile
 1               5                  10                  15

Ala Ser Phe Val Cys Glu Tyr Ala Ser Pro Gly Lys Ala Thr Glu Val
                 20                  25                  30

Arg Val Thr Val Leu Arg Gln Ala Asp Ser Gln Val Thr Glu Val Cys
             35                  40                  45
```

Ala Ala Thr Phe Thr Glu Lys Asn Thr Val Gly Phe Leu Asp Asp Ser
            50                  55                  60

Ile Cys Thr Gly Thr Phe Asn Glu Ser Arg Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp Gln Glu Pro Lys
             115                 120                 125

Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 52
<211> LENGTH: 357
<212> TYPE: PRT
<213> ORGANISM: Artificial Sequence
<220> FEATURE:
<223> OTHER INFORMATION: Fusion protein

<400> SEQUENCE: 52

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
             35                  40                  45

```
Ala Ala Thr Tyr Met Met Gly Asn Glu Leu Thr Phe Leu Asp Asp Ser
 50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp Gln Glu Pro Lys
            115                 120                 125

Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 53
<211> LENGTH: 357
<212> TYPE: PRT
<213> ORGANISM: Artificial Sequence
<220> FEATURE:
<223> OTHER INFORMATION: Fusion protein

<400> SEQUENCE: 53

Ile Gln Val Thr Gln Pro Ser Val Val Leu Ala Ser Ser Arg Gly Ile
 1               5                  10                  15

Ala Ser Phe Val Cys Glu Tyr Ala Ser Pro Gly Lys Ala Thr Glu Val
                 20                  25                  30

Arg Val Thr Val Leu Arg Gln Ala Asp Ser Gln Val Thr Glu Val Cys
             35                  40                  45
```

```
Ala Ala Thr Phe Thr Glu Lys Asn Thr Val Gly Phe Leu Asp Asp Ser
     50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp Gln Glu Pro Lys
            115                 120                 125

Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 54
<211> LENGTH: 357
<212> TYPE: PRT
<213> ORGANISM: Artificial Sequence
<220> FEATURE:
<223> OTHER INFORMATION: Fusion protein

<400> SEQUENCE: 54

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45
```

Ala Ala Thr Tyr Met Met Gly Asn Glu Leu Thr Phe Leu Asp Asp Ser
 50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 55
<211> LENGTH: 357
<212> TYPE: PRT
<213> ORGANISM: Artificial Sequence
<220> FEATURE:
<223> OTHER INFORMATION: Fusion protein

<400> SEQUENCE: 55

Ile Gln Val Thr Gln Pro Ser Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

```
Ala Ala Thr Phe Thr Glu Lys Asn Thr Val Gly Phe Leu Asp Asp Ser
    50                  55                  60

Ile Cys Thr Gly Thr Phe Asn Glu Ser Arg Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp Gln Glu Pro Lys
            115                 120                 125

Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Tyr Ile Thr Arg Glu Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 56
<211> LENGTH: 357
<212> TYPE: PRT
<213> ORGANISM: Artificial Sequence
<220> FEATURE:
<223> OTHER INFORMATION: Fusion protein

<400> SEQUENCE: 56

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45
```

Ala Ala Thr Tyr Met Met Gly Asn Glu Leu Thr Phe Leu Asp Asp Ser
            50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Phe Glu Gly Met Gly Asn Gly Thr Gln Ile
            100                 105                 110

Tyr Val Ile Asp Pro Glu Pro Cys Pro Asp Ser Asp Gln Glu Pro Lys
            115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
    195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
    275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 57
<211> LENGTH: 125
<212> TYPE: PRT
<213> ORGANISM: Mus musculus

<400> SEQUENCE: 57

Gln Val Gln Leu Lys Glu Ser Gly Pro Gly Leu Val Ala Pro Ser Gln
 1                5                  10                  15

Ser Leu Ser Ile Thr Cys Thr Val Ser Gly Phe Ser Leu Thr Ser Tyr
                20                  25                  30

Gly Leu Ser Trp Val Arg Gln Pro Pro Gly Lys Gly Leu Glu Trp Leu
            35                  40                  45

Gly Val Ile Trp Tyr Asp Gly Asn Thr Asn Phe His Ser Ala Leu Ile
    50                  55                  60

Ser Arg Leu Thr Ile Ser Lys Asp Asn Ser Lys Ser Gln Val Phe Leu
65                  70                  75                  80

Glu Leu Asn Ser Leu Gln Thr Asp Thr Ala Thr Tyr Tyr Cys Ala
            85                  90                  95

Lys Thr Glu Gly His Tyr Tyr Gly Ser Asn Tyr Gly Tyr Ala Leu
            100                 105                 110

Asp Tyr Trp Gly Gln Gly Thr Ser Val Thr Val Ser Ser
        115                 120                 125

<210> SEQ ID NO 58
<211> LENGTH: 25
<212> TYPE: PRT
<213> ORGANISM: Mus musculus

<400> SEQUENCE: 58

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 59
<211> LENGTH: 14
<212> TYPE: PRT
<213> ORGANISM: Mus musculus

<400> SEQUENCE: 59

Trp Ile Arg Gln Pro Pro Gly Lys Gly Leu Glu Trp Ile Gly
1               5                   10

<210> SEQ ID NO 60
<211> LENGTH: 31
<212> TYPE: PRT
<213> ORGANISM: Mus musculus

<400> SEQUENCE: 60

Val Thr Ile Ser Val Asp Thr Ser Lys Asn Gln Phe Ser Leu Lys Leu
1               5                   10                  15

Ser Ser Val Thr Ala Ala Asp Thr Ala Val Tyr Tyr Cys Ala Arg
            20                  25                  30

<210> SEQ ID NO 61
<211> LENGTH: 11
<212> TYPE: PRT
<213> ORGANISM: Mus musculus

<400> SEQUENCE: 61

Trp Gly Gln Gly Thr Leu Val Thr Val Ser Ser
1               5                   10

<210> SEQ ID NO 62
<211> LENGTH: 125
<212> TYPE: PRT
<213> ORGANISM: Artificial Sequence
<220> FEATURE:
<223> OTHER INFORMATION: Humanized

<400> SEQUENCE: 62

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

```
Gly Leu Ser Trp Ile Arg Gln Pro Gly Lys Gly Leu Glu Trp Ile
            35                  40                  45

Gly Tyr Ile Trp Tyr Asp Gly Asn Thr Asn Phe His Pro Ser Leu Lys
 50                  55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Lys Thr Glu Gly His Tyr Tyr Gly Ser Asn Tyr Gly Tyr Tyr Ala Leu
            100                 105                 110

Asp Tyr Trp Gly Gln Gly Thr Ser Val Thr Val Ser Ser
            115                 120                 125
```

<210> SEQ ID NO 63
<211> LENGTH: 125
<212> TYPE: PRT
<213> ORGANISM: Artificial Sequence
<220> FEATURE:
<223> OTHER INFORMATION: Humanized

<400> SEQUENCE: 63

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Tyr
                 20                  25                  30

Gly Leu Ser Trp Ile Arg Gln Pro Gly Lys Gly Leu Glu Trp Ile
            35                  40                  45

Gly Tyr Ile Trp Tyr Asp Gly Asn Thr Asn Phe His Ser Ser Leu Lys
 50                  55                  60

Ser Arg Val Thr Ile Ser Lys Asp Thr Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Thr Glu Gly His Tyr Tyr Gly Ser Asn Tyr Gly Tyr Tyr Ala Leu
            100                 105                 110

Asp Tyr Trp Gly Gln Gly Thr Leu Val Thr Val Ser Ser
            115                 120                 125
```

<210> SEQ ID NO 64
<211> LENGTH: 125
<212> TYPE: PRT
<213> ORGANISM: Artificial Sequenc
<220> FEATURE:
<223> OTHER INFORMATION: Humanized

<400> SEQUENCE: 64

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Tyr
                 20                  25                  30

Gly Leu Ser Trp Ile Arg Gln Pro Gly Lys Gly Leu Glu Trp Ile
            35                  40                  45

Gly Tyr Ile Trp Tyr Asp Gly Asn Thr Asn Phe His Ser Pro Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95
```

```
Lys Thr Glu Gly His Tyr Tyr Gly Ser Asn Tyr Gly Tyr Tyr Ala Leu
                100                 105                 110

Asp Tyr Trp Gly Gln Gly Thr Leu Val Thr Val Ser Ser
            115                 120                 125

<210> SEQ ID NO 65
<211> LENGTH: 107
<212> TYPE: PRT
<213> ORGANISM: Mus musculus

<400> SEQUENCE: 65

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Phe Cys Gln His Leu Trp Gly Thr Pro Tyr
                85                  90                  95

Thr Phe Gly Gly Gly Thr Lys Leu Glu Ile Lys
            100                 105

<210> SEQ ID NO 66
<211> LENGTH: 23
<212> TYPE: PRT
<213> ORGANISM: Mus musculus

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 67
<211> LENGTH: 15
<212> TYPE: PRT
<213> ORGANISM: Mus musculus

<400> SEQUENCE: 67

Trp Tyr Gln Gln Lys Pro Gly Lys Ala Pro Lys Leu Leu Ile Tyr
1               5                   10                  15

<210> SEQ ID NO 68
<211> LENGTH: 32
<212> TYPE: PRT
<213> ORGANISM: Mus musculus

<400> SEQUENCE: 68

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 69
<211> LENGTH: 10
<212> TYPE: PRT
```

<213> ORGANISM: Mus musculus

<400> SEQUENCE: 69

Phe Gly Gln Gly Thr Lys Leu Glu Ile Lys
1               5                   10

<210> SEQ ID NO 70
<211> LENGTH: 107
<212> TYPE: PRT
<213> ORGANISM: Artificial Sequence
<220> FEATURE:
<223> OTHER INFORMATION: Humanized

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Leu
        35                  40                  45

Tyr Ala Ala Thr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Leu Trp Gly Thr Pro Tyr
                85                  90                  95

Thr Phe Gly Gly Gly Thr Lys Leu Glu Ile Lys
            100                 105

<210> SEQ ID NO 71
<211> LENGTH: 107
<212> TYPE: PRT
<213> ORGANISM: Artificial Sequence
<220> FEATURE:
<223> OTHER INFORMATION: Humanized

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Gln Gly Lys Ala Pro Lys Leu Leu Leu
        35                  40                  45

Tyr Ala Ala Thr Asn Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln His Leu Trp Gly Thr Pro Tyr
                85                  90                  95

Thr Phe Gly Gln Gly Thr Lys Leu Glu Ile Lys
            100                 105

<210> SEQ ID NO 72
<211> LENGTH: 107
<212> TYPE: PRT
<213> ORGANISM: Artificial Sequence
<220> FEATURE:
<223> OTHER INFORMATION: Humanized

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Leu Trp Gly Thr Pro Tyr
                85                  90                  95

Thr Phe Gly Gly Gly Thr Lys Val Glu Ile Lys
            100                 105
```

<210> SEQ ID NO 73
<211> LENGTH: 124
<212> TYPE: PRT
<213> ORGANISM: Homo sapiens

<400> SEQUENCE: 73

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120
```

<210> SEQ ID NO 74
<211> LENGTH: 18
<212> TYPE: PRT
<213> ORGANISM: Artificial
<220> FEATURE:
<223> OTHER INFORMATION: Humanized

<400> SEQUENCE: 74

```
Asp Ile Gln Met Thr Gln Ser Pro Ser Ser Leu Ser Ala Ser Val Gly
1               5                   10                  15

Asp Arg
```

<210> SEQ ID NO 75
<211> LENGTH: 23
<212> TYPE: PRT
<213> ORGANISM: Artificial
<220> FEATURE:
<223> OTHER INFORMATION: Humanized

<400> SEQUENCE: 75

Trp Gln Gln Gly Asn Val Phe Ser Cys Ser Val Met His Glu Ala Leu

```
                1               5                  10                  15
His Asn His Tyr Thr Gln Lys
                20

<210> SEQ ID NO 76
<211> LENGTH: 15
<212> TYPE: PRT
<213> ORGANISM: Artificial
<220> FEATURE:
<223> OTHER INFORMATION: Humanized

<400> SEQUENCE: 76

Ala Ser Glu Asn Ile Tyr Ser Asn Leu Ala Trp Tyr Gln Gln Lys
1               5                  10                  15

<210> SEQ ID NO 77
<211> LENGTH: 42
<212> TYPE: PRT
<213> ORGANISM: Artificial
<220> FEATURE:
<223> OTHER INFORMATION: Humanized

<400> SEQUENCE: 77

Phe Ser Gly Ser Gly Ser Gly Thr Asp Tyr Thr Leu Thr Ile Ser Ser
1               5                  10                  15

Leu Gln Pro Glu Asp Phe Ala Thr Tyr Phe Cys Gln His Leu Trp Gly
                20                  25                  30

Thr Pro Tyr Thr Phe Gly Gln Gly Thr Lys
                35                  40

<210> SEQ ID NO 78
<211> LENGTH: 4
<212> TYPE: PRT
<213> ORGANISM: Artificial
<220> FEATURE:
<223> OTHER INFORMATION: Humanized

<400> SEQUENCE: 78

Val Gln Trp Lys
1

<210> SEQ ID NO 79
<211> LENGTH: 38
<212> TYPE: PRT
<213> ORGANISM: Artificial
<220> FEATURE:
<223> OTHER INFORMATION: Humanized

<400> SEQUENCE: 79

Gln Val Gln Leu Gln Glu Ser Gly Pro Gly Leu Val Lys Pro Ser Glu
1               5                  10                  15

Thr Leu Ser Leu Thr Cys Thr Val Ser Gly Phe Ser Leu Thr Ser Tyr
                20                  25                  30

Gly Leu Ser Trp Ile Arg
                35

<210> SEQ ID NO 80
<211> LENGTH: 21
<212> TYPE: PRT
<213> ORGANISM: Artificial
<220> FEATURE:
<223> OTHER INFORMATION: Humanized

<400> SEQUENCE: 80
```

Gly Leu Glu Trp Ile Gly Tyr Ile Trp Tyr Asp Gly Asn Thr Asn Phe
1               5                   10                  15

His Pro Ser Leu Lys
            20

<210> SEQ ID NO 81
<211> LENGTH: 32
<212> TYPE: PRT
<213> ORGANISM: Artificial
<220> FEATURE:
<223> OTHER INFORMATION: Humanized

<400> SEQUENCE: 81

Thr Glu Gly His Tyr Tyr Gly Ser Asn Tyr Gly Tyr Tyr Ala Leu Asp
1               5                   10                  15

Tyr Trp Gly Gln Gly Thr Ser Val Thr Val Ser Ser Ala Ser Thr Lys
                20                  25                  30

<210> SEQ ID NO 82
<211> LENGTH: 63
<212> TYPE: PRT
<213> ORGANISM: Artificial
<220> FEATURE:
<223> OTHER INFORMATION: Humanized

<400> SEQUENCE: 82

Asp Tyr Phe Pro Glu Pro Val Thr Val Ser Trp Asn Ser Gly Ala Leu
1               5                   10                  15

Thr Ser Gly Val His Thr Phe Pro Ala Val Leu Gln Ser Ser Gly Leu
                20                  25                  30

Tyr Ser Leu Ser Ser Val Val Thr Val Pro Ser Ser Ser Leu Gly Thr
            35                  40                  45

Gln Thr Tyr Ile Cys Asn Val Asn His Lys Pro Ser Asn Thr Lys
        50                  55                  60

<210> SEQ ID NO 83
<211> LENGTH: 14
<212> TYPE: PRT
<213> ORGANISM: Artificial
<220> FEATURE:
<223> OTHER INFORMATION: Humanized

<400> SEQUENCE: 83

Phe Asn Trp Tyr Val Asp Gly Val Glu Val His Asn Ala Lys
1               5                   10

<210> SEQ ID NO 84
<211> LENGTH: 16
<212> TYPE: PRT
<213> ORGANISM: Artificial
<220> FEATURE:
<223> OTHER INFORMATION: Humanized

<400> SEQUENCE: 84

Val Val Ser Val Leu Thr Val Leu His Gln Asp Trp Leu Asn Gly Lys
1               5                   10                  15

<210> SEQ ID NO 85
<211> LENGTH: 22
<212> TYPE: PRT
<213> ORGANISM: Artificial
<220> FEATURE:
<223> OTHER INFORMATION: Humanized

<400> SEQUENCE: 85

-continued

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 86
<211> LENGTH: 23
<212> TYPE: PRT
<213> ORGANISM: Artificial
<220> FEATURE:
<223> OTHER INFORMATION: Humanized

<400> SEQUENCE: 86

Trp Gln Gln Gly Asn Val Phe Ser Cys Ser Val Met His Glu Ala Leu
1               5                   10                  15

His Asn His Tyr Thr Gln Lys
            20

<210> SEQ ID NO 87
<211> LENGTH: 21
<212> TYPE: PRT
<213> ORGANISM: Artificial
<220> FEATURE:
<223> OTHER INFORMATION: Humanized

<400> SEQUENCE: 87

Gly Leu Glu Trp Ile Gly Tyr Ile Trp Tyr Asp Gly Asn Thr Asn Phe
1               5                   10                  15

His Ser Pro Leu Lys
            20

<210> SEQ ID NO 88
<211> LENGTH: 32
<212> TYPE: PRT
<213> ORGANISM: Artificial
<220> FEATURE:
<223> OTHER INFORMATION: Humanized

<400> SEQUENCE: 88

Thr Glu Gly His Tyr Tyr Gly Ser Asn Tyr Gly Tyr Tyr Ala Leu Asp
1               5                   10                  15

Tyr Trp Gly Gln Gly Thr Leu Val Thr Val Ser Ser Ala Ser Thr Lys
            20                  25                  30

<210> SEQ ID NO 89
<211> LENGTH: 18
<212> TYPE: PRT
<213> ORGANISM: Artificial
<220> FEATURE:
<223> OTHER INFORMATION: Humanized

<400> SEQUENCE: 89

Ala Ser Glu Asn Ile Tyr Ser Asn Leu Ala Trp Tyr Gln Gln Lys Pro
1               5                   10                  15

Gly Lys

<210> SEQ ID NO 90
<211> LENGTH: 42
<212> TYPE: PRT
<213> ORGANISM: Artificial
<220> FEATURE:
<223> OTHER INFORMATION: Humanized

<400> SEQUENCE: 90

```
Phe Ser Gly Ser Gly Ser Gly Thr Asp Phe Thr Leu Thr Ile Ser Ser
1               5                   10                  15

Leu Gln Pro Glu Asp Phe Ala Thr Tyr Tyr Cys Gln His Leu Trp Gly
            20                  25                  30

Thr Pro Tyr Thr Phe Gly Gly Gly Thr Lys
        35                  40
```

CHIMERIC AND HUMANIZED ANTI-HUMAN CTLA4 MONOCLONAL ANTIBODIES AND USES THEREOF

FIELD OF THE INVENTION

This invention relates to chimeric and humanized antibodies that bind to the human CTLA4 molecule and to methods of their use.

BACKGROUND OF THE INVENTION

The immune system of humans and other mammals is responsible for providing protection against infection and disease. Such protection is provided both by a humoral immune response and by a cell-mediated immune response. The humoral response results in the production of antibodies and other biomolecules that are capable of recognizing and neutralizing foreign targets (antigens). In contrast, the cell-mediated immune response involves the activation of macrophages, neutrophil, natural killer cells (NK), and antigen-specific cytotoxic T-lymphocytes by T cells, and the release of various cytokines in response to the recognition of an antigen.

The ability of T cells to optimally mediate an immune response against an antigen requires two distinct signaling interactions. First, antigen that has been arrayed on the surface of antigen-presenting cells (APC) must be presented to an antigen-specific naive T cells in the form of MHC: peptide complex (1, 2). Such presentation delivers a signal via the T cell receptor (TCR) that directs the T cell to initiate an immune response that will be specific to the presented antigen. Second, a series of co-stimulatory signals, mediated through interactions between the APC and distinct T cell surface molecules, triggers first the activation and proliferation of the T cells and ultimately their inhibition (3-5). Thus, the first signal confers specificity to the immune response whereas the second signal serves to determine the nature, magnitude and duration of the response while limiting immunity to self. Of particular importance among these second signal molecules is binding between the B7.1 (CD80) (6) and B7.2 (CD86) (7-9) ligands of the Antigen Presenting Cell and the CD28 and CTLA4 receptors (10-12) of the T-lymphocyte.

Cytotoxic T lymphocyte antigen-4 (CTLA4) is recognized as a key regulators of adaptive immune responses, having a central role in the maintenance of peripheral tolerance and in shaping the repertoire of emergent T cell responses and, therefore, a therapeutic target for the treatment of cancer and inflammation. Treatment with anti-CTLA4 antibodies has been shown to be a powerful tool for enhancing anti-tumor immunity in preclinical models (10). Monotherapy with an antibody against CTLA4 promoted rejection of transplantable tumors of various origins.

Based on promising preclinical tumor model studies, the clinical potential of antibodies against CTLA4 has been explored in different human malignancies. Although anti-CTLA4 (Ipilimumab, marketed as Yervoy) has demonstrated efficacy in treating melanoma, treatment and targeting of CTLA4 is associated with autoimmune like toxicities. Characteristic side effects from inhibition of CTLA4 are generally called immune-related adverse events (irAEs) and the most common irAEs are skin rash, hepatitis, colitis and endocrinopathies, particularly hypopituitarism. Therefore, there is a desire to improve the therapeutic potential of anti-CTLA4 antibodies by increasing efficacy while reducing the associated irAEs.

Another focus for the field of immunotherapy and the treatment of tumors, is the combination of different immune check inhibitors in order to enhance anti-tumor activity, particularly against poorly immunogenic tumors. However, this approach is associated with the risk of further increasing the autoimmune side effects further highlighting the need to selectively modulate cancer immunity without enhancing autoimmunity.

Further investigations into the ligands of the CD28 receptor have led to the identification and characterization of a set of related B7 molecules (the "B7 Superfamily") (32-33). There are currently several known members of the family: B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (35-36). B7-H1 is broadly expressed in different human and mouse tissues, such as heart, placenta, muscle, fetal liver, spleen, lymph nodes, and thymus for both species as well as liver, lung, and kidney in mouse only (37). B7-H1 (PD-L1, CD274) is a particularly significant member of the B7 Superfamily as it is pivotally involved in shaping the immune response to tumors (38; U.S. Pat. Nos. 6,803,192; 7,794,710; United States Patent Application Publication Nos. 2005/0059051; 2009/0055944; 2009/0274666; 2009/0313687; PCT Publication No. WO 01/39722; WO 02/086083).

Programmed Death-1 ("PD-1") is a receptor of B7-H1 as well as B7-DC. PD-1 is a type I membrane protein member of the extended CD28/CTLA4 family of T cell regulators (39; United States Patent Application Publication No. 2007/0202100; 2008/0311117; 2009/00110667; U.S. Pat. Nos. 6,808,710; 7,101,550; 7,488,802; 7,635,757; 7,722,868; PCT Publication No. WO 01/14557). Compared to CTLA4, PD-1 more broadly negatively regulates immune responses. PD-1 is expressed on activated T cells, B cells, and monocytes (40-41) and at low levels in natural killer (NK) T cells (42-43).

Interaction of B7-H1 and PD-1 has been found to provide a crucial negative co-stimulatory signal to T and B cells (43) and functions as a cell death inducer (39). The role of B7-H1 and PD-1 in inhibiting T cell activation and proliferation has suggested that these biomolecules might serve as therapeutic targets for treatments of inflammation and cancer. Consequently, the use of anti-PD1 and anti-B7-H1 antibodies to treat infections and tumors and up-modulate an adaptive immune response has been proposed and demonstrated to be effective for the treatment of a number of human tumors. However, not all subjects respond or have complete responses to anti-PD-1 or anti-B7-H1 treatment and so there is a strong interest in combining anti-PD-1 or anti-B7-H1 antibodies with other immune check inhibitors in order to enhance anti-tumor activity.

4-1BB (also known as CD137 and TNFRSF9) is another immune checkpoint molecule. The best characterized activity of CD137 is its costimulatory activity for activated T cells. Crosslinking of CD137 enhances T cell proliferation, IL-2 secretion, survival and cytolytic activity. Further, like anti-CTLA4, anti-4-1 BB antibodies can enhance immune activity to eliminate tumors in mice (27-29). However, unlike the tendency of anti-CTLA4 antibodies to exacerbate autoimmune diseases, cancer therapeutic anti-4-1 BB mAbs have been shown to abrogate the development of autoimmune diseases in lupus prone mice, in which they inhibited anti-dsDNA antibody production and reduced the renal pathology (25, 26). Previously data have demonstrated that it is possible to reduce the autoimmune side effects of anti-CTLA4 treatment in a mouse colon cancer tumor model by combining treatment of anti-CTLA4 with anti-4-1 BB antibody, while enhancing the anti-tumor activity (19). This demonstrates that it is possible to offset the autoimmune side effects of anti-CTLA4 tumor therapy.

Preclinical screening of anti-human CTLA4 antibodies is fraught with difficulty because in vitro immunological correlates are sometimes of little value, as demonstrated by experience with anti-mouse CTLA4 antibodies. The same anti-mouse CTLA4 antibodies that induce potent anti-tumor immunity in vivo can have variable effects on T cells in vitro. Anti-CTLA4 antibodies enhanced T cell proliferation in response to alloantigen, but suppressed T cell proliferation in response to costimulation by anti-CD 28 (30, 31). Also, CTLA4 engagement with antibody could either promote or inhibit proliferation of different subsets of T cells in the same culture (32). This complication can be overcome if one can study human T cell responses in a rodent model.

Described herein are anti-CTLA4 antibodies with reduced autoimmune side effects when used to enhance immune responses and for use in anti-tumor therapy. Furthermore, these antibodies can be used in combination with other checkpoint inhibitors, such as anti-PD-1 and anti-4-1 BB, to enhance anti-tumor while abrogating autoimmune side effects.

SUMMARY OF THE INVENTION

This invention relates to antibody compositions and their antigen-binding fragments that bind to the human CTLA4 molecule and their use for cancer immunotherapy with reduced autoimmune side effects. Specifically, the invention relates to antibodies with enhanced CTLA4 blocking activity for CTLA4 ligands B7.1 and B7.2, enhanced effector function, or reduced binding to soluble CTLA4 relative to membrane bound or immobilized CTLA4.

The antibody may comprise a light chain variable amino acid sequence having the amino acid sequence comprising a light chain variable amino acid sequence having the amino acid sequence set forth in SEQ ID NO: 1, and a heavy chain variable amino acid sequence having the amino acid sequence set forth in SEQ ID NO: 2. The antibody may also comprise a heavy chain variable amino acid sequence having the amino acid sequence set forth in SEQ ID NO: 27, 28 or 29, and a light chain variable amino acid sequence having the amino acid sequence set forth in SEQ ID NO: 30, 31 or 32. The antibody may comprise a light chain variable region having CDR sequences set forth in SEQ ID NOS: 21, 22 and 23, and a heavy chain variable region having CDR sequences set forth in SEQ ID NOS: 24, 25 and 26. More specifically, the antibody may comprise a heavy chain variable region having a CDR2 sequence set forth in SEQ ID NO: 33, 34 or 35, and a light chain variable region having CDR sequences set forth in SEQ ID NO: 36, 37 or 38.

The immunoglobulin heavy chain constant regions of the antibody may comprise the amino acid sequence set forth in SEQ ID NO: 3 or 4. The immunoglobulin heavy chain constant region of the antibody may also comprise a mutation. Relative to the sequence of the hIgG1 backbone in SEQ ID NO: 3, the mutation may be M135Y, S137T, T139E, S181A, E216A, or K217A, or a combination thereof. Preferably, the immunoglobulin heavy chain constant region of the antibody may comprise all six mutations. The antibody may comprise a heavy chain amino acid sequence having the amino acid sequence set forth in SEQ ID NO: 6, and a light chain amino acid sequence having the amino acid sequence set forth in SEQ ID NO: 8. The antibody may also comprise a heavy chain amino acid sequence having the amino acid sequence set forth in SEQ ID NO: 9, 11 or 13, and a light chain amino acid sequence having the amino acid sequence set forth in SEQ ID NO: 15, 17 or 19. The antibody may be capable of binding human CTLA4. The antibody may also inhibit binding of human CTLA4 to B7-1 or B7-2.

Further provided herein is an antigen binding fragment of the antibodies described herein.

Also provided herein is a pharmaceutical composition comprising a therapeutically effective amount of the antibodies described herein. The pharmaceutical composition may comprise a physiologically acceptable carrier or excipient.

In another aspect, presented herein are methods for enhancing one or more immune functions or responses in a subject, comprising administering to a subject in need thereof the anti-CTLA4 antibody compositions and pharmaceutical compositions described herein. In a specific embodiment, presented herein are methods for preventing, treating, and/or managing a disease in which it is desirable to activate or enhance one or more immune functions or responses. The disease may be a cancer, which may be a human malignancy. In particular, the human malignancy may be melanoma, lung cancer, breast cancer, hepatocellular carcinoma, ovarian carcinoma, prostate carcinoma, Hodgkin's or non-Hodgkin's lymphoma, acute myelogenic leukemia, chronic myelogenic leukemia, acute lymphocytic leukemia, chronic lymphocytic leukemia, or renal cell carcinoma. In another embodiment, the disease to be treated is an infectious disease. The method described herein may minimize autoimmune adverse effects associated with immunotherapy.

In other specific embodiments, the method comprises combination therapy, wherein the anti-CTLA4 antibody compositions described herein are administered to a subject in combination with another therapy, which may activate or enhance one or more immune functions or responses. In another embodiment, the anti-CTLA4 antibody compositions described herein are administered as an adjuvant in combination with an antigenic composition. In a particular embodiment, the anti-CTLA4 antibody compositions described herein are administered in combination with a vaccine composition to induce or activate or enhance the immune response elicited by the vaccine composition.

In a specific embodiment, the anti-CTLA4 antibody compositions described herein are administered to a subject in combination with one or more other therapies that target different immunomodulatory pathways. In a preferred embodiment, the activity of the therapy targeting a different immunomodulatory pathway is complementary or synergistic with the anti-CTLA4 antibody compositions described herein. In one instance, the anti-CTLA4 antibody compositions described herein are administered in combination with other checkpoint inhibitors or small oncoimmunological modulators such as indoleamine 2,3-dioxygenase (IDO) inhibitors. In another instance, the anti-CTLA4 antibody compositions described herein are administered in combination with immune stimulating molecules. Specific embodiments include combining the anti-CTLA4 antibody compositions described herein with anti-PD-1 (pembrolizumab (Keytruda) or Nivolumab (Opdivo)), anti-B7-H1 (atezolizumab (Tecentriq) or durvalumab), anti-B7-H3, anti-B7-H4, anti-LAG3, anti-Tim3, anti-CD40, anti-OX40, anti-BTLA, anti-CD27, anti-ICOS or anti-41BB. In another embodiment, the anti-CTLA4 antibody compositions described herein and the second immune stimulating molecule are combined in a single bi-specific antibody.

In another embodiment, an anti-human CTLA4 antibody described herein may preferentially bind to human CTLA-4 expressed on the cell surface relative to soluble CTLA4 molecules. The anti-human CTLA4 antibody may bind to human CTLA-4 and preferentially upregulate the expression of B7.1 or B7.2 in vivo. The antibody may be contained in a composition for use in modulating immune responses (immunotherapy) and the treatment of cancer.

The invention further concerns the method of screening for anti-human CTLA4 mAbs with preferred activity. Preclinical screening for anti-human CTLA4 mAbs is fraught with difficulty because in vitro immunological correlates for cancer immunity and autoimmune adverse effect are not defined. Significant autoimmune side-effects have been observed in clinical trials with human anti-CTLA4 (Ipilimumab), especially when combined with anti-PD-1. In order to identify anti-CTLA4 antibodies with reduced immune related toxicities, antibodies demonstrating anti-tumor activity in humanized mice can be screened for their ability to reduce autoimmune adverse effects in vivo using human CTLA4 gene knock-in mice.

In another embodiment, the invention concerns a method of screening for anti-human CTLA4 mAbs with enhanced anti-tumor effect wherein the antibodies demonstrate enhanced local depletion of Treg cells in the tumor environment.

In yet another embodiment, the invention concerns methods of monitoring the blocking effects of anti-CTLA4 antibodies in vivo by monitoring the expression levels of B7.1 and B7.2 on immune cells such as antigen presenting cells (APCs). The invention further contemplates biomarkers for measuring the biological activity of anti-CTLA4 antibodies in vivo and monitoring patent responses to anti-CTLA4 treatment by measuring the level B7.1 and B7.2 expression on immune cells ex vivo.

In order to map the CTLA4 binding epitope of the L3D10 parent antibody and the humanized variants, PP4631 and PP4637, the fact that the mouse and human CTLA4 proteins are cross-reactive to B7-1, but not to the anti-CTLA-4 antibodies was exploited. Accordingly, a number of mutants of the human CTLA-4Fc protein were designed in which clusters of amino acids from the human CTLA-4 protein were replaced with amino acids from the murine Ctla-4 protein. As the anti-CTLA-4 antibodies used in this study do not bind to murine Ctla-4, binding of the anti-human CTLA-4 antibodies can be abolished when key residues of the antibody binding epitope are replaced with murine amino acids.

Figure 10:
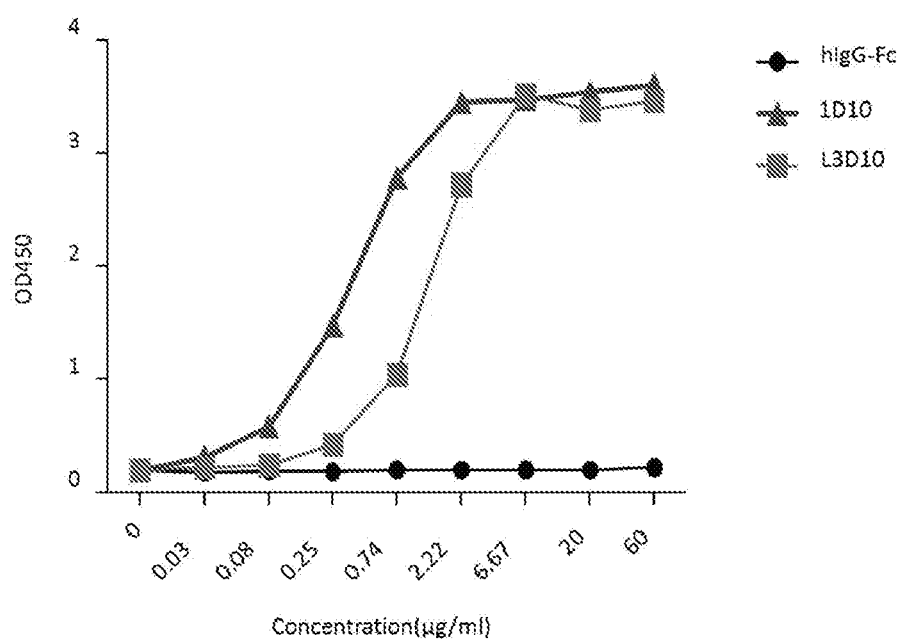

FIG. 10. 10D1 binds to biotinylated human CTLA4-Fc better than L3D10. Varying doses of anti-human CTLA4 mAbs or control IgG were coated onto the plate. Biotinylated CTLA4-Fc was added at 0.25 µg/ml. The amounts of CTLA4 bound to plates were measured using HRP-conjugated streptavidin. Data shown are means of duplicates and are representative of two independent experiments.

Figure 11:
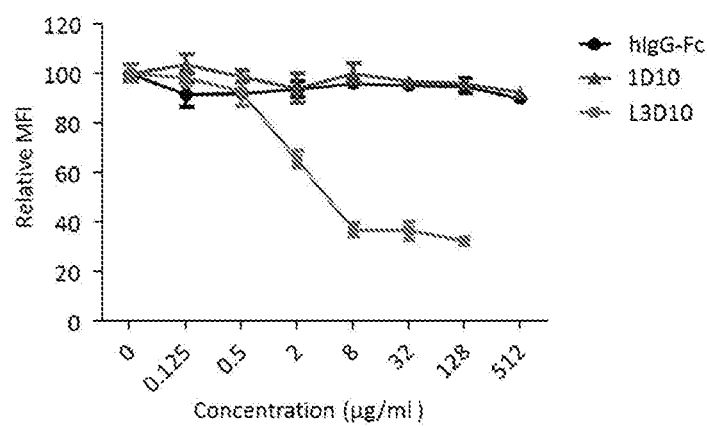

FIG. 11. L3D10 but not 10D1 blocks the interaction between polyhistindine tagged CTLA4 and CHO cells expressing human B7-1. CHO cells expressing human B7-1 were incubated with polyhistidine-tagged CTLA4 along with given doses of antibodies, the amounts of CTLA4-Fc were detected with PE-streptavidin and measured by FACSCanto II. Data shown are means fluorescence intensity of triplicate samples and are representative of two independent experiments.

Figure 12:
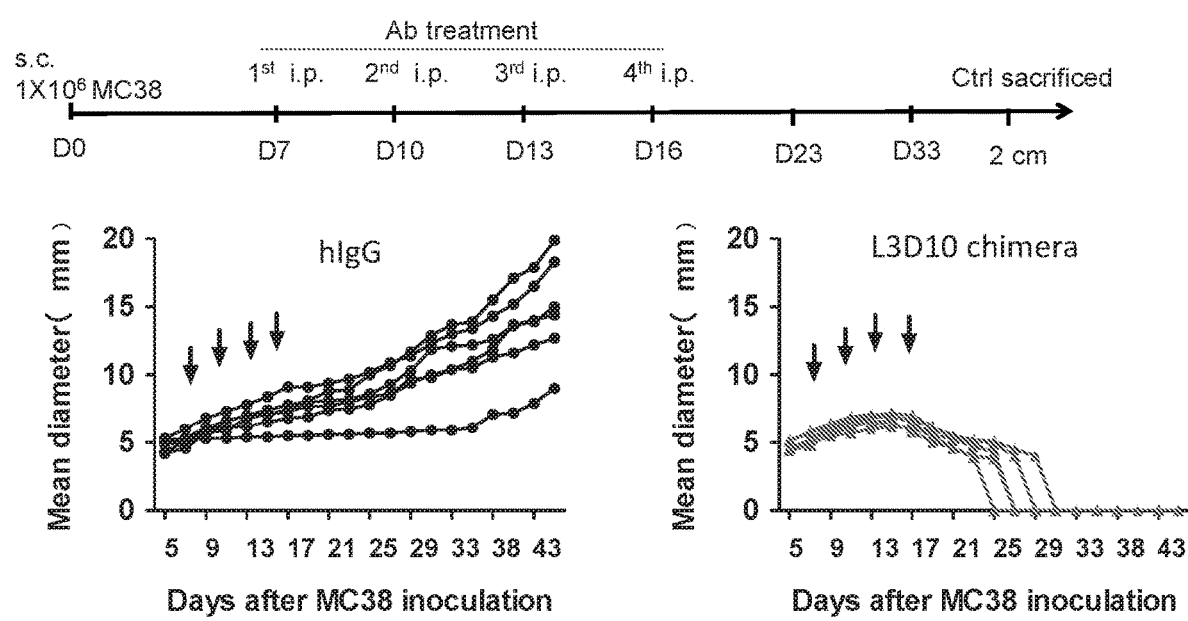

FIG. 12. Chimeric L3D10 induces complete remission of established tumors in the syngeneic MC38 model. Top panel depicts experimental design and the lower panels show growth kinetics of MC38 tumors in mice that received either control IgG (lower left panel, n=6) or chimeric L3D10 (lower right panel, n=5).

Figure 13:
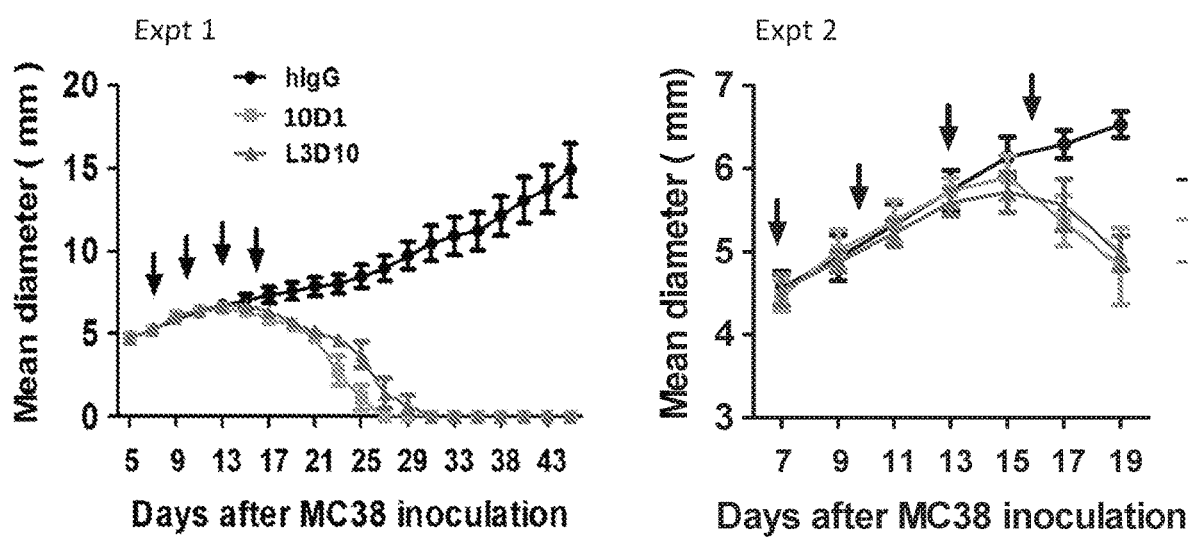

FIG. 13. Therapeutic effect of chimeric L3D10 and 10D1 in the MC38 tumor model. Human CTLA4-knock-in mice with body weight of approximately 20 grams were used for the study. $1\times10^6$ MC38 tumor cells were injected subcutaneously into Ctla4$^{h/h}$ mice and when the tumor reached a size of 0.5 cm in diameter, tumor bearing mice were randomized into three groups with 5 or 6 mice each. Mice were then treated (i.p.) with 100 g/injection of 10D1, chimeric L3D10 or control hIgGFc on days 7, 10, 13, and 16 as indicated by the arrows. The results of duplicate expts are shown (left and right panels) and data shown are means and S.D. of tumor size (n=6 per group in the left panel, n=5 per group in the right panel). L3D10 and 10D1 have similar therapeutic effect in this model and are both able to induce complete remission of established tumors. The diameters (d) of the tumor were calculated using the following formula: D=√(ab), V=ab2/2, where a is the long diameter, while b is the short diameter. Statistical analyses were performed by two-way repeated measures ANOVA (treatment×time). For the left panel: P=10D1 vs. hIgGFc: 5.71e-07; L3D10 vs. hIgGFc: P=5.53e-07; 10D1 vs. L3D10: P=0.869.

Figure 14:
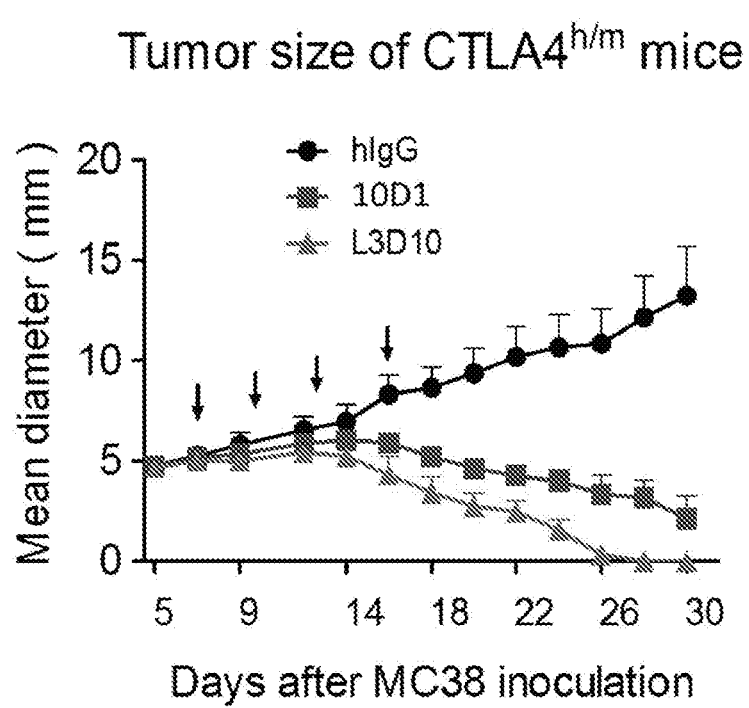

FIG. 14. Effective rejection of MC38 by anti-CTLA-4 mAbs in CTLA4$^{h/m}$ mice. As in FIG. 13, except that heterozygous CTLA4$^{h/m}$ mice are used. Data shown are means and SEM of tumor diameters (6 mice per group); 10D1 vs. hIgGFc: P=0.0011; L3D10 vs. hIgGFc: P=5.55e-05; 10D1 vs. L3D10: P=0.0346.

Figure 15:
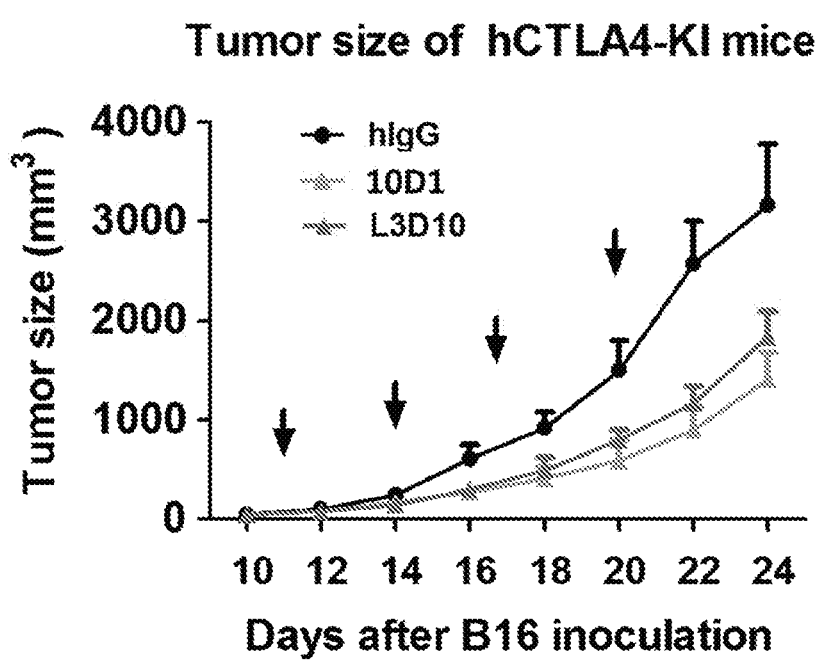

FIG. 15. Therapeutic effect of chimeric L3D10 and 10D1 in the B16-F1 melanoma tumor model. Human CTLA4-knockin mice with body weight of approximately 20 grams were used for the study. Arrows indicate the time of treatment (50 µg/mice/treatment). Data shown are means and S.D. of the tumor size (n=4 per group). L3D10 have similar therapeutic effect in this model and are both able to delay tumor growth in this aggressive and poorly immunogenic tumor model.

Figure 16:
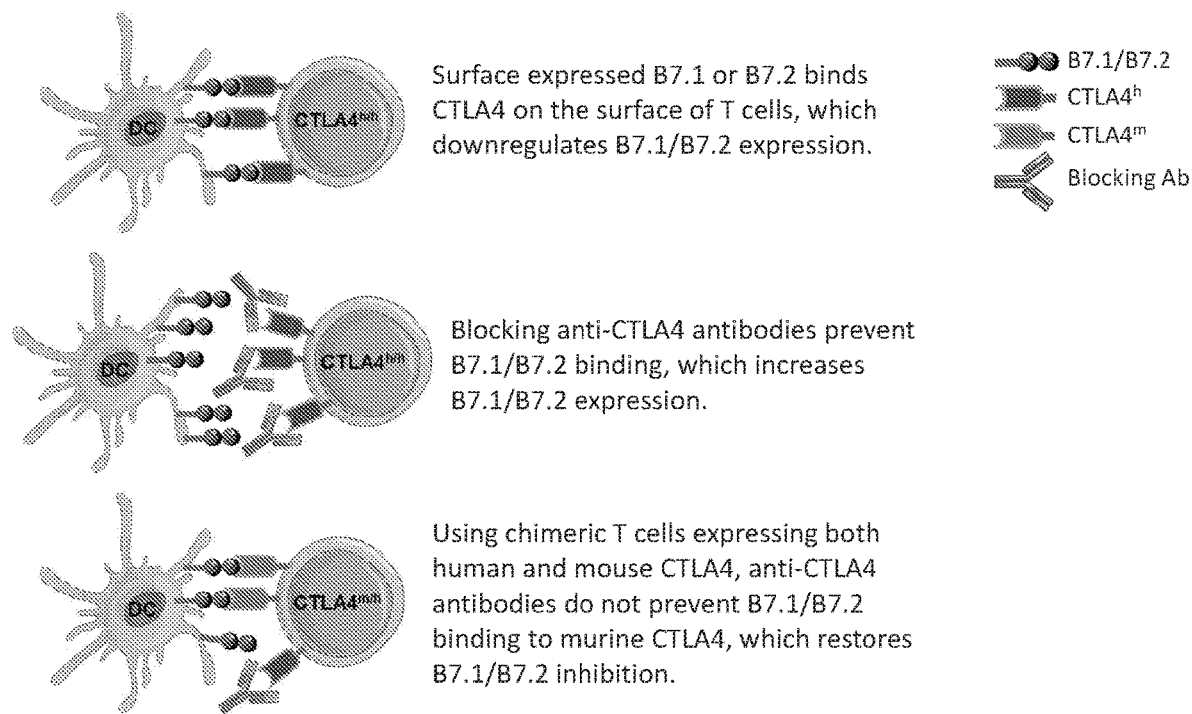

FIG. 16. Assay for measuring CTLA4 blocking in vivo. B7.1 or B7.2 binds on dendritic cells bind to, and are down-regulated by, CTLA4 on surface of T cells. However, binding of blocking anti-CTLA4 antibodies prevents B7.1/B7.2 binding to CTLA4 and thus prevents the downregulation of B7.1 and B7.2, resulting in a net increase in B7.1/B7.2 expression. However, with chimeric T cells expressing both human and mouse CTLA4, antibodies that bind human CTLA4 do not prevent B7.1/B7.2 binding to the murine CTLA4, which restores B7.1/B7.2 inhibition.

Figure 17:
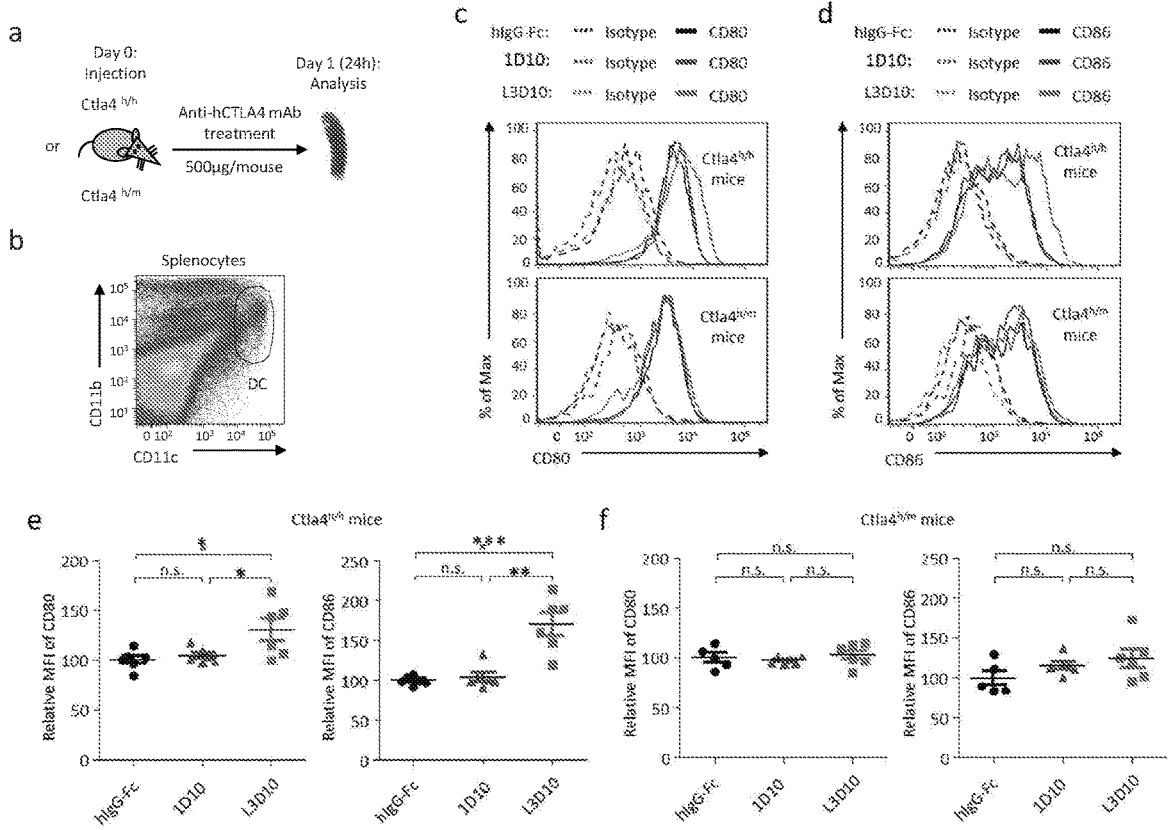

FIGS. 17A-F. 10D1 does not block B7-CTLA4 interaction in vivo. Using the assay described in FIG. 11, cells from mice treated with anti-CTLA4 antibodies were used to assay B7.1 and B7.2 expression. FIG. 17A shows a diagram of experimental design. Briefly, age and gender-matched mice received 500 µg of antibodies or their controls intraperitoneally. At 24 hours after injection, mice were sacrificed and their spleen cells were stained with anti-CD11c, CD11b, anti-B7-1 and anti-B7-2 mAbs. FIG. 17B shows representative data showing the phenotype of CD11c$^{hi}$ DC analyzed for B7 expression. FIG. 17C shows representative histograms depicting the levels of B7-1 on DC from mice that received control IgG1-Fc, L3D10 or 10D1. Data in the top panel shown antibody effect in homozygous knockin mice, while that in the bottom panel show antibody effect in the heterozygous mice. FIG. 17D shows as in FIG. 17C, except that expression of B7-2 is shown. Data shown in FIGS. 17C and D are representative of those from 3 mice per group and have been repeated once with three mice per group. FIG. 17E shows that in human CTLA4 homozygous mice, L3D10 but not 10D1 induced expression of B7-1 (left panel) and B7-2 (right panel). Data shown are summarized from two experiments involving a total of 6 mice per group. In each experiment, the mean data in the control mice is artificially defined as 100% and those in experimental groups are normalized against the control. FIG. 17F as in FIG. 17E, except that heterozygous mice are used. Neither L3D10 nor 10D1 block B7-CTLA4 interaction in mice that co-dominantly express both mouse and human Ctla4 genes.

Figure 18:
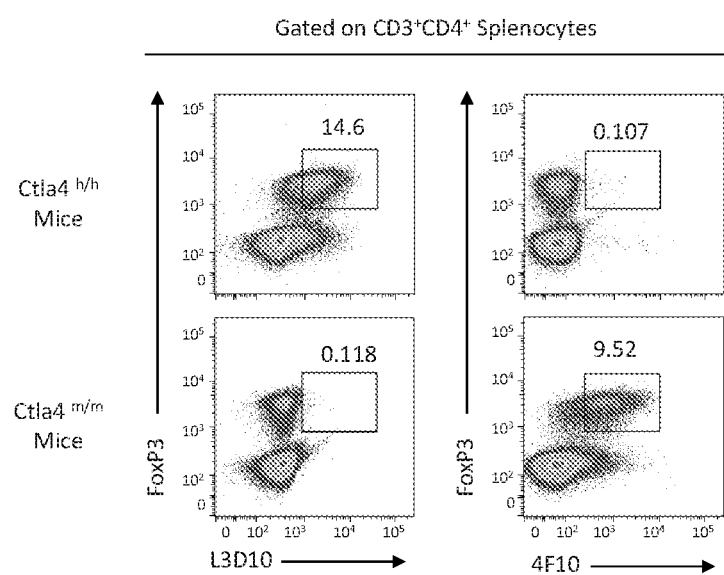

FIG. 18. L3D10 binds to human but not mouse CTLA4. Data showing are dot plots of intracellular staining of CTLA4 among gated Cd3$^+$Cd4$^+$ cells, using spleen cells from Ctla3$^{h/h}$ (top) or Ctla4$^{m/m}$ (bottom) mice. Anti-mouse CTLA4 mAb 4F10 was used as control.

Figure 19:
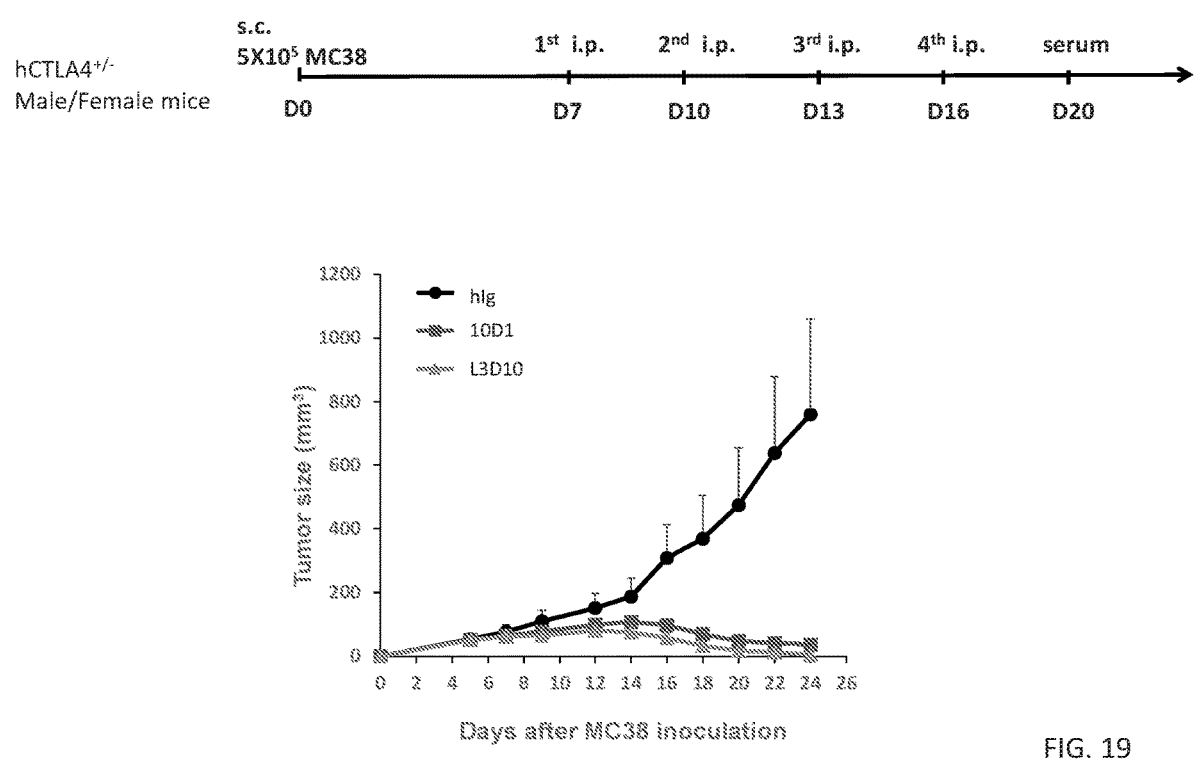

FIG. 19. Therapeutic effect of chimeric L3D10 and 10D1 in CTLA4$^{h/m}$ mice. The top panel depicts the experimental design. The Ctla4$^{h/h}$ mice were challenged with colon cancer cell line MC38 and when the tumor reached a size of approximately 5 mm in diameter, the mice were treated 4 times with control human IgG-Fc, L3D10 or 10D1 and observed tumor size over a 6 weeks period. The lower panels shows the growth kinetics of MC38 tumors in mice that received either control IgG, chimeric L3D10 or 10D1 (n=6 per group). Despite apparent differences in CTLA4 blocking activity in vivo as shown in FIG. 16, both L3D10 and 10D1 display strong anti-tumor activity against the MC38 model in chimeric CTLA4$^{m/h}$ mice.

FIGS. 20A-B. 10D1 and L3D10 have similar therapeutic effect on B16 melanoma growth. $1\times10^5$ B16 tumor cells were injected (s.c.) into Ctla4$^{h/h}$ mice (n=4-5), and treated (i.p.) with 100 ⎯g (FIG. 20A) or 250 ⎯g (FIG. 20B) 10D1, L3D10 or control IgGFc on day 11, 14, 17 (FIG. 20A) or on day 2, 5, and 8 (FIG. 20B), as indicated by arrows. For FIG. 20A, 10D1 vs. hIgGFc: P=0.0265; L3D10 vs. hIgGFc: 10D1 vs. L3D10: P=0.0487; P=0.302. For FIG. 20B, 10D1 vs. hIgGFc: P=0.00616; L3D10 vs. hIgGFc: P=0.0269: 10D1 vs. L3D10: P=0.370. Data represent mean±SEM of 4-5 mice per group. Statistical analyses were performed by two-way repeated measures ANOVA.

Figure 21:
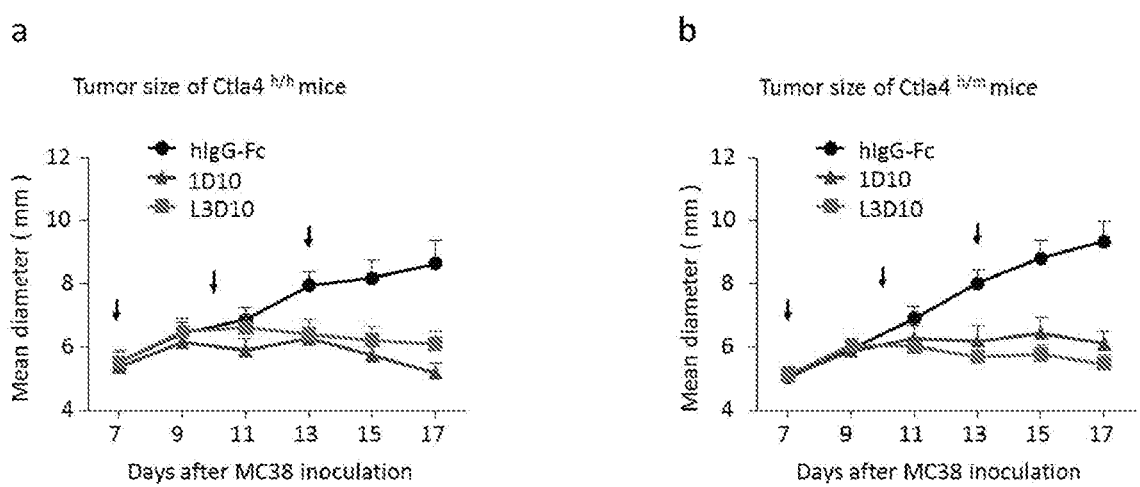

FIGS. 21A-B. Immunotherapeutic effects between L3D10 and 10D1 in Ctla4$^{h/h}$ (FIG. 21A) and Ctla4$^{m/h}$ (FIG. 21B) in mice that were terminated before rejection in complete in order to evaluate depletion of Treg within tumor microenvironment. Data shown are means and SEM of tumor diameters of two independent experiments, involving 5 mice per group.

Figure 22:
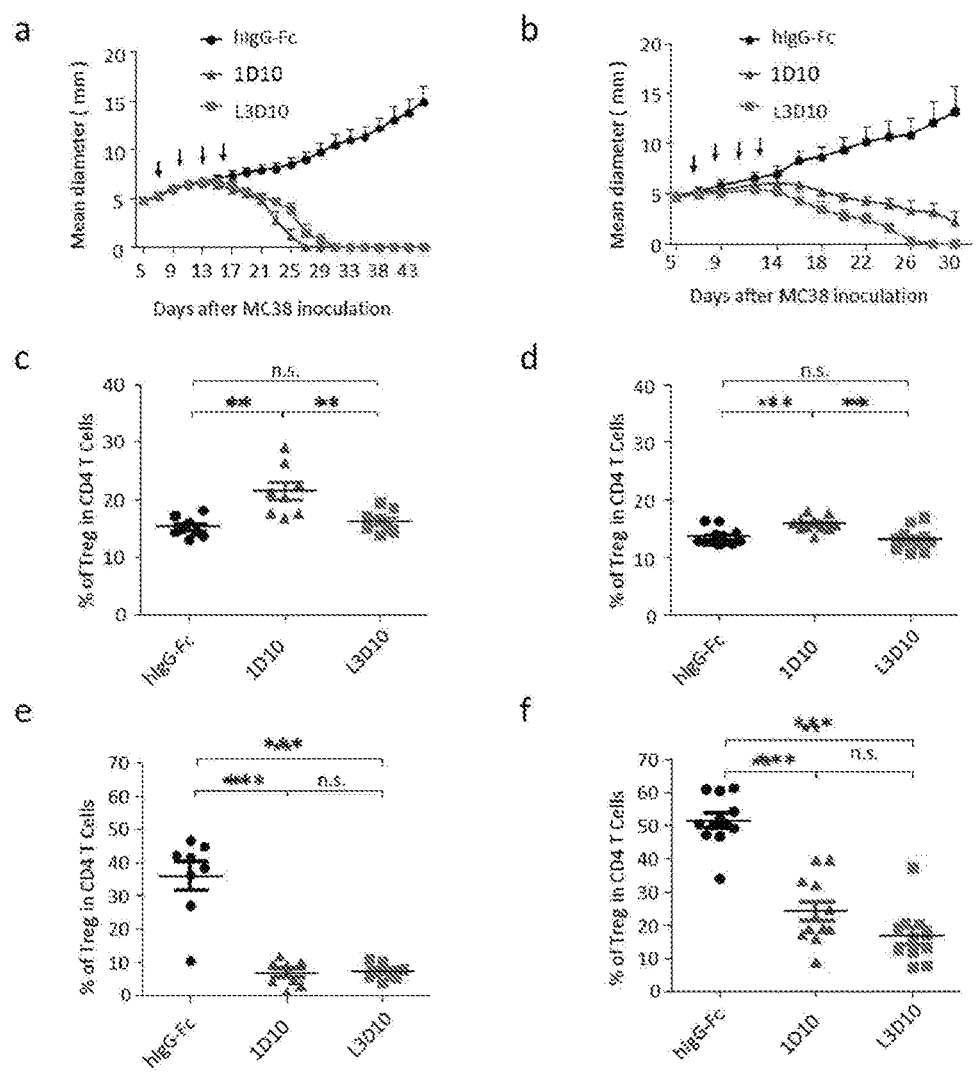

FIGS. 22A-F. Blocking the B7-CTLA4 interaction does not contribute to cancer immunotherapeutic activity of anti-CTLA4 mAb. FIG. 22A shows comparable immunotherapeutic effect despite vastly different blocking activity by two anti-CTLA4 mAbs. $5 \times 10^5$ MC38 tumor cells were injected (s.c.) into Ctla4$^{h/h}$ mice (n=6), and treated (i.p.) with 100 g 10D1, L3D10 or control hIgG-Fc on days 7, 10, 13, and 16, as indicated by arrows. Data represent mean±SEM of six mice per group. Statistical analyses were performed by two-way repeated measures ANOVA (treatment×time). 10D1 vs. hIgG-Fc: P=5.71$^{e-07}$; L3D10 vs. hIgG-Fc: P=5.53e$^{-07}$; 10D1 vs. L3D10: P=0.869. Data are representative of three independent experiments. FIG. 22B. In mice that neither antibodies block B7-CTLA4 interaction, both induce robust tumor rejection. As in FIG. 22A, except that heterozygous mice that express both mouse and human CTLA4 were used. 10D1 vs. hIgG-Fc: P=0.0011; L3D10 vs. hIgG-Fc: P=5.55e$^5$; 10D1 vs. L3D10: P=0.0346. Data are representative of three independent experiments. FIGS. 22C-F, Blocking B7-CTLA4 interaction does not contribute to selective depletion of Treg in tumor microenvironment. FIGS. 22C and D. Regardless of their ability to block B7-CTLA4 interaction, L3D10 and 10D1 do not delete Treg in the spleen. Data shown are % of Foxp3+ cells among spleen CD4 T cells in Ctla4$^{h/h}$ (FIG. 22C) and Ctla4$^{m/h}$ (FIG. 22D) mice. n=6. e and f, both L3D10 and 10D1 delete Treg among tumor infiltrating CD4 T cells in Ctla4$^{h/h}$ (FIG. 22E) and Ctla4$^{m/h}$ (FIG. 22F) mice. Data shown in c-f are % of Treg at 17 (experiment 1) or 19 days (experiment 2) after tumor cell challenge and 10 or 12 days after initiation of 4 anti-CTLA4 mAb treatments as indicated in arrows.

Figure 23:
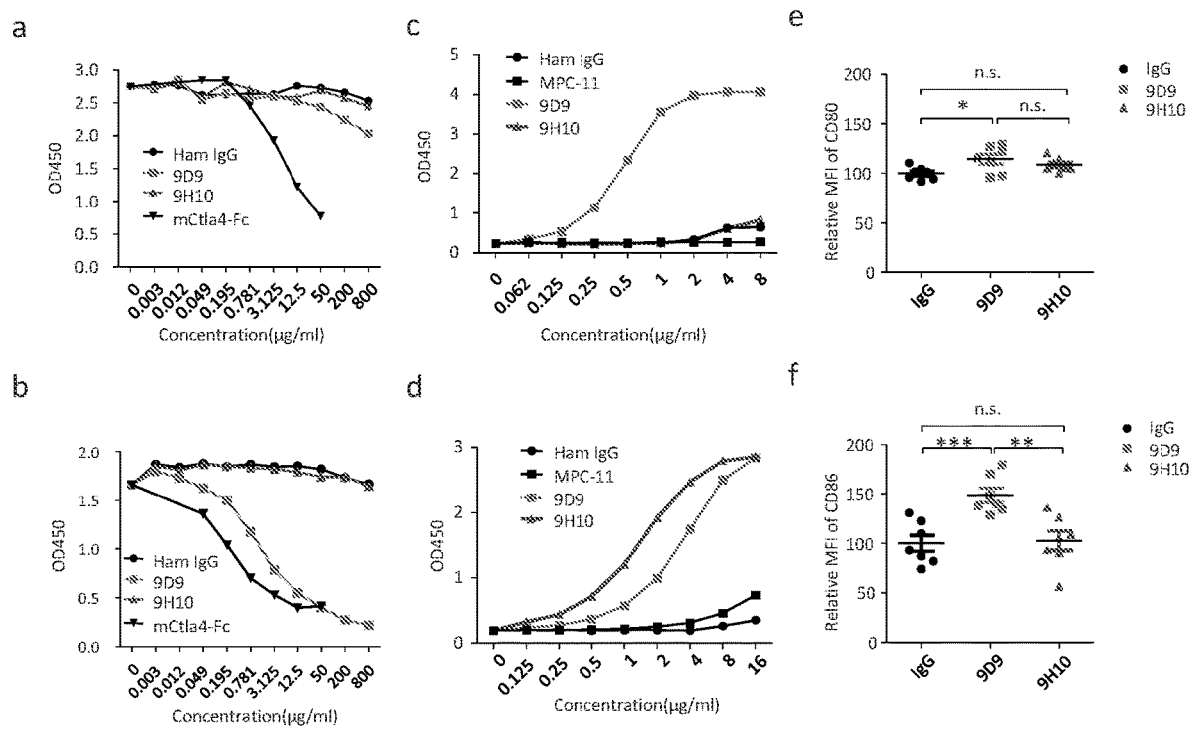

FIGS. 23A-F. Evaluation of blocking activities of commonly used anti-mouse CTLA4 mAbs 9H10 and 9D9. FIGS. 23A and B show that 9H10 does not block B7-CTLA4 interaction if B7-1 (FIG. 23A) and B7-2 (FIG. 23B) are coated onto plates. Biotinylated mouse CTLA4-Fc fusion protein were incubated with B7-coated plates in the presence of given concentration of control IgG or anti-mouse CTLA4 mAb 9D9 and 9H10. The CTLA4 binding is detected with HRP-conjugated streptavidin. Data shown are means of duplicated and are representative of two independent experiments. FIGS. 23C and D show that 9D9 and 9H10 exhibit differential binding to soluble (FIG. 23C) and plate bound CTLA4-Fc (FIG. 23D). Data shown are means of duplicated and are representative of at least two independent experiments. FIGS. 23E and F show the effects of anti-mouse CTLA4 mAbs 9D9 and 9H10 on levels of B7-1 (FIG. 23E) and B7-2 (FIG. 23F) on CD11c$^{hi}$ DC from WT (Ctla4$^{m/m}$) spleen cells at 24 hours after treatment with 500 µg of antibodies i.p. The data are summarized from 6 independent mice per group in two independent experiments involving 3 mice per group each.

FIGS. 24A-D. Distinct in vivo and in vivo blocking activities of anti-mouse CTLA4 mAb 4F10. FIGS. 24A and B show the effect of 4F10 on interaction of CTLA4-Fc to plate-coated B7-1 (FIG. 24A) or B7-2 (FIG. 24B). Biotinylated mouse CTLA4-Fc fusion protein were incubated with B7-coated plates in the presence of given concentration of control IgG or anti-mouse CTLA4 mAb 4F10. The CTLA4 binding is detected with HRP-conjugated streptavidin. Data shown are means of duplicated and are representative of two independent experiments. FIGS. 24C and D show the impact of 4F10 on B7-1 and B7-2 expression. Summary data on B7-1 (FIG. 24C) and B7-2 (FIG. 24D) levels from 6 mice per group. The B7 levels in the control IgG-treated group are artificially defined as 100%.

Figure 25:
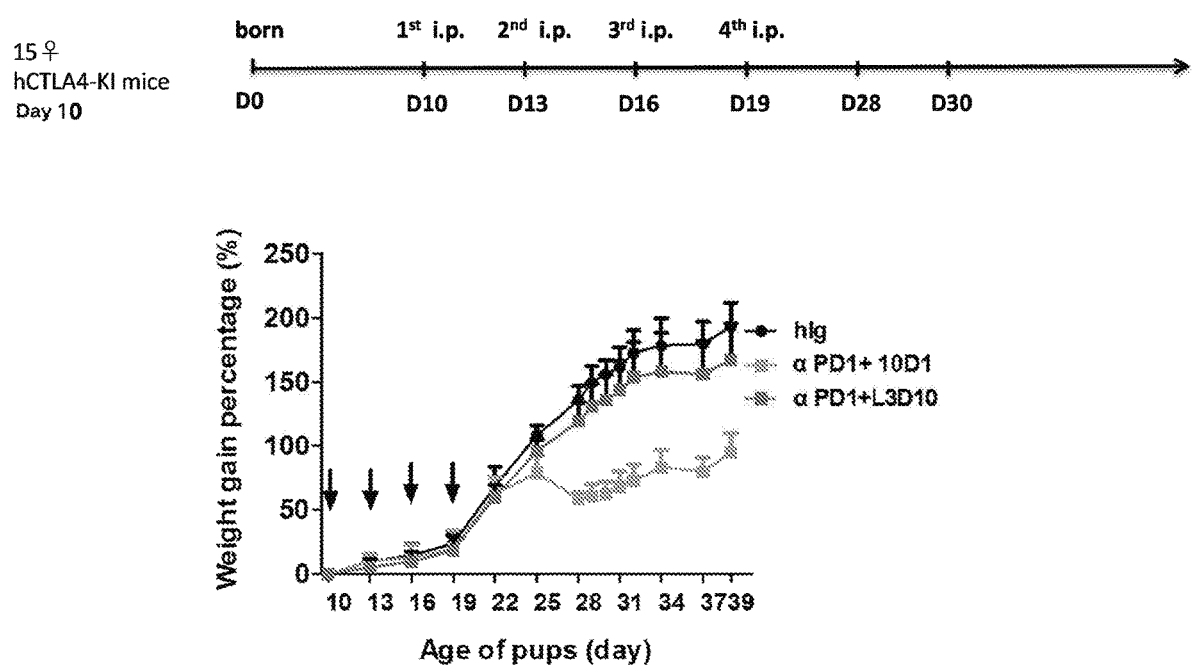

FIG. 25. Adverse effects of chimeric L3D10 and 10D1 in combination with anti-PD-1. Top panel depicts the experimental design. 10-day old female-only human CTLA4-knockin mice with body weight of greater than 4 grams were used for the study. They received indicated proteins or their combinations. Arrows indicate time of treatment (100 µg/mice/treatment). Data shown are means and S.D. of % weight gains. Chimeric L3D10 and 10D1 have comparable cancer therapeutic effect in adult mice (FIG. 13) but distinct adverse effects are seen when 10D1 is combined with the anti-PD-1 mAb.

Figure 26:
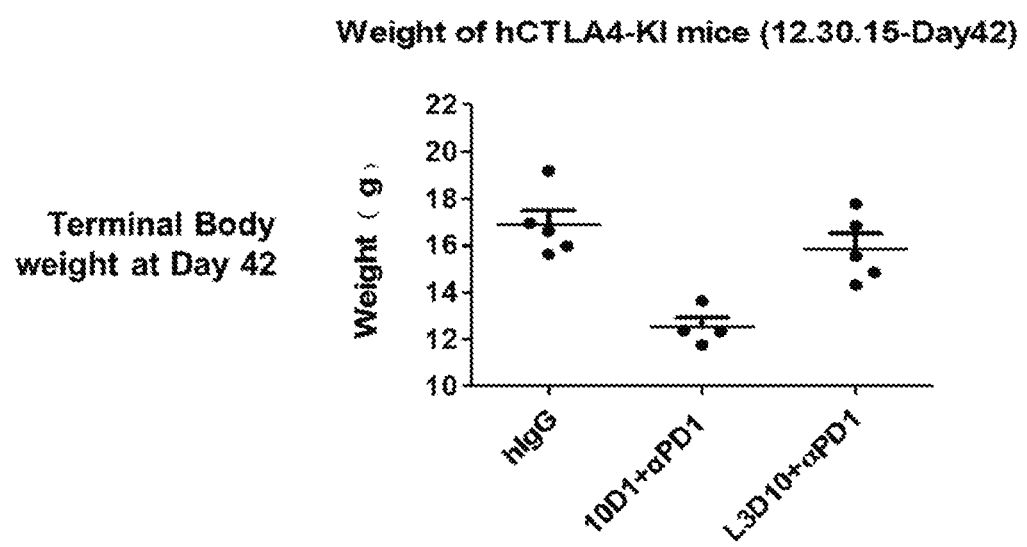

FIG. 26. Adverse effects of chimeric L3D10 and 10D1 in combination with anti-PD-1. The graph shows the terminal body weight on Day 42 in the mice from the experiment outlined in FIG. 25 that received either control IgG, 10D1+anti-PD-1 or chimeric L3D1+anti-PD-1 (n=5 per group). A significant reduction in weight is observed with the anti-PD1+10D1 combination, which was not seen with the anti-PD-1+Chimeric L3D10 combination.

Figure 27:
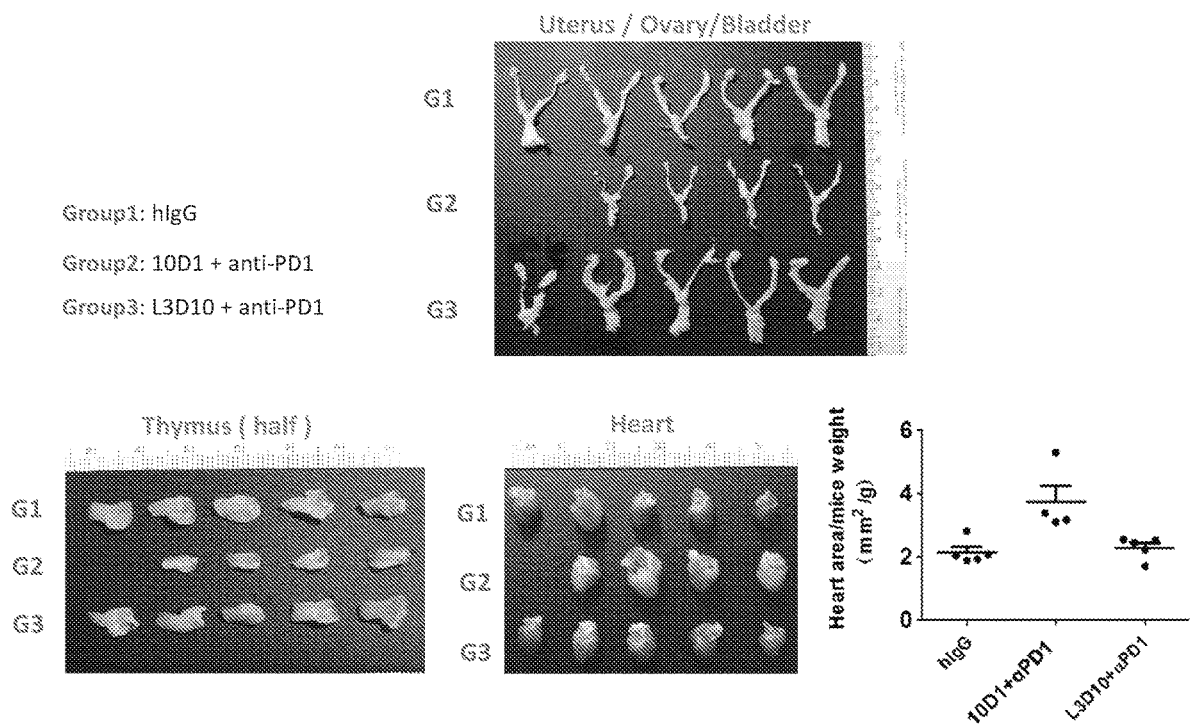

FIG. 27. Pathological effects of chimeric L3D10 and 10D1 in combination with anti-PD-1. To further examine to relative toxicity of L3D10 compared to 10D1 when administered in combination with anti-PD-1, we looked at the gross anatomy of the mice described in FIG. 26 above. The Uterus/Ovary/Bladder and thymus were noticeably smaller in mice treated with 10D1+PD-1, whereas the organs in mice treated with L3D10+anti-PD-1 was comparable to hIgG control. In contrast, the hearts dissected from mice treated with 10D1 appeared larger in size with a noticeably whiter appearance.

FIGS. 28A-D. Treatment with 10D1 in combination with anti-PD-1 results in abnormal erythropoiesis. Given the differences in the hearts observed in FIG. 27, we looked at erythropoiesis within the mice and observed clear differences in the mice treated with 10D1+anti-PD-1 relative to the groups treated with L3D10+anti-PD-1 or control antibody (hIgG), which were fairly similar. The bone marrow from mice treated with 10D1+anti-PD-1 had a noticeably whiter color (FIG. 28A) and the isolated blood was almost completely white in color (FIG. 28B). In accordance with this, when we analyzed differentiation of the red blood cells using distribution of CD119 and CD71 markers we observed a statistically significant reduction in the number of cells undergoing Stage IV development in the 10D1+anti-PD-1 treated mice. Representative FACS profiles are shown in FIG. 28C, while summary data are presented in FIG. 28D.

Figure 29:
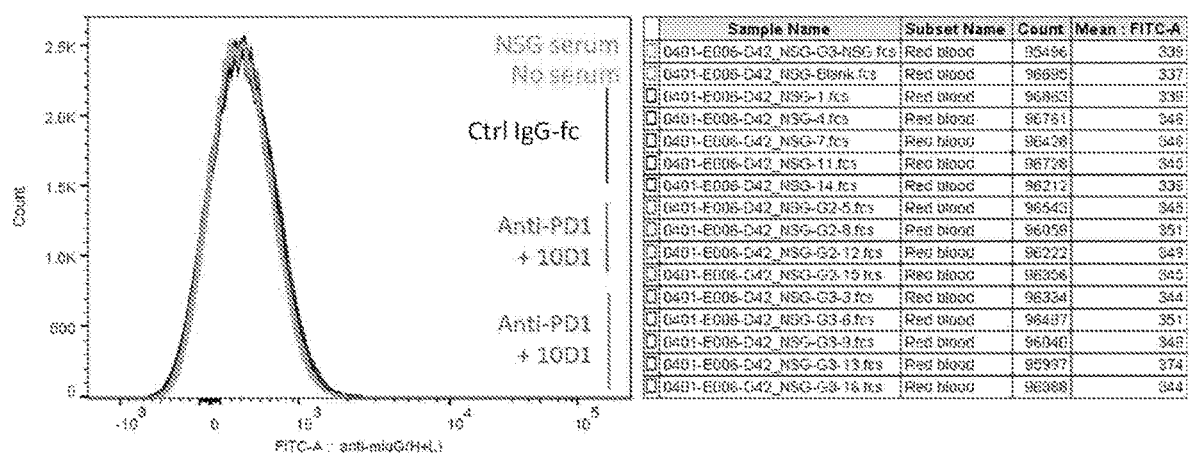

FIG. 29. Flow cytometry analysis of anti-red blood cell antibodies. Blood samples from NOD.SCID.Il2rg−/− (NSG) mice were stained with plasma samples from the mice that received antibody treatment during the perinatal period. Sera from NSG mice and those without sera were used as negative control. All sera were used at 1:50 dilution. These data show that no mice produced anti-red cell antibodies.

Figure 30:
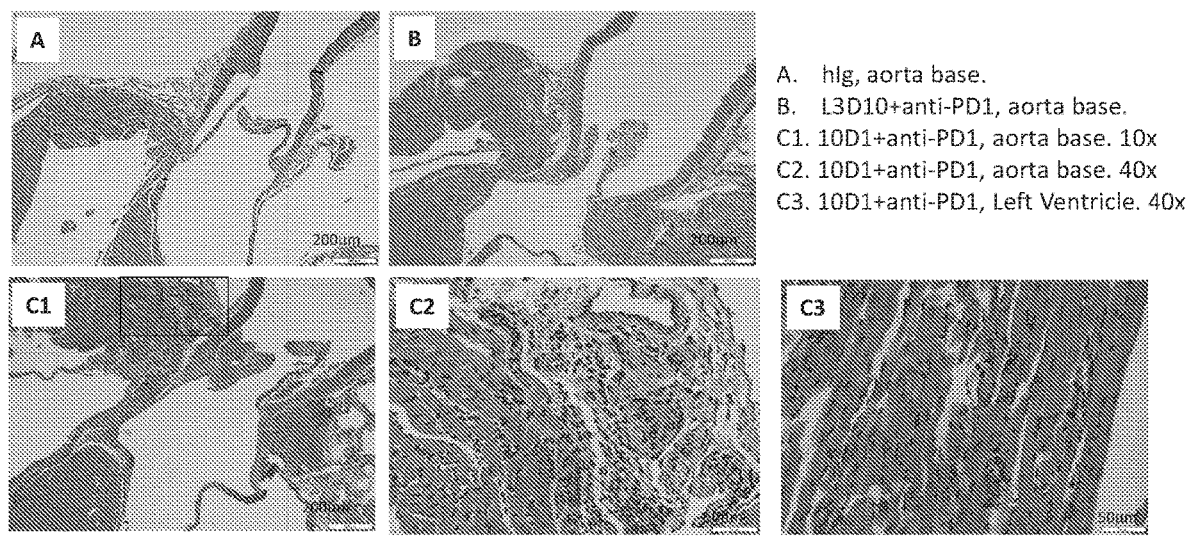

FIG. 30. Pathology of the heart in mice treated with chimeric L3D10 and 10D1 in combination with anti-PD-1. To further determine the toxicology of L3D10 vs 10D1 in combination with anti-PD-1, we performed histological analysis of the heart in mice described in FIG. 26. Mice treated with 10D1+anti-PD-1 displayed a high level of T cell infiltration that was not observed in mice treated with L3D10+anti-PD-1 or mice treated with human IgG control.

Figure 31:
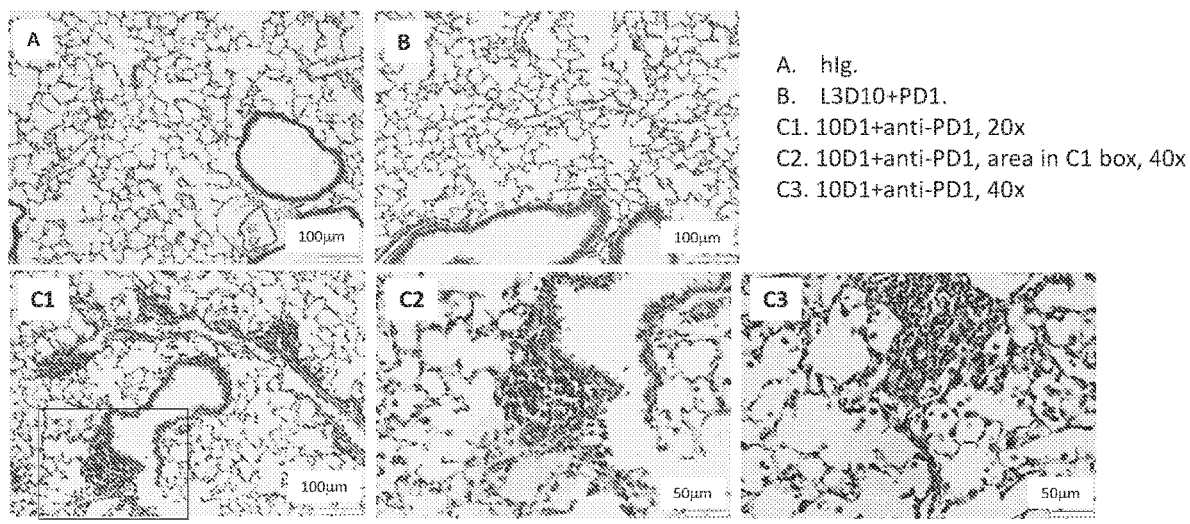

FIG. 31. Pathology of the lung in mice treated with chimeric L3D10 and 10D1 in combination with anti-PD-1. To further determine the toxicology of L3D10 vs 10D1 in combination with anti-PD-1, we performed histological analysis of the lung in mice described in FIG. 26. Mice treated with 10D1+anti-PD-1 displayed a high level of T cell infiltration that was not observed in mice treated with L3D10+anti-PD-1 or mice treated with human IgG control.

Figure 32:
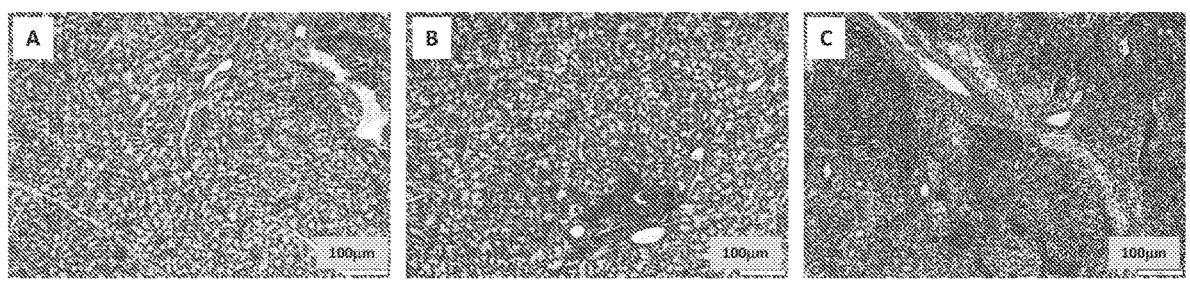

FIG. 32. Pathology of the salivary gland in mice treated with chimeric L3D10 and 10D1 in combination with anti-PD-1. To further determine the toxicology of L3D10 vs 10D1 in combination with anti-PD-1, we performed histological analysis of the salivary in mice described in FIG. 26. Mice treated with 10D1+anti-PD-1 displayed a much higher level of T cell infiltration than observed in mice treated with L3D10+anti-PD-1 or mice treated with human IgG control.

Figure 33:
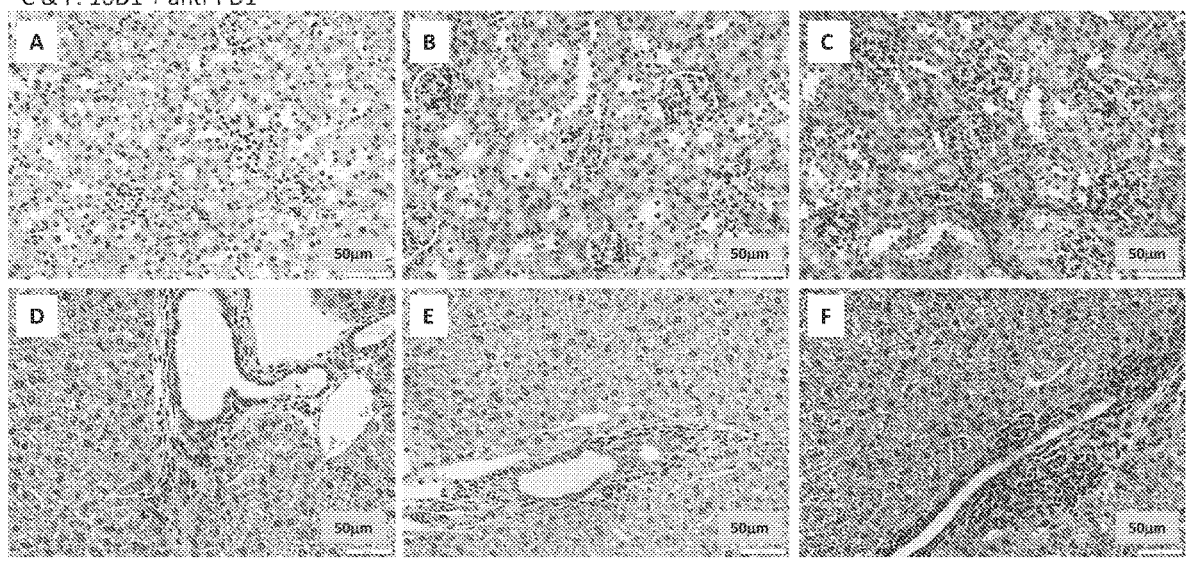

FIGS. 33A-F. Pathology of the kidney and liver in mice treated with chimeric L3D10 and 10D1 in combination with anti-PD-1. To further determine the toxicology of L3D10 vs 10D1 in combination with anti-PD-1, we performed histological analysis of the kidney and liver in mice described in FIG. 26. FIGS. 33A-C are sections from the kidney and FIGS. 33D-E are sections taken from the liver. Mice treated with 10D1+anti-PD-1 displayed a high level of T cell infiltration than observed in mice treated with L3D10+anti-PD-1 or mice treated with human IgG control.

Figure 34:
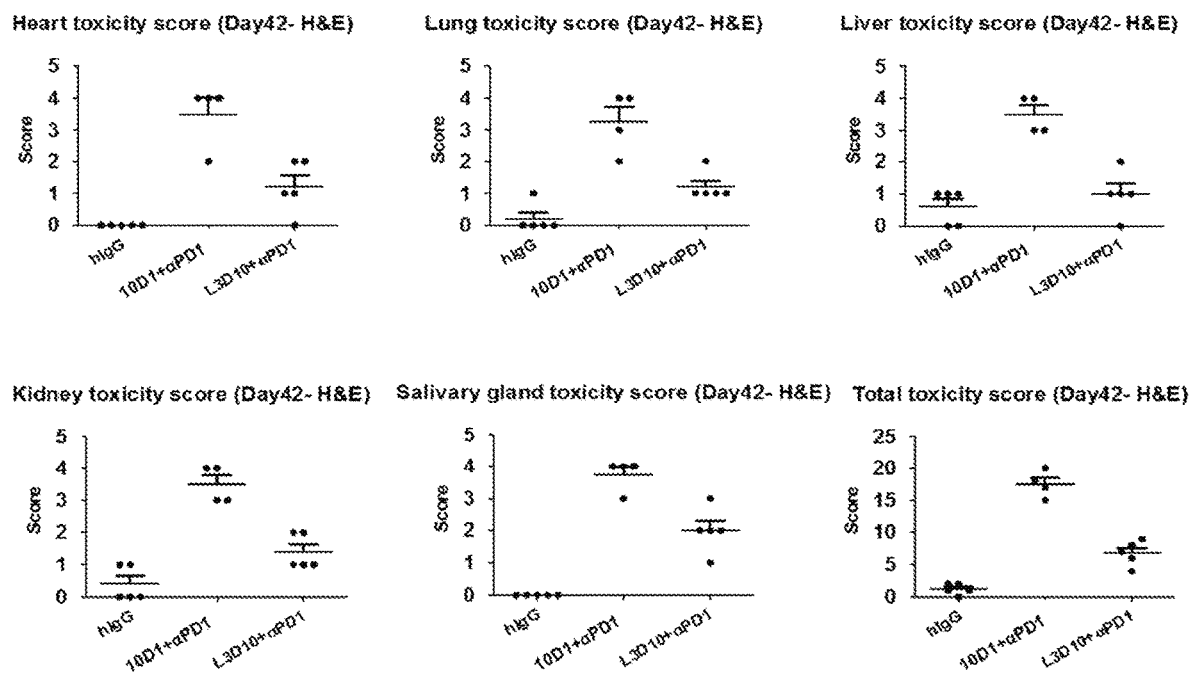

FIG. 34. Toxicity scores of mice treated with chimeric L3D10 and 10D1 in combination with anti-PD-1. This tissue data shown if FIGS. 30-33 is summarized and shows the high toxicity scores of mice treated with 10D1+anti-PD-1 relative to L3D10+anti-PD-1 which has scores only marginally higher than the hIgG control mouse group.

Figure 35:
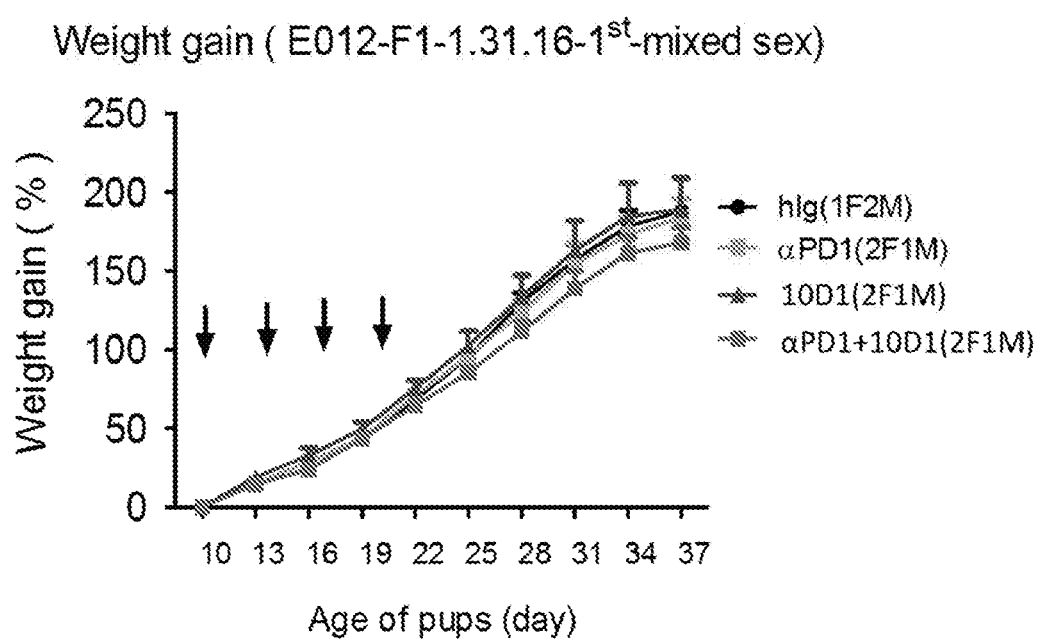

FIG. 35. 10D1+anti-PD-1 do not have significant toxicity in the Ctla4$^{h/m}$ mice as evidenced by normal body weight gains in mice that received antibody treatment during the perinatal period. The mice received treatments with given antibody or combinations on days 10, 13, 16, 19 and 22 intraperitoneally (100 µg/mice/injection/antibody). Mice were weighed at least once every 3 days.

Figure 36:
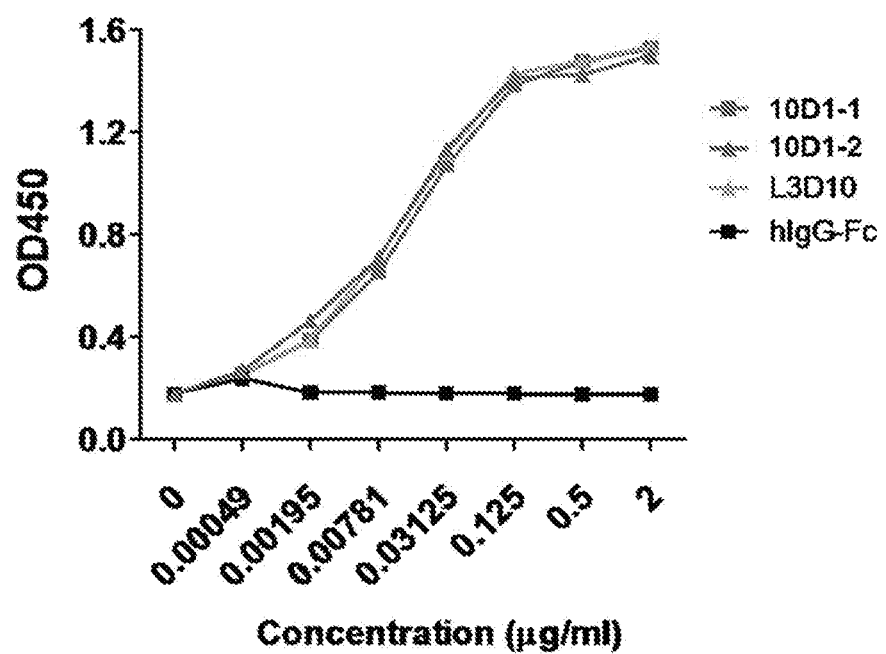

FIG. 36. L3D10 and 10D1 display similar binding patterns for plate immobilized CTLA4. ELISA plates were coated with 1 µg/ml of CTLA4-His protein (Sino Biological, China). The given concentration of biotinylated binding proteins were added and binding measured using HRP-conjugated streptavidin. 10D1-1 and -2 are two independent material lots of the same antibody. hIgG-Fc is a human Ig negative control.

Figure 37:
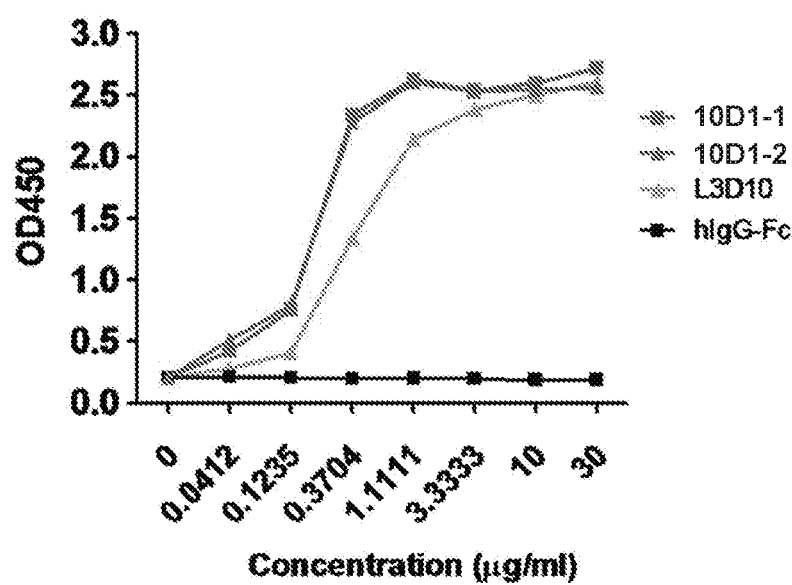

FIG. 37. L3D10 displays reduced binding soluble CTLA4. Given concentration of anti-human CTLA4 mAbs were coated on the plate overnight, after washing and blocking with bovine serum albumin, biotinylated CTLA4-Fc was added at 0.25 µg/ml. After incubation and washing, the amounts of captured CTLA4-Fc were measured using HRP-labeled streptavidin.

FIG. 38. Alignment of the humanized antibody variable regions with the parental L3D10 antibody sequence. The heavy chain variable region (top)(SEQ ID NOS: 62-64) and light chain variable region (bottom)(SEQ ID NOS: 70-72) of the humanized antibody sequences are alignment with the parental L3D10 antibody (heavy chain: SEQ ID NO: 57; light chain: SEQ ID NO: 65) and the respective human antibody frameworks (heavy chain: SEQ ID NOS: 58-61; light chain: SEQ ID NOS: 66-69). Back mutations to the mouse parental sequence are highlighed in yellow. Novel amino acids i.e. amino acid residues not present in the parental antibody sequence or the respective human antibody framework are highlighted in green. Mutations introduced into the CDR2 sequences are shown in purple. CDR sequences are shown in red based on www.bioinf.org.uk/abs/.

Figure 39:
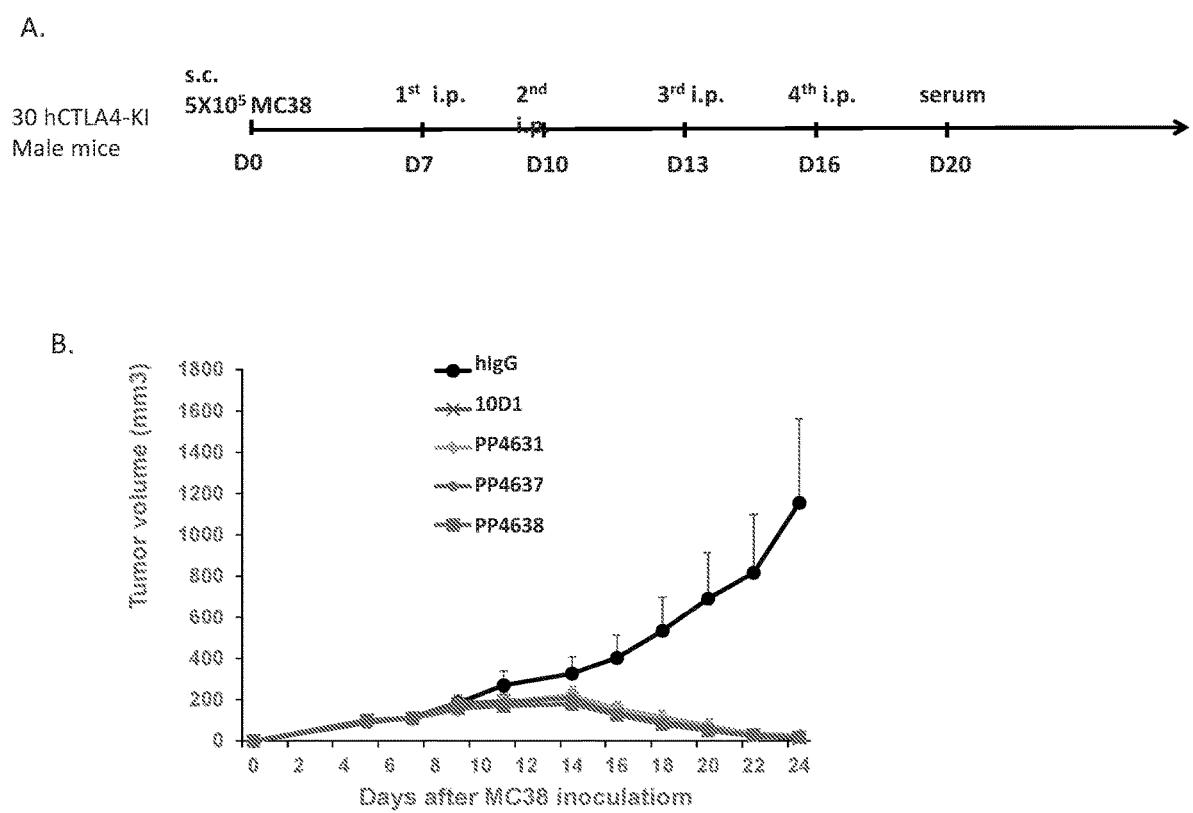

FIGS. 39A-B. Anti-tumor activity of humanized L3D10 antibodies compared to 10D1. Using the MC38 mouse tumor model in human CTLA4 knockin mice we looked at the anti-tumor activity of humanized L3D10 antibodies compared to the chimeric L3D10 antibody and 10D1. The top panel shows the treatment schedule of the in vivo experiment; mice were given a total of 4 doses of antibody every 3 days starting on day 7 after inoculation. All humanized antibodies (n=6 per group) completely eradicated the tumors and were comparable to 10D1 (bottom panel).

Figure 40:
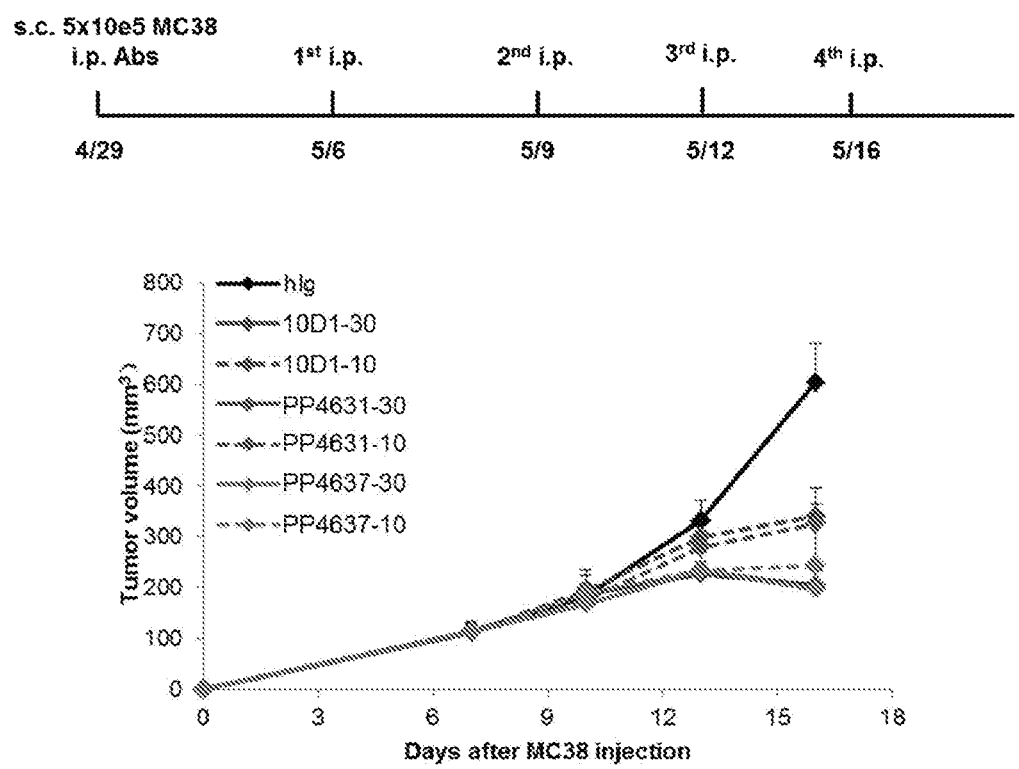

FIG. 40. Anti-tumor activity of humanized L3D10 antibodies in CTLA4$^{h/m}$ mice. The top panel shows the treatment schedule of the in vivo experiment; Ctla4$^{h/m}$ mice received control hIg or one of three different anti-human CTLA4 mabs at doses of 30 (−30, solid lines) or 10 (−10, dotted lines) mg per injection at the indicated dates after MC38 tumor injection. Tumor sizes were measured once every three days.

Figure 41:
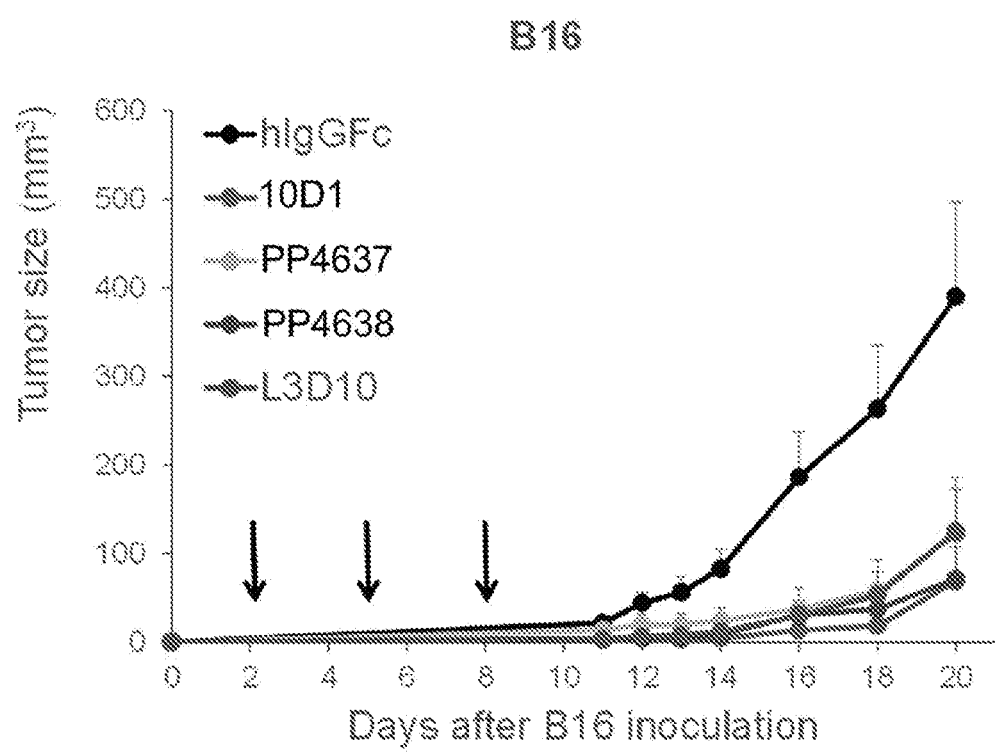

FIG. 41. Therapeutic effect of anti-CTLA-4 mAb in minimal disease B16-F1 tumor model. Using the B16-F1 mouse tumor model in human CTLA4 knockin mice we looked at the anti-tumor activity of humanized L3D10 antibodies. 1×10$^5$ B16 tumor cells were injected (s.c.) into Ctla4$^{h/h}$ mice (n=5-6). On days 2, 5, and 8, the mice were treated with control Ig, 10D1, chimeric L3D10 or PP4637 and PP4638 (250 µg/mouse, i.p.). Tumor incidence and sizes were measured every other day. 10D1 vs. hIgGFc: P=0.00616; L3D10 vs. hIgGFc: P=0.0269; 10D1 vs. L3D10: P=0.370; PP4637 vs. hIgGFc: P=0.0005; PP4637 vs. 10D1: P=0.805; PP4638 vs. hIgGFc: P=0.0016; PP4638 vs. 10D1: P=0.856. Data represent mean±SEM of 5-6 mice per group. Sizes of tumors were considered as 0 for mice that never developed tumor.

Figure 42:
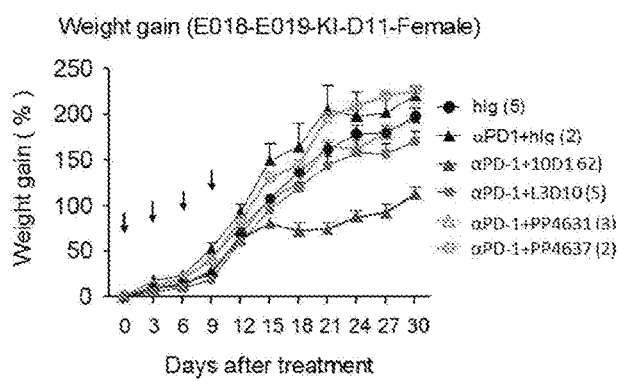

FIG. 42. Comparison among 10D1, PP4631 and PP4637 females for their combined toxicity with anti-PD-1 mAb. Female CTLA4$^{h/h}$ mice were treated on days 10 or 11 days after birth with 4 injections of antibodies (100 µg/mice/injection, once every three days) or control Fc as specified in the legends. Mice were weighted once every 3 days. Data shown are means and SEM of % weight gain over a 30 day period. All mice were sacrificed on day 43 for histological analysis. The number of mice used per group is shown in the parentheses of labels.

Figure 43:
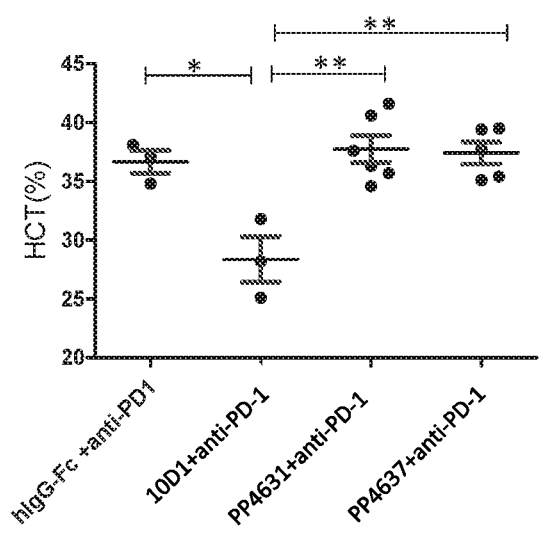

FIG. 43. Combination therapy with 10D1 and anti-PD-1 cause anemia, whereas those with either PP4631+anti-PD-1 or PP4637+anti-PD-1 do not. Data shown are hematocrit of 43 day old mice that have received four treatments of antibodies on days 11, 14, 17 and 20 at doses of 100 µg/mouse/antibodies.

Figure 44A:
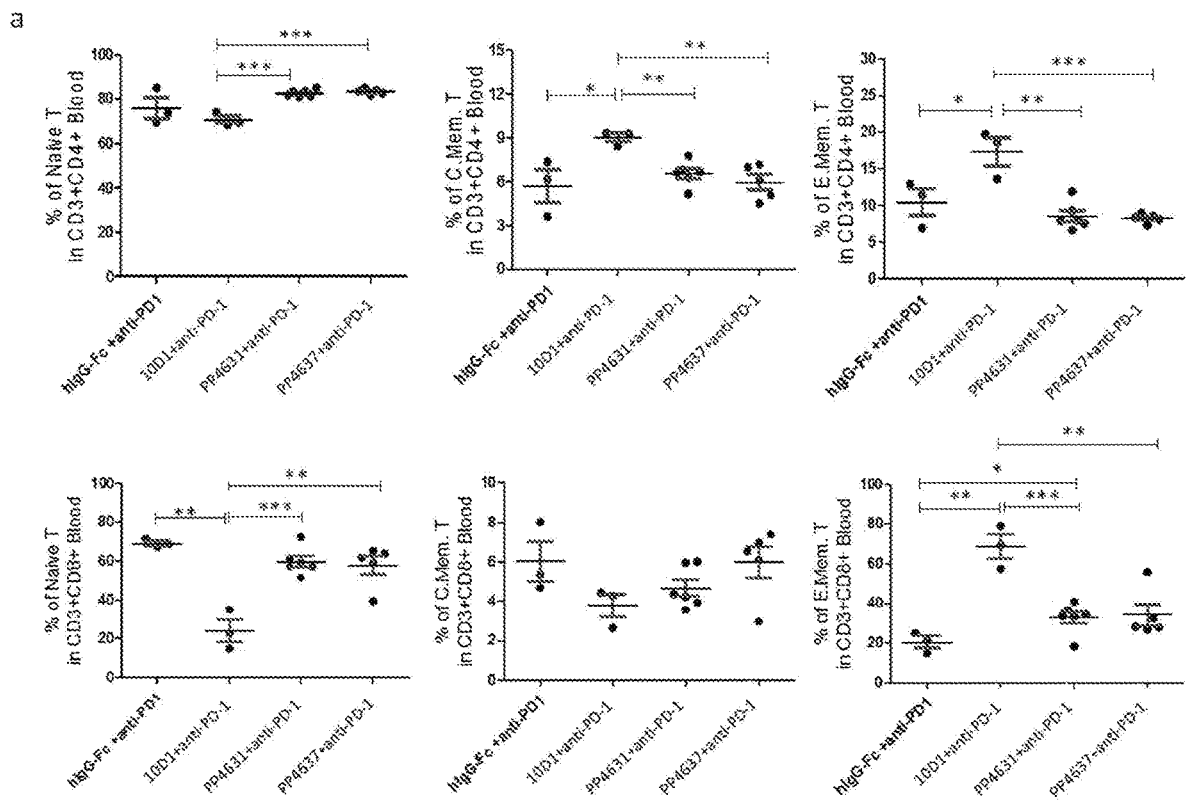
Figure 44B:
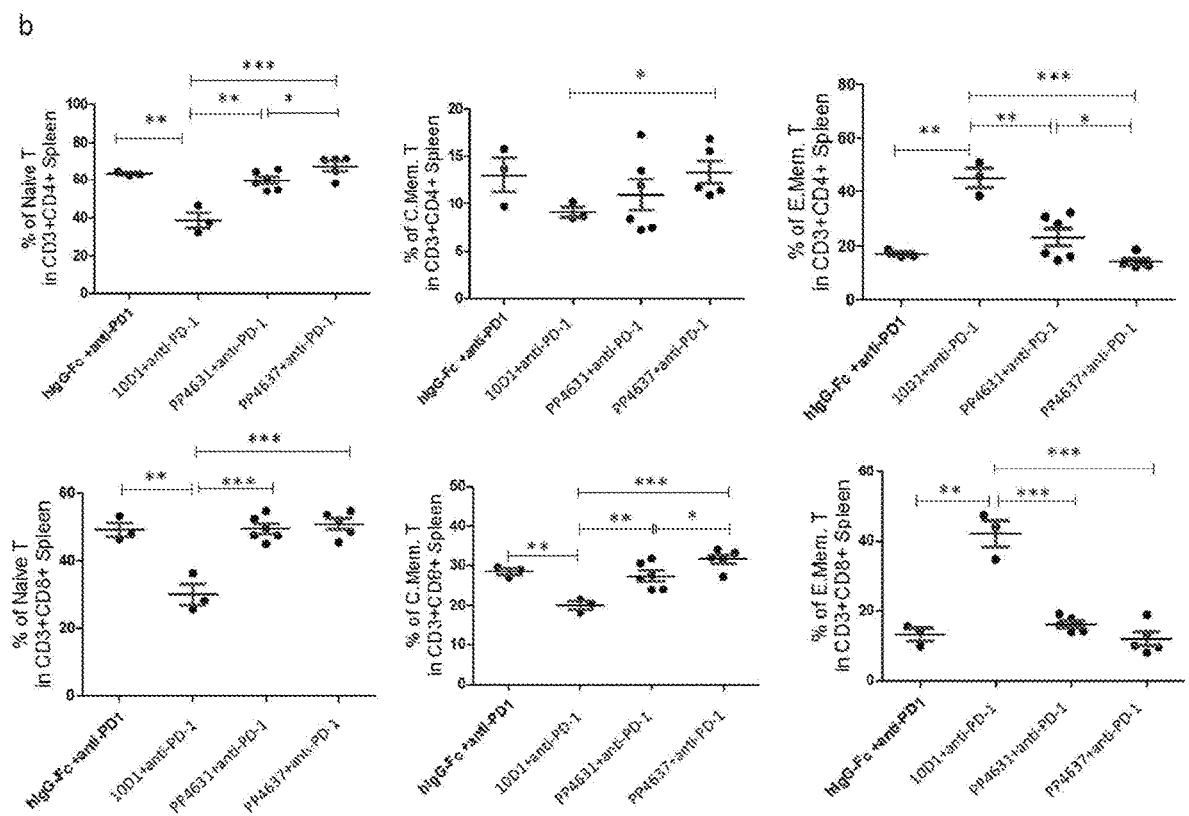

FIGS. 44A-B. Combination therapy with 10D1+anti-PD-1 cause systemic T cell activation, whereas those with either PP4631+anti-PD-1 or PP4637+anti-PD-1 do not. Data shown are % of CD4 (upper panels) and CD8 T cells (lower panels) with phenotypes of naïve (CD44$^{lo}$CD62L$^{hi}$), central memory (CD44$^{hi}$CD62L$^{hi}$) and effector memory (CD44$^{hi}$CD62Llo) T cells in either peripheral blood (FIG. 44A) or in the spleen (FIG. 44B). The cells were harvested from 43 day old mice that have received four treatments of antibodies on days 11, 14, 17 and 20 at doses of 100 µg/mouse/antibodies.

Figure 45:
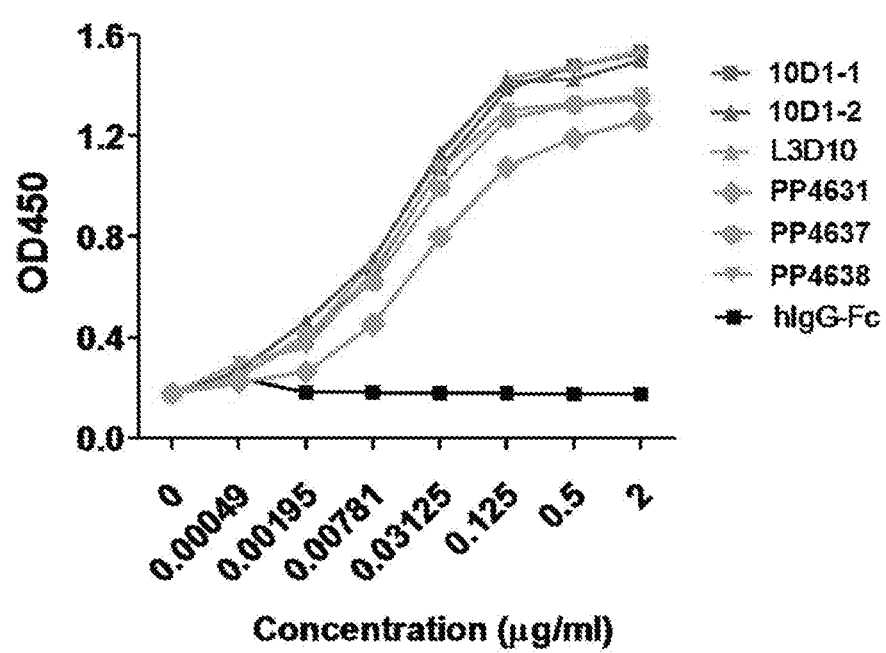

FIG. 45. Humanization of L3D10 does not affect binding to immobilized CTLA4. The capacity of the humanized L3D10 antibodies to bind immobilized CTLA4 was determined as described in FIG. 36. X-axis indicates the concentration of anti-CTLA-4 mAbs added into solution. Humanization does not affect binding to immobilized CTLA4 and all 3 humanized antibodies demonstrated similar binding to the parental chimeric L3D10 antibody and 10D1. Similar patterns were observed when CTLA4-Ig was used instead of CTLA-4-his.

Figure 46:
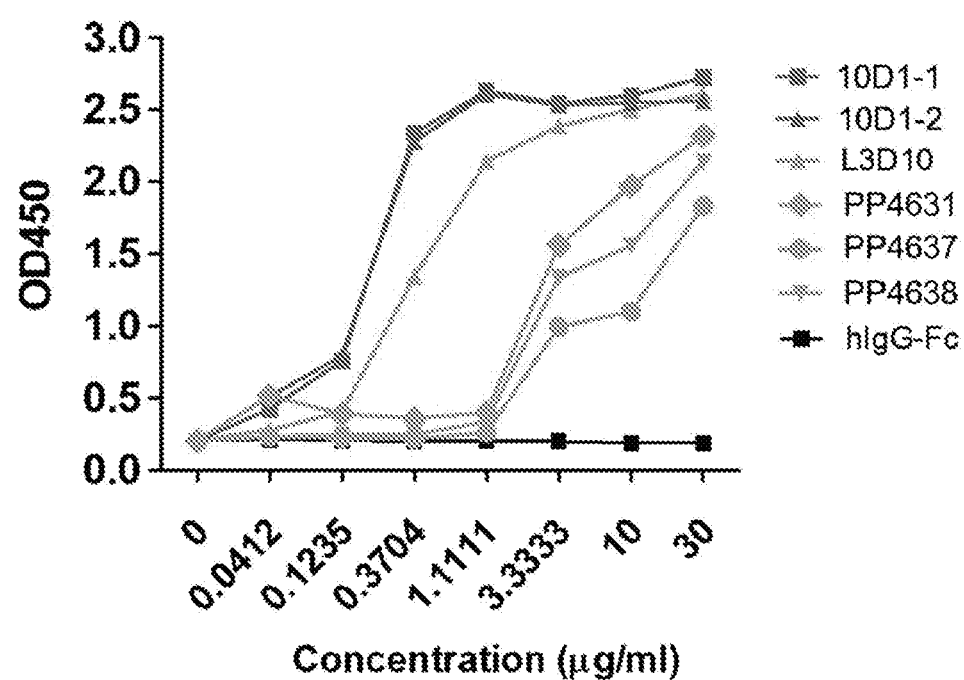

FIG. 46. Humanization further reduces L3D10 binding to soluble CTLA4. The capacity of the humanized L3D10 antibodies to bind soluble CTLA4 was determined as described in FIG. 37. X-axis indicates the concentration of anti-CTLA-4 mAbs coated onto ELISA plates. Humanization further reduces binding to soluble CTLA4 relative to the parental L3D10 chimeric antibody. Similar patterns were observed when CTLA4-Ig was used instead of CTLA-4-his.

FIGS. 47A-B. PP4631, PP4638 and PP4637 do not block B7-CTLA-4 interactions in vitro. FIG. 47A shows blocking of the B7-1-CTLA-4 interaction by anti-human CTLA-4 mAbs 10D1, PP4631, PP4637 and L3D10. B7-1 Fc was immobilized at the concentration of 0.5 μg/ml. Biotinylated CTLA4-Fc was added at 0.25 μg/ml along with given doses of antibodies. Data shown are means of duplicate optical density at 405 nM. FIG. 47B shows blocking of B7-2-CTLA-4 interaction by anti-human CTLA-4 mAbs 10D1 and L3D10. As in FIG. 47A, except that B7-2-Fc was immobilized.

Figure 48:
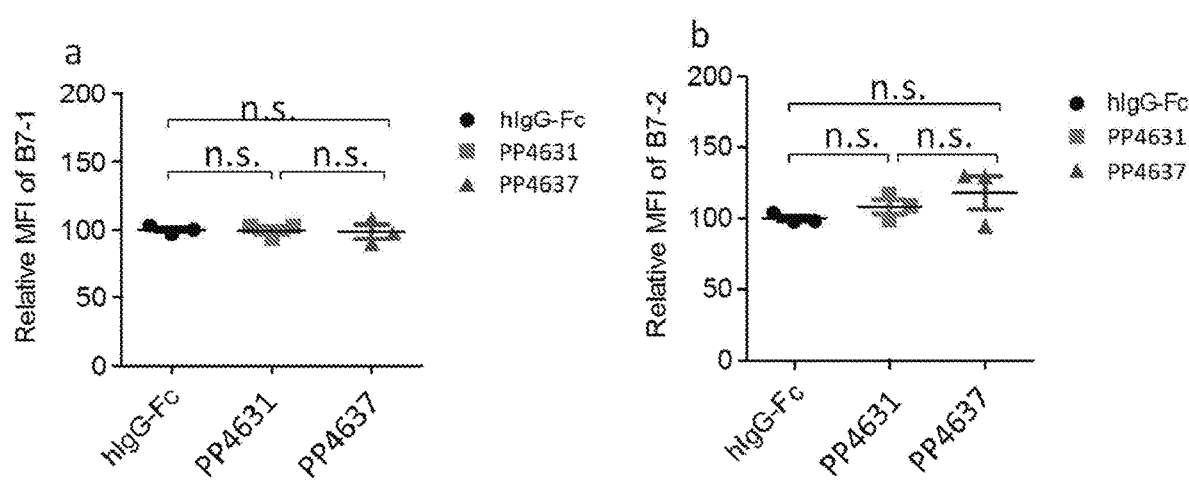

FIG. 48. PP4631 and PP4637 do not block B7-CTLA-4 interactions in vivo as demonstrated by their lack of effect on B7-1 and B7-2 expression on dendritic cells. Summary data on B7-1 (a) and B7-2 (b) levels from 3 mice per group. The B7 levels in the control IgG-treated group are artificially defined as 100%.

Figure 49:
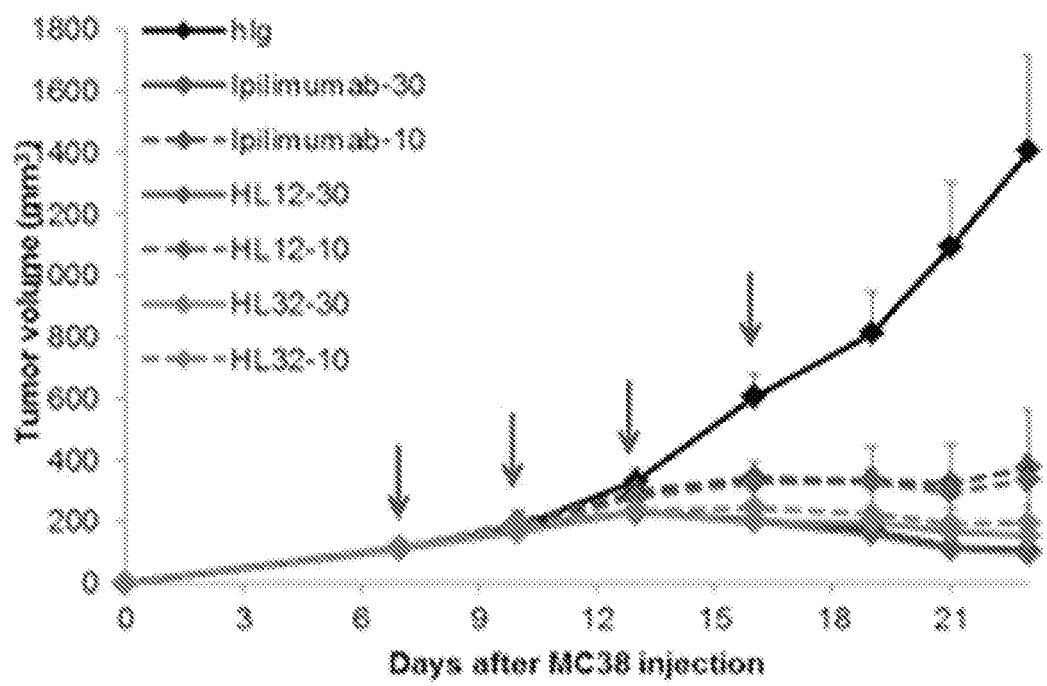

FIG. 49. PP4637, which exhibits the best safety profile in combination with anti-PD-1 mAb (see FIG. 42), is the most potent in causing tumor rejection based on tumor rejection at the lowest therapeutic doses. Ctla4$^{h/m}$ mice received control IgFc or one of three different anti-human CTLA4 mab at doses of 30 (−30, solid lines) or 10 (−10, dotted lines) μg per injection at the indicated dates. Tumor sizes were measured once every three days. At 10 μg/injection, PP4637 (HL32) is the most efficient in inducing tumor rejection.

Figure 50:
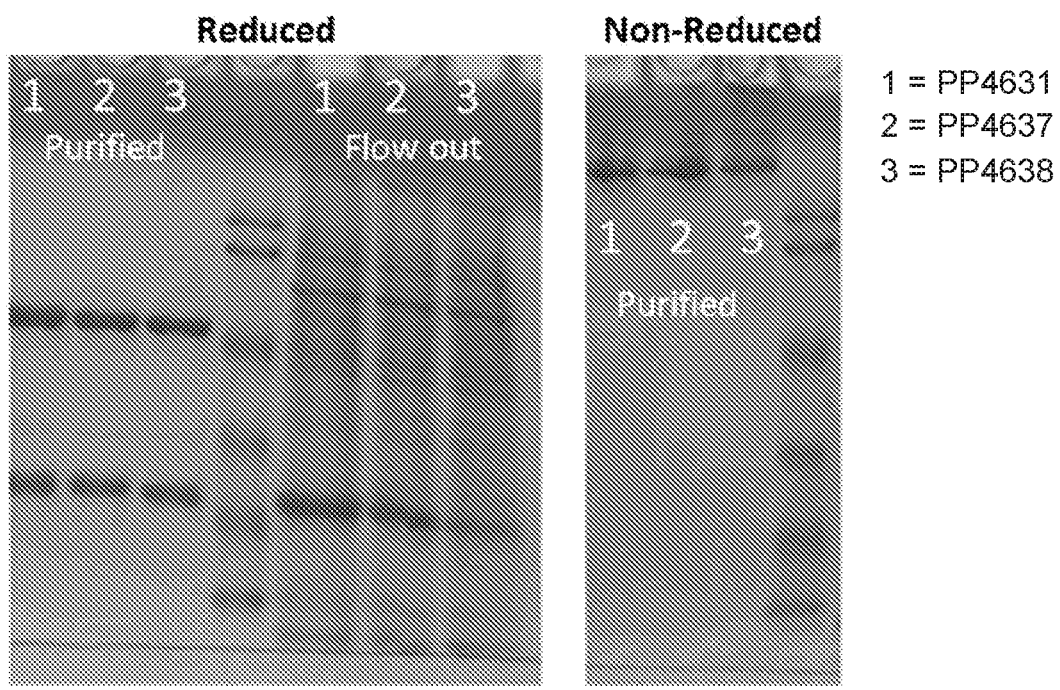

FIG. 50. Humanized antibody purity assessment. Transiently expressed humanized L3D10 antibodies were purified by Protein A chromatography and samples from all 3 antibodies was assessed by reducing and non-reducing SDS-PAGE. Purified proteins produced gel bands indicative in size of an antibody molecule under both reducing and non-reducing conditions. The "Flow out" lanes show the protein A column flow through, indicating that the majority of the antibody protein adhered to the protein A column.

FIG. 51. Size Exclusion Chromatography (SE-HPLC) of transiently expressed protein. Protein samples for each of the humanized antibodies were analyzed by SE-HPLC following single step Protein A chromatography. Top panel: antibody PP4631. Middle panel: antibody PP4637. Bottom panel: antibody PP4638.

Figure 52:
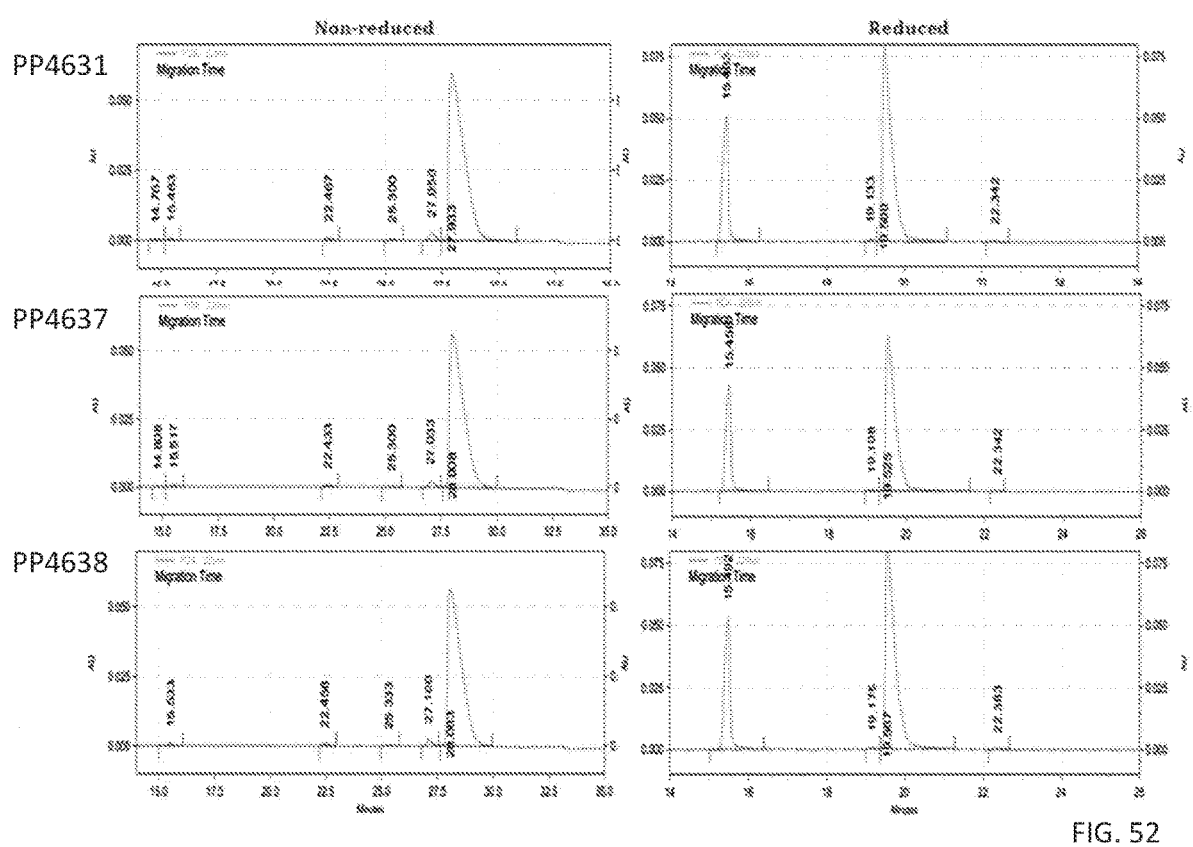

FIG. 52. CE-SDS analysis of transiently expressed protein. Protein samples for each of the humanized antibodies were analyzed by CE-SDS following single step Protein A chromatography. Left panels show the results under non-reduced conditions, and the right panels show the results under reduced conditions. Top panel: antibody PP4631. Middle panel: antibody PP4637. Bottom panel: antibody PP4638.

Figure 53A:
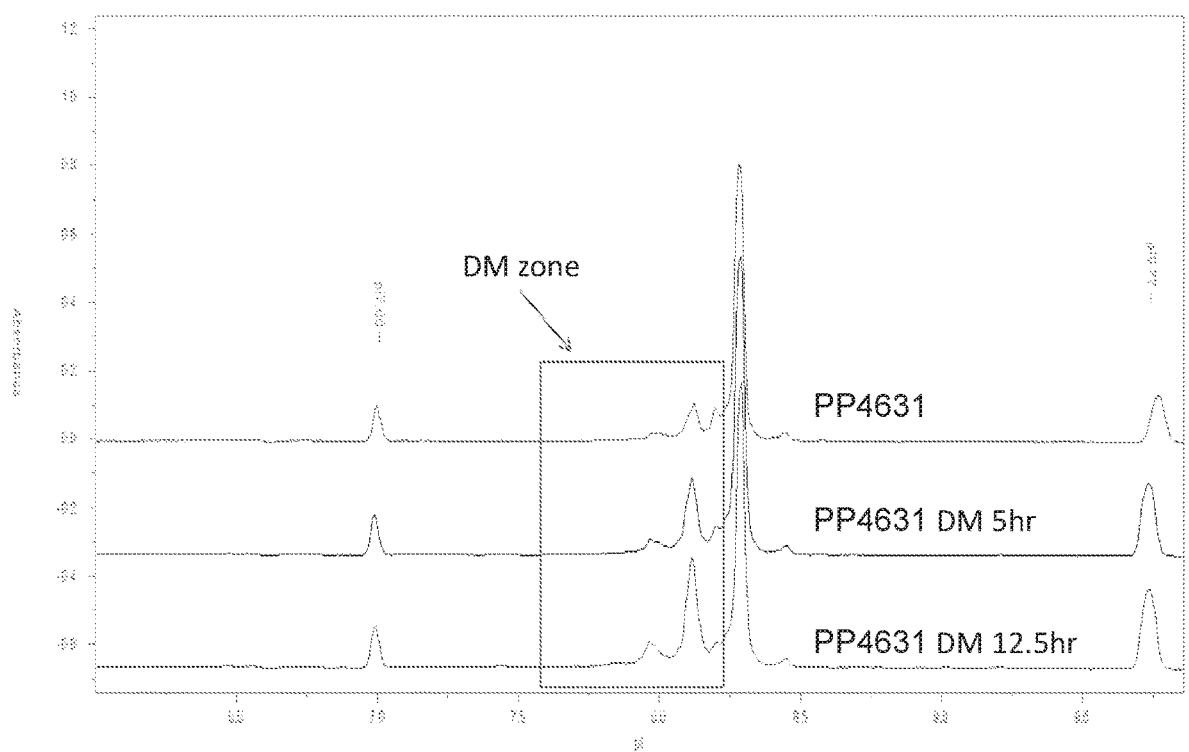
Figure 53B:
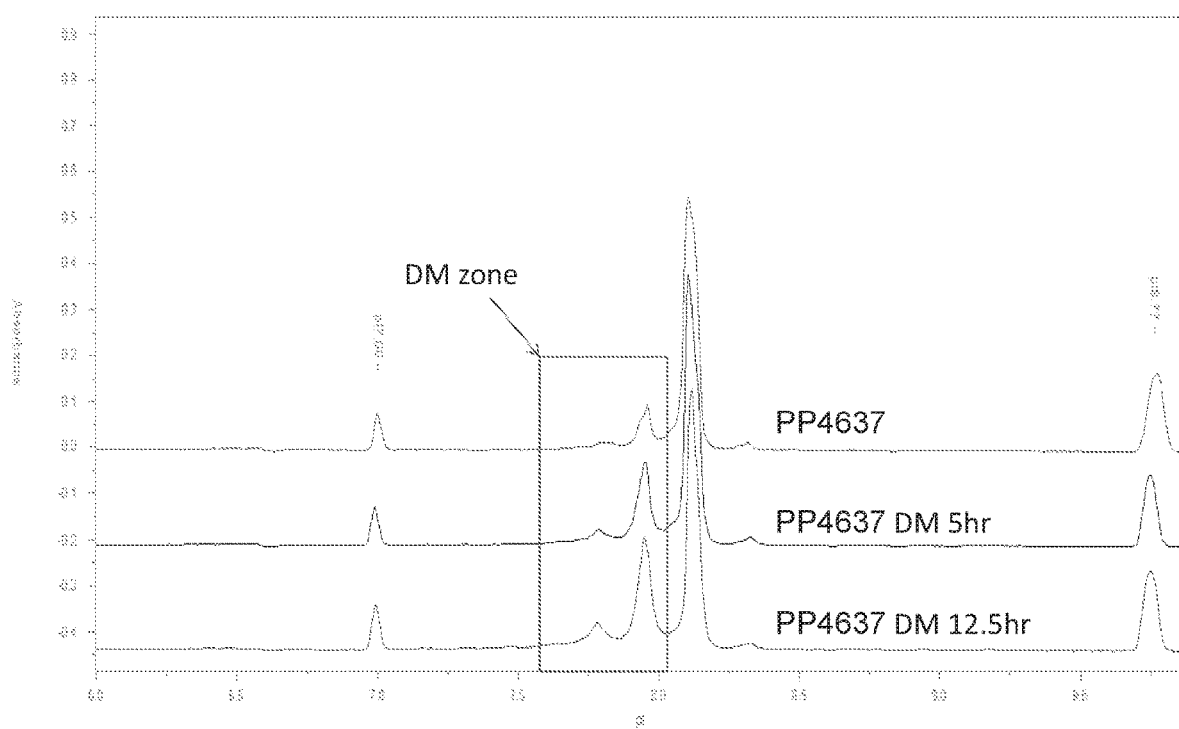
Figure 53C:
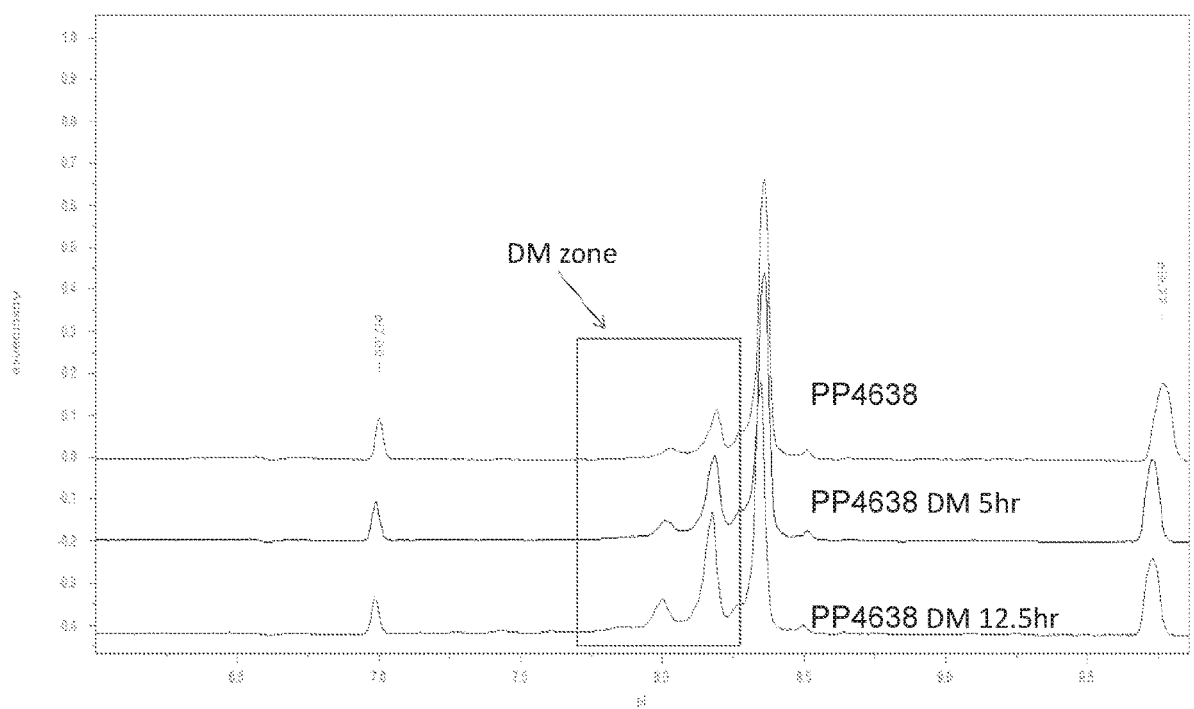

FIGS. 53A-C. Charge isoform profile and deamidation of the humanized L3D10 antibodies as determined by capillary isoelectric focusing (cIEF). The level of protein deamidation under high pH stress was determined by comparing the Humanized L3D10 antibodies before and after high pH stress treatment over two different time periods (5 hrs and 12.5 hrs) were analyzed by cIEF analysis. FIGS. 53A-C show the profiles for antibodies PP4631, PP4637 and PP4638, respectively.

FIGS. 54A-C. Differential Scanning calorimetry (DSC) Thermal Analysis of the humanized L3D10 antibodies. In order to determine the thermal stability and melting temperatures of the different antibodies, they were subject to Differential Scanning calorimetry (DSC) Thermal Analysis. FIGS. 54A-C show the normalized DSC curves for antibodies PP4631, PP4637 and PP4638, respectively.

FIG. 55. Alignment of the human, macaque and mouse CTLA-4 extracellular domains. The amino acid sequences of the human (Hm, shown in red)(SEQ ID NO: 73), macaque (Mk, shown in black) and mouse (Ms, shown in green) CTLA-4 protein extracellular domains are aligned and the conserved amino acids (relative to the human sequence) are shown with dashes (-). In order to help the alignment, the mouse sequence has a deletion and insertion (relative to the human and monkey sequences) at the positions highlighted in yellow. The known B7-1Ig binding site is shown in bold and underlined. The sequences demonstrate that the human and monkey sequences are highly conserved, whereas the mouse sequence has a number of amino acid differences. Based on this sequence alignment, 11 mutant (M1-M11) (SEQ ID NOS: 40-50) human CTLA-4Fc proteins were designed that incorporate murine specific amino acids—the amino acids incorporated into each mutant protein are shown in blue.

FIGS. 56A-B. Amino acid sequence composition of the WT and mutant CTLA-4Fc proteins. DNA constructs encoding the WT CTLA-4Fc protein (SEQ ID NO: 39) and 11 mutant proteins (SEQ ID NOS: 40-50) incorporating murine Ctla-4 amino acids were designed as shown. The amino acid sequences are for mature proteins, including the IgG1 Fc portion, but not the signal peptide. The known B7-1Ig binding site is shown in large blue letters and double-underlined. The replaced murine amino acid residues in the mutant are shown lower case in red. The IgG1 Fc portion of the proteins in underlined.

Figure 57:
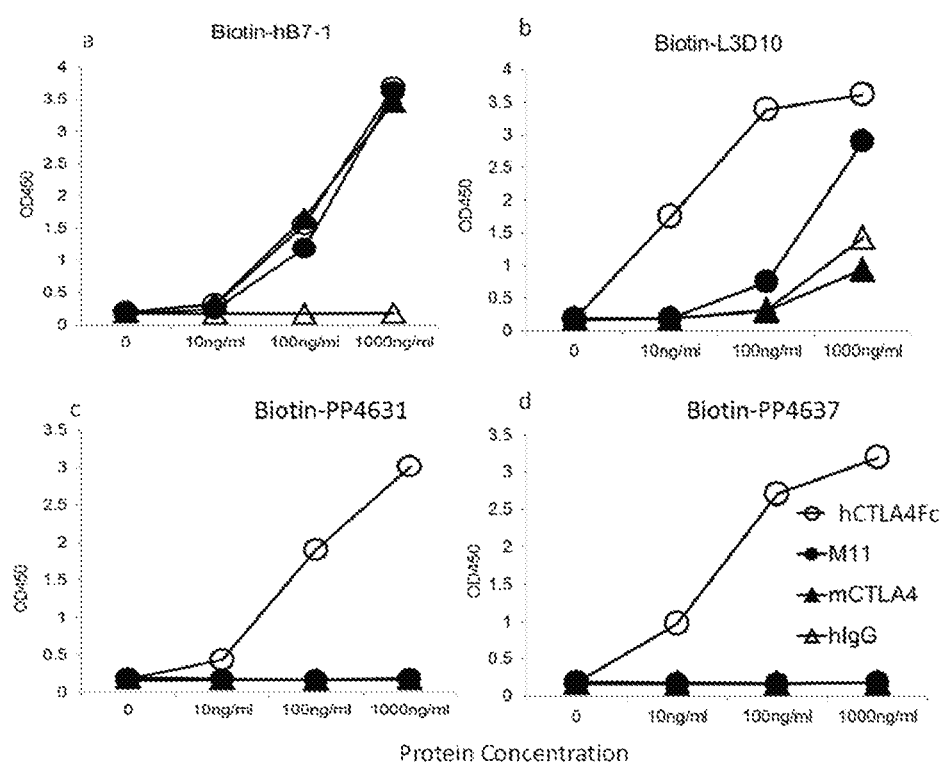
Figure 58:
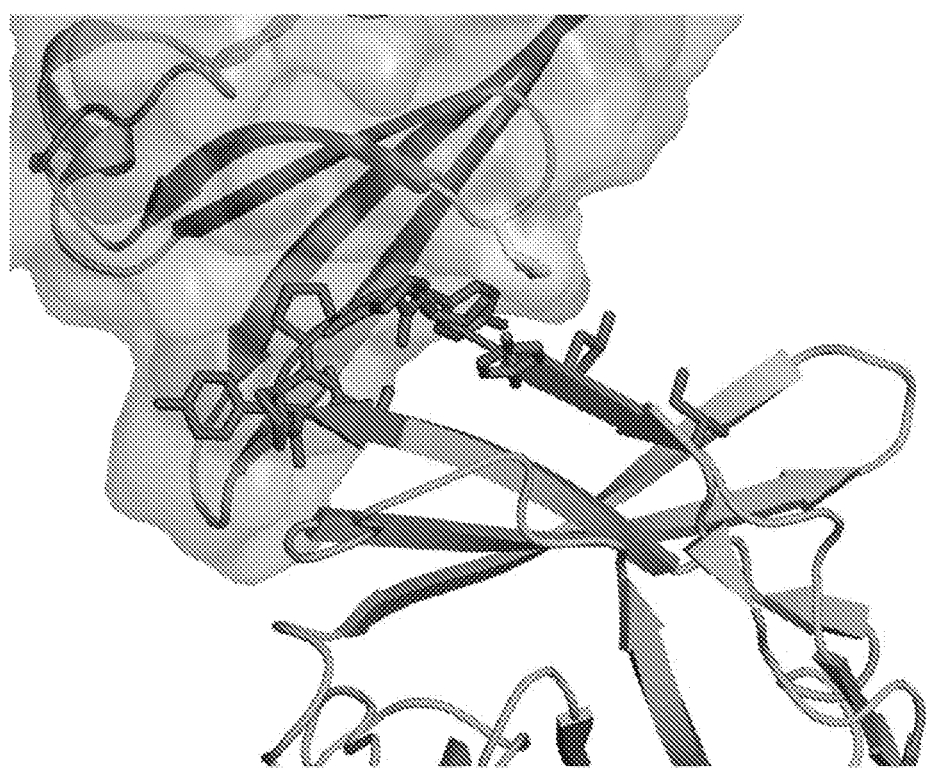
Figure 60:
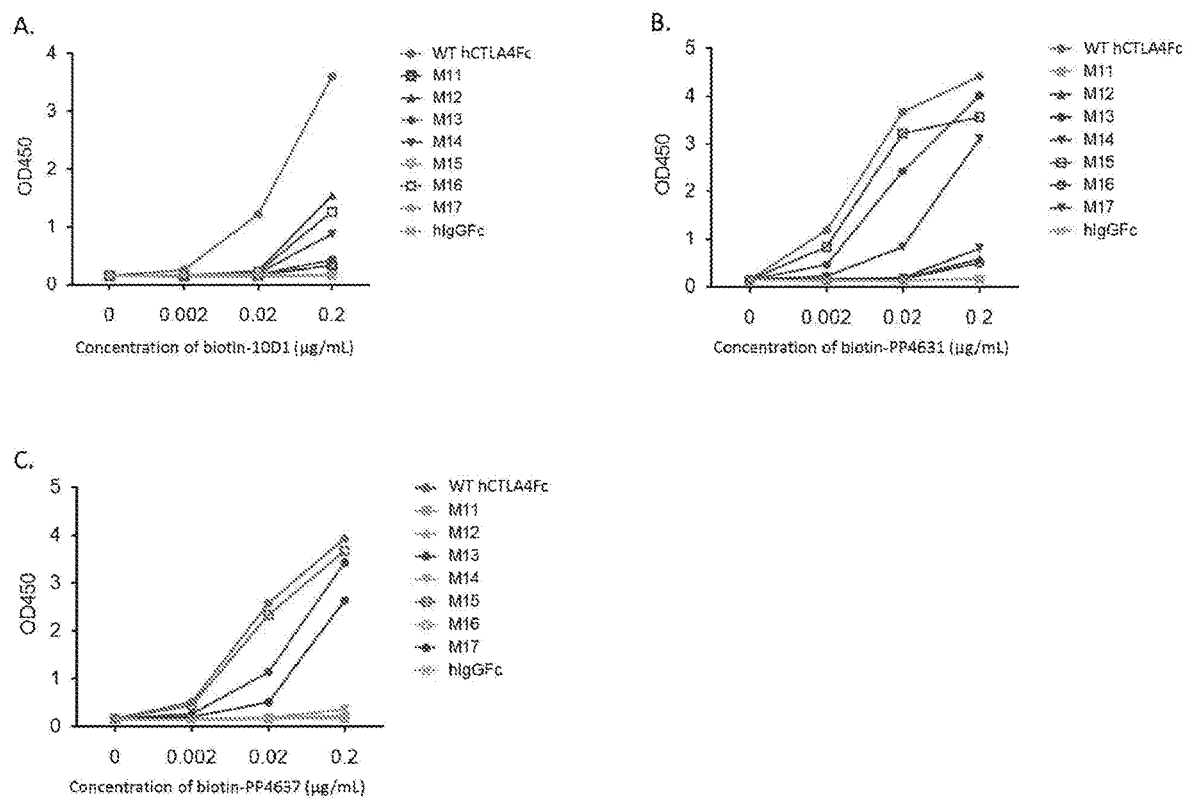

FIG. 57. Mutation in M11 (AA103-106, YLGI>fcGm) selectively abolish antibody binding to human CTLA-4. Data shown are means of duplicates, depicting the binding of B7-1 Fc (a), L3D10 (b), PP4631 (c), and PP4637 (d) binding to plate-coated hCTLA4-Fc (open circles), mCTLA4-Fc (filled triangles), M11 (filled circles) and IgG1-Fc (open triangles).

FIG. 58. Mapping L3D10, PP4631 and PP4637 to an epitope adjacent to the B7-1 binding site in a 3-D structure of the B7-1-CTLA4 complex. The B7-1 binding motif is colored in red, while the antibody epitope is colored in purple. B7-1 is depicted above CTLA4 with a space-filled ribbon, while that of CTLA-4 is depicted as an unfilled ribbon.

FIG. 59. Amino acid sequence composition of the WT (SEQ ID NO: 39) and mutant CTLA-4Fc proteins, M12-M17 (SEQ ID NOS: 51-56). DNA constructs encoding the 6 mutant CTLA-4Fc proteins, M12-M17, incorporating murine Ctla-4 amino acids were designed as shown. The amino acid sequences are for mature proteins, including the IgG1 Fc portion, but not the signal peptide. The known B7-1Ig binding site is shown in large blue letters and double-underlined. The replaced murine amino acid residues in the mutant are shown lower case in red. The IgG1 Fc portion of the proteins in underlined.

FIGS. 60A-C. Mutational analysis reveal distinct binding requirements for 10D1 (FIG. 60A), PP4631 (FIG. 60B) and PP4637 (FIG. 60C) to CTLA-4. CTLA-4Fc mutants were coated overnight at 4° C. at 1 µm/ml. After blocking with BSA, given concentration of biotinylated anti-CTLA-4 mAbs were added and incubated for 2 hours. After washing away the unbound antibodies, the bound antibodies were detected with HRP-labeled streptavidin.

Figure 61:
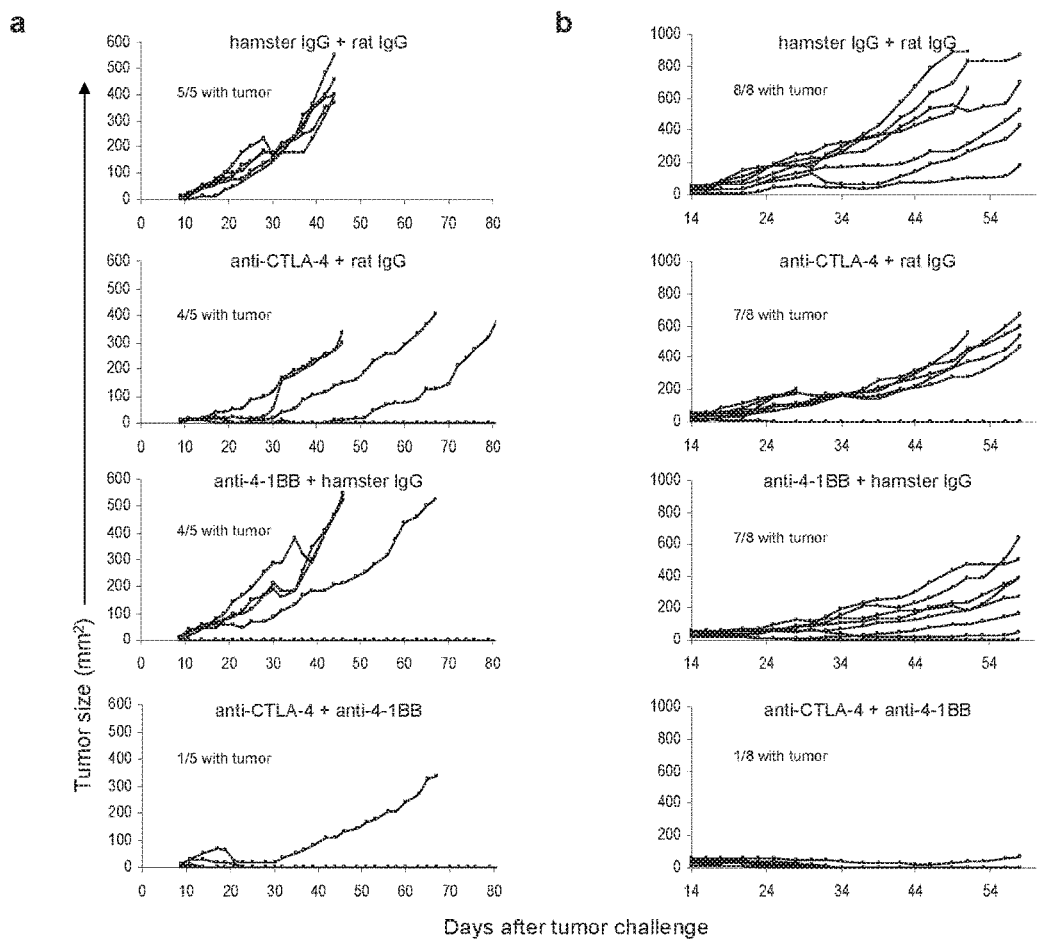

FIGS. 61A-B. Therapeutic effect of anti-4-1 BB and anti-CTLA-4 antibodies in both minimal disease (FIG. 61A) and established tumor (FIG. 61B) models. FIG. 61A shows therapy of minimal disease. C57BL/6 mice were inoculated subcutaneously with $5 \times 10^5$ MC38 cells. On days 2, 9 and 16 after tumor cell injection, control hamster and rat IgG, anti-CTLA-4, and/or anti-4-1 BB antibodies were injected. Tumor sizes were measured by physical examination. Data shown are growth kinetics of tumors, with each line representing tumor growth in one mouse. The sizes presented are products of long and short diameters of the tumor. FIG. 61B shows therapy of established tumors. As in FIG. 61A, except that therapy started on day 14 after tumor challenge; all mice had established tumors ranging from 9-60 $mm^2$ in size before treatment with mAbs was started. The combined effect of the two antibodies on established tumors has been repeated 3 times.

Figure 62:
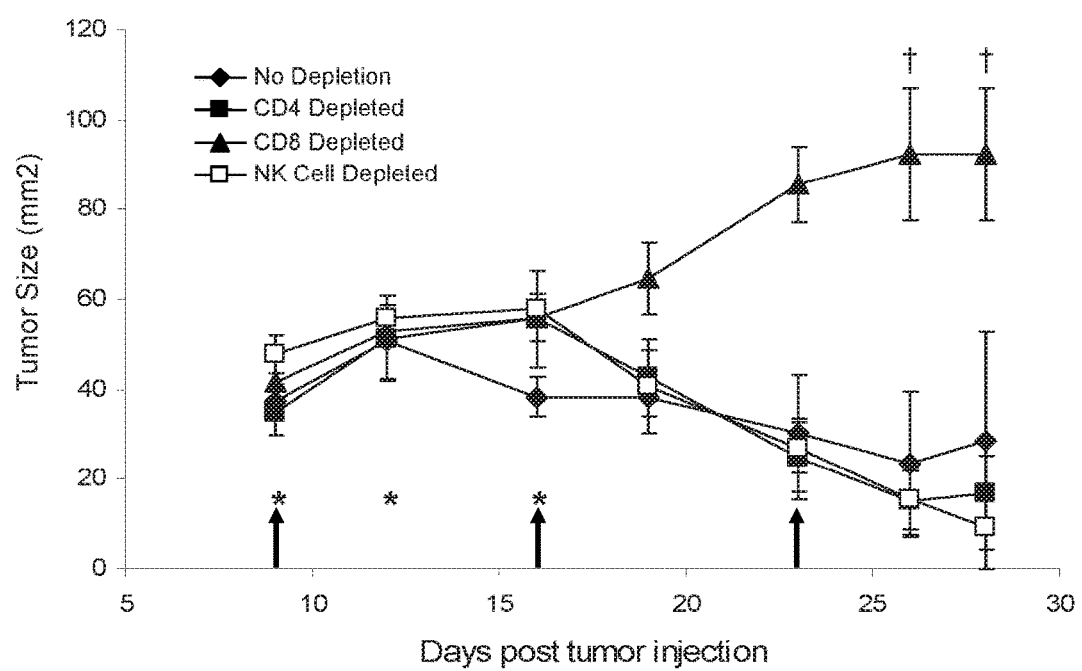

FIG. 62. CD8 T cells, but not CD4 or NK cells, are essential for antibody-induced tumor rejection. Tumor bearing mice were depleted of CD4, CD8, or NK cells by three injections of antibodies specific for either CD4, CD8 or NK1.1 on days 9, 12, and 16 after tumor cell inoculation (*). Therapeutic antibodies (anti-CTLA-4 plus anti-4-1 BB) were injected on days 9, 16 and 23 (vertical arrows). Data shown are means and SEM of tumor sizes (n=3). $P<0.05$ for CD8-depleted group compared to each of the other groups (†).

FIGS. 63A-B. Combination therapy reduced host response to anti-CTLA-4 antibodies. Hamster-anti-mouse-CTLA-4 (FIG. 63A) or rat-anti-mouse-4-1BB (FIG. 63B) antibodies were coated in ELISA plates. Different dilutions of sera from groups of 5 mice each were added to the plates. The relative amounts of antibody bound were determined using a secondary step reagent (biotinylated goat anti-mouse antibodies that were depleted of reactivity to rat and hamster IgG by absorption). Data shown are mean and SEM of optical density at 490 nm. Similar reduction of host antibody response to anti-CTLA-4 and 4-1 BB was observed when tumor-free mice were treated with the same antibodies (data not shown).

Figure 64:
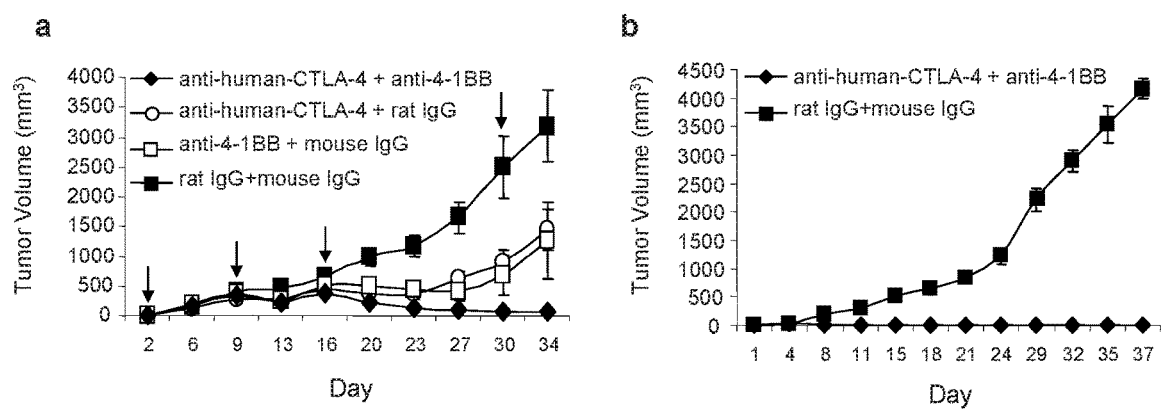

FIGS. 64A-B. Combination therapy with anti-4-1BB and L3D10 (anti-human-CTLA4) antibody in human CTLA-4 gene knock-in mice. FIG. 64A shows a therapeutic effect. Human CTLA4 knockin mice were inoculated with $5 \times 10^5$ MC38 tumor cells subcutaneously. Two days later, groups of 7 mice were treated with rat and mouse IgG, anti-4-1 BB and mouse IgG, L3D10 and rat IgG, or L3D10 and anti-4-1 BB, as indicated by the arrows. Data shown are mean tumor volume and SEM (n=7). All treatments significantly reduced tumor growth ($P<0.001$), and the double antibody treatment group show significantly reduce tumor size in comparison to either control ($P<0.0001$) or L3D10 antibody ($P=0.0007$) or anti-4-1 BB antibody treatment ($P=0.03$). All tumor bearing mice were sacrificed when the control IgG-treated group reached early removal criteria. FIG. 64B shows long-lasting immunity in mice that received combination therapy. Tumor-free mice in the double antibody-treated group developed long lasting immunity to MC38 tumors. At 110 days after the first tumor cell challenge, the double antibody-treated, tumor-free mice or control naïve mice were challenged with $5 \times 10^5$ tumor cells subcutaneously. Tumor growth was monitored by physical examination. Note that all of the mice that rejected the tumors in the first round were completely resistant to re-challenge, while all naïve mice had progressive tumor growth.

DEFINITIONS

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; ref. 44) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Ref. 45). "Framework Region" or "FR" residues are those variable domain residues other than the hypervariable region residues as herein defined. The term antibody includes monoclonal antibodies, multispecific antibodies, human antibodies, humanized antibodies, synthetic antibodies, chimeric antibodies, camelized antibodies, single chain antibodies, disulfide-linked Fvs (sdFv), intrabodies, and anti-idiotypic (anti-Id) antibodies (including, e.g., anti-Id and anti-anti-Id antibodies to antibodies of the invention). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antigen binding fragment" of an antibody refers to one or more portions of an antibody that contain the antibody's Complementarity Determining Regions ("CDRs") and optionally the framework residues that comprise the antibody's "variable region" antigen recognition site, and exhibit an ability to immunospecifically bind antigen. Such fragments include Fab', F(ab').sub.2, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, chimeric or humanized antibodies are particularly preferred for in vivo use in humans, however, murine antibodies or antibodies of other species may be advantageously employed for many uses (for example, in vitro or in situ detection assays, acute in vivo use, etc.).

A "chimeric antibody" is a molecule in which different portions of the antibody are derived from different immunoglobulin molecules such as antibodies having a variable region derived from a non-human antibody and a human immunoglobulin constant region. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; 46-48), and chain shuffling (U.S. Pat. No. 5,565,332).

The invention particularly concerns "humanized antibodies". As used herein, the term "humanized antibody" refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. One says that the donor antibody has been "humanized," by the process of "humanization," because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an Fc.gamma.RIIB polypeptide, that has been altered by the introduction of amino acid residue substitutions, deletions or additions (i.e., mutations).

DETAILED DESCRIPTION

An antibody against human CTLA4 protein, Ipilimumab, has been shown to increase survival of cancer patients, either as the only immunotherapeutic agent or in combination with other therapeutic agents such as, for example without limitation, an anti-PD-1 antibody (13-15). However, the therapeutic effect is associated with significant adverse effects (13-18). There is a great need to develop novel anti-CTLA4 antibodies to achieve better therapeutic effect and/or less autoimmune adverse effect.

The inventors have discovered an anti-CTLA4 antibody that, surprisingly, can be used to induce cancer rejection while also reducing autoimmune adverse effects associated with immunotherapy.

Provided herein are antibody compositions of matter and antigen-binding fragments thereof. The invention further concerns the embodiment of such molecules wherein the molecule is a monoclonal antibody, a human antibody, a chimeric antibody or a humanized antibody.

In detail, the invention provides a molecule, comprising an antigen-binding fragment of an antibody that immunospecifically binds to CTLA4, and in particular human CTLA4, preferably expressed on the surface of a live cell at an endogenous or transfected concentration. The invention particularly concerns the embodiment of such a molecule wherein the antigen-binding fragment binds to CTLA4, and wherein the live cell is a T cell.

The present invention relates to antibodies and their antigen-binding fragments that are capable of immunospecifically binding to CTLA4. In some embodiments such molecules are additionally capable of blocking the binding of B7.1 and B7.2 to CTLA4.

The invention further concerns the embodiment of such molecules wherein the molecule is a monoclonal antibody, a human antibody, a chimeric antibody or a humanized antibody. The invention includes the embodiments wherein such antibodies are monospecific, bispecific, trispecific or multispecific.

The invention further concerns the embodiment of such molecules or antibodies which binds to CTLA4, and wherein the antigen-binding fragment thereof comprises six CDRs, wherein the CDRs comprise the CDRs of anti-CTLA4 antibody L3D10. Specifically, the antibody comprises the three light chain and the three heavy chain CDRs of anti-CTLA4 antibody L3D10.

The invention further concerns the embodiment of the above-described antibodies, wherein the antibody is detectably labeled or comprises a conjugated toxin, drug, receptor, enzyme, receptor ligand.

The invention further concerns a pharmaceutical composition comprising a therapeutically effective amount of any of the above-described antibody compositions, and a physiologically acceptable carrier or excipient. Preferably, compositions of the invention comprise a prophylactically or therapeutically effective amount of humanized antibodies of the invention and a pharmaceutically acceptable carrier In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers may be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, may also contain minor amounts of wetting or emulsifying agents, or pH buffering agents. These compositions may take the form of solutions, suspensions, emulsion, tablets, pills, capsules, powders, sustained-release formulations and the like.

Generally, the ingredients of compositions of the invention may be supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline may be provided so that the ingredients may be mixed prior to administration.

The compositions of the invention may be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention further concerns the use of the antibody compositions described here and pharmaceutical compositions thereof for the upregulation of immune responses. Up-modulation of the immune system is particularly desirable in the treatment of cancers and chronic infections, and thus the present invention has utility in the treatment of such disorders. As used herein, the term "cancer" refers to a neoplasm or tumor resulting from abnormal uncontrolled growth of cells. As used herein, cancer explicitly includes leukemias and lymphomas. The term refers to a disease involving cells that have the potential to metastasize to distal sites.

Accordingly, the methods and compositions of the invention may also be useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, sarcoma, melanoma, or leukemia is treated or prevented by the methods and compositions of the invention.

In another embodiment of the invention, the antibody compositions and antigen binding fragments thereof can be used with other anti-tumor therapies, including but not limited to, current standard and experimental chemotherapies, hormonal therapies, biological therapies, immunotherapies, radiation therapies, or surgery. In some embodiments, the molecules of the invention may be administered in combination with a therapeutically or prophylactically effective amount of one or more agents, therapeutic antibodies or other agents known to those skilled in the art for the treatment and/or prevention of cancer, autoimmune disease, infectious disease or intoxication. Such agents include for example, any of the above-discussed biological response modifiers, cytotoxins, antimetabolites, alkylating agents, antibiotics, or anti-mitotic agents, as well as immunotherapeutics.

In preferred embodiment of the invention, the antibody compositions and antigen binding fragments thereof can be used with other anti-tumor immunotherapies. In such an embodiment the molecules of the invention are administered in combination with molecules that disrupt or enhance alternative immunomodulatory pathways (such as TIM3, TIM4, OX40, CD40, GITR, 4-1-BB, B7-H1, PD-1, B7-H3, B7-H4, LIGHT, BTLA, ICOS, CD27 or LAG3) or modulate the activity of effecter molecules such as cytokines (e.g., IL-4, IL-7, IL-10, IL-12, IL-15, IL-17, GF-beta, IFNg, Flt3, BLys) and chemokines (e.g., CCL21) in order to enhance the immunomodulatory effects. Specific embodiments include a bi-specific antibody comprising the anti-CTLA4 antibody compositions described herein and anti-PD-1 (pembrolizumab (Keytruda) or Nivolumab (Opdivo)), anti-B7-H1 (atezolizumab (Tecentriq) or durvalumab), anti-B7-H3, anti-B7-H4, anti-LIGHT, anti-LAG3, anti-TIM3, anti-TIM4 anti-CD40, anti-OX40, anti-GITR, anti-BTLA, anti-CD27, anti-ICOS or anti-4-1 BB. In yet another embodiment, the molecules of the invention are administered in combination with molecules that activate different stages or aspects of the immune response in order to achieve a broader immune response. In more preferred embodiment, the antibody compositions and antigen binding fragments thereof are combined with anti-PD-1 or anti-4-1 BB antibodies, without exacerbating autoimmune side effects.

Another embodiment of the invention includes a bi-specific antibody that comprises an antibody that binds to CTLA4 bridged to an antibody that binds another immune stimulating molecules. Specific embodiments include a bi-specific antibody comprising the anti-CTLA4 antibody compositions described herein and anti-PD-1, anti-B7-H1, anti-B7-H3, anti-B7-H4, anti-LIGHT, anti-LAG3, anti-TIM3, anti-TIM4 anti-CD40, anti-OX40, anti-GITR, anti-BTLA, anti-CD27, anti-ICOS or anti-4-1 BB. The invention further concerns of use of such antibodies for the treatment of cancer.

Methods of administering the antibody compositions of the invention include, but are not limited to, parenteral administration (e.g., intradermal, intramuscular, intraperitoneal, intravenous and subcutaneous), epidural, and mucosal (e.g., intranasal and oral routes). In a specific embodiment, the antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

Yet another embodiment of the invention concerns monitoring the blocking effects of anti-CTLA4 antibodies in vivo by monitoring the expression levels of B7.1 and B7.2 on immune cells such as antigen presenting cells (APCs). CTLA4 is expressed predominately among the Treg where it suppresses autoimmune diseases by down-regulating B7-1 and B7-2 expression on APCs such as dendritic cells. Therefore, upregulation of B7 molecules, B7.1 and B7.2, can be as readouts for the in vivo blockade of B7-CTLA4 interactions. In a specific embodiment, peripheral or intratumoral immune cells are removed from the subject before and after anti-CTLA4 treatment and assayed ex vivo for a reduction in the level of B7.1 and/or B7.2 on the surface of the immune cell, wherein the presence of blocking anti-CTLA4 antibodies prevents B7.1/B7.2 binding by endogenous CTLA4, which in turn prevents the downregulation of B7.1 and B7.2, resulting in a net increase in B7.1/B7.2 expression. In a preferred embodiment the level of B7.1 and B7.1 is measured on antigen presenting cells. In a most preferred embodiment the level of B7.1 and B7.1 is measured on dendritic cells.

In a further embodiment, the change (reduction) in B7.1 and B7.2 on immune cells following anti-CTLA4 treatment is used as a biomarker for measuring the biological activity of anti-CTLA4 antibodies in vivo and monitoring patent responses to anti-CTLA4 treatment by measuring the level B7.1 and/or B7.2 expression on immune cells, and comparing the level of expression before and after treatment. In a preferred embodiment the level of B7.1 and/or B7.2 expression is monitored over time during a course of anti-CTLA4 therapy.

EXAMPLES

Example 1. Generation of Chimeric Anti-CTLA4 Antibody

Using human CTLA4 gene knock-in mice and hu-PBL-Scid mice, it was previously demonstrated that mouse anti-human CTLA4 antibodies reduced tumor growth, and identify L3D10 as the most effective among the panel of mAbs tested. However, none of the antibodies obtained was able to achieve complete tumor rejection, even when used at relatively high doses of (>10 mg/kg) and before formation of palpable tumors (as early on day 2) after tumor cell challenge (19-21).

Figure 1:
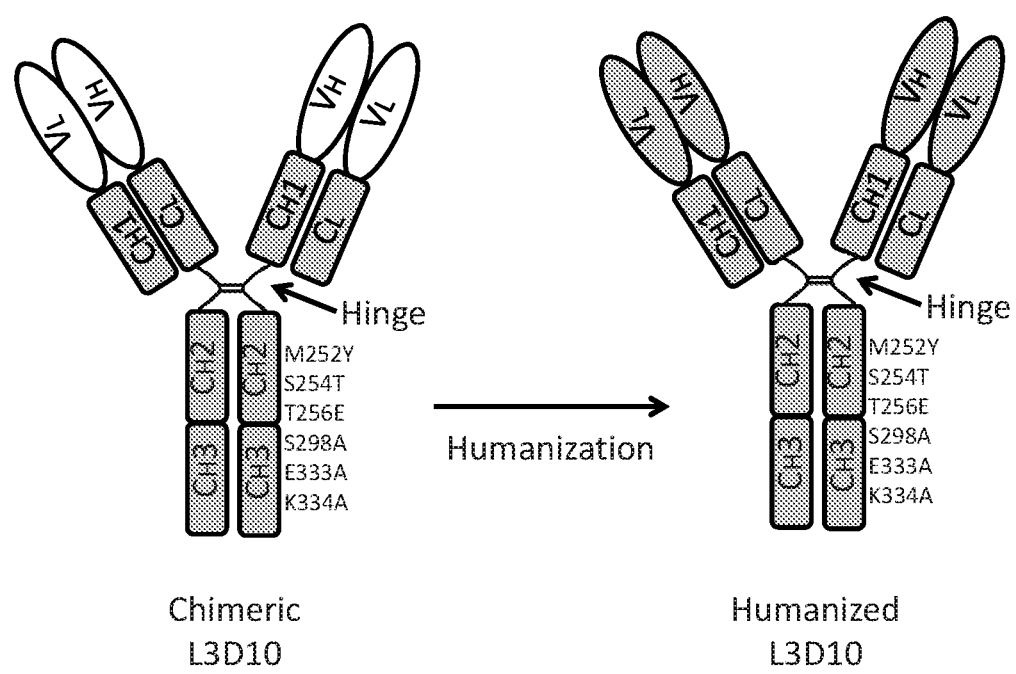
FIG. 1. Schematic diagram of the chimeric (left) and humanized (right) L3D10 antibodies with a novel combination of mutations in the IgG1 Fc region. The positions of the mutations in the Fc region are identified by their amino acid position number and the amino acids are identified by their single letter code, with the letter before the number representing the replace amino acid and the letter after the number representing the introduced amino acid. The variable region of the antibodies is depicted with open ovals and the human sequence is depicted with gray rectangles. V=variable region; C=constant region; L=light chain; H=heavy chain.

Since the mouse antibodies were of IgG1 subclass that does not have strong antibody-dependent cellular cytotoxicity (ADCC), and since ADCC maybe involved in tumor rejection, the Fc of the mAb was modified in several ways, to achieve better immunotherapeutic effect. First, mouse IgG1, which is weak in ADCC, was replaced to produce a chimeric antibody with human IgG1, which has strong ADCC activity. Second, based on known art in the literatures (22), three mutations (S298A, E333A and K334A) were introduced in the CH to increase ADCC activity. Third, three mutations (M252Y, S254T and T256E) were introduced to increase the half-life of the antibody in vivo (23). The design of the new chimeric antibody is depicted in FIG. 1, left panel.

To engineer the antibody, the variable regions of L3D10 hybridoma were first identified through DNA sequencing using standard methods known in the art. The nucleotide sequences were translated into amino acids listed in SEQ ID NO: 1 and SEQ ID NO: 2. The normal human IgG1 Fc sequence and the mutant Fc sequence are disclosed in SEQ ID NO: 3 and SEQ ID NO: 4, respectively. The amino acid and codon optimized nucleotide sequences of heavy and light chain sequences are disclosed in SEQ ID NOS: 5-8.

DNA corresponding to SEQ ID NO: 5 and SEQ ID NO: 7 were synthesized and inserted into expression vectors, and the vectors were transfected with the designed sequence into HEK293 cells. Briefly, HEK293 cells were seeded in a shake flask one day before transfection, and were grown using serum-free chemically defined media. The DNA expression constructs were transiently transfected into 0.5 liter of suspension HEK293 cells using standard operating procedure for transient transfection. After 20 hours, cells were sampled to obtain the viability and viable cell count, and titer was measured (Octet QKe, ForteBio). Additional readings were taken throughout the transient transfection production runs. The culture was harvested at day 5. The conditioned media for L3D10 was harvested and clarified from the transient transfection production run by centrifugation and filtration. The supernatant was run over a Protein A column and eluted with a low pH buffer. Filtration using a 0.2 μm membrane filter was performed before aliquoting. After purification and filtration, the protein concentration was calculated from the OD280 and the extinction coefficient. A total of 43.2 mg of Ig proteins were obtained from one round of transfection.

Example 2. Chimeric L3D10 Antibody Binding Sites Only Partially Overlap with 10D1

Figure 2:
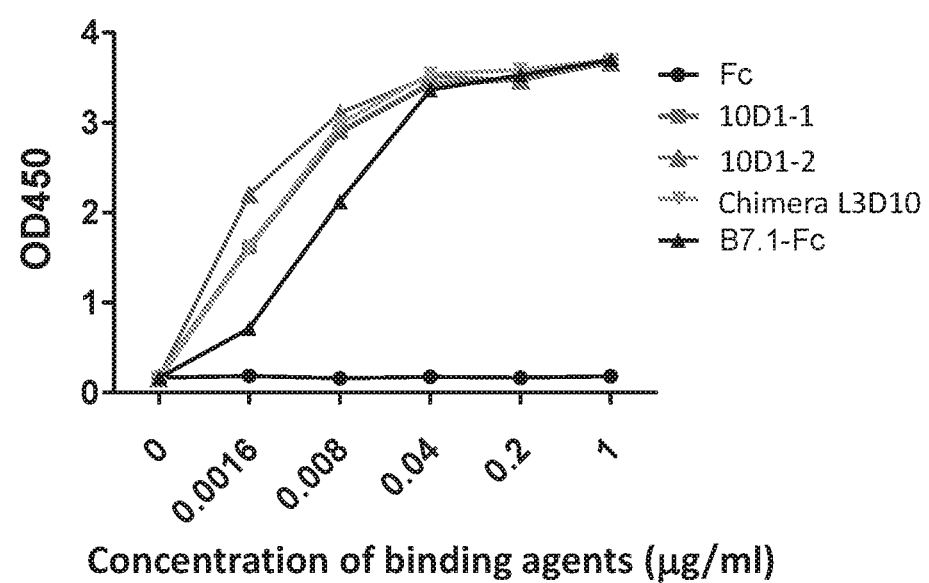
FIG. 2. CTLA4 Binding of chimeric L3D10 and 10D1 to plate immobilized CTLA4, as determined by ELISA. ELISA plates were coated with 1 μg/ml of CTLA4-His protein (Sino Biological, China). The given concentration of biotinylated binding proteins were added and binding was measured using HRP-conjugated streptavidin. 10D1-1 and -2 are two independent material lots of the same antibody. B7.1-Fc is a positive control and Fc is a negative control.
Figure 3:
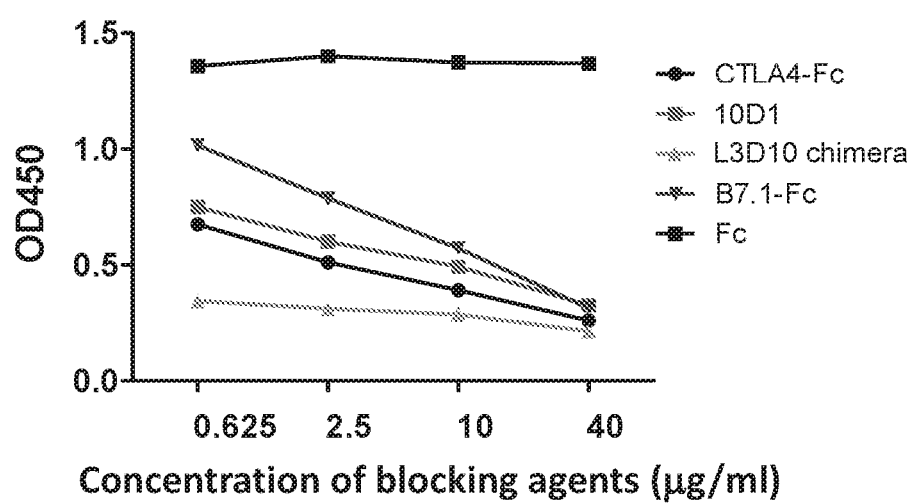
FIG. 3. L3D10 competition assay. 10D1 is less efficient in blocking chimeric L3D10 binding to CTLA4 than chimeric L3D10. The experiment was performed as in FIG. 2, except that biotinylated chimeric L3D10 was mixed with the given concentration of unlabeled CTLA4-binding proteins or CTLA4-Fc prior to adding to the ELISA plates. Note much better blocking by unlabeled L3D10 than 10D1, which suggest that these antibody binding sites are not identical.

In the clinic, the anti-CTLA4 antibody, Ipilimumab, has been shown to improve the survival of cancer patients but induce significant autoimmune adverse effect. In order to evaluate the comparative binding sites of the chimeric L3D10 antibody and 10D1, binding to CTLA4 and the ability of the antibodies to compete for binding to CTLA4 were compared. While both antibodies bind to immobilized CTLA4 proteins at comparable efficiency (FIG. 2), 10D1 does not completely block chimeric L3D10 binding to CTLA4 (FIG. 3). As expected, unlabeled L3D10 completely blocks labeled L3D10 binding, indicating that the antibody binding sites of L3D10 and 10D1 only partially overlap.

Example 3. More Efficient Blockade CTLA4:B7.1 and CTLA4:B7.2 Interactions by Chimeric L3D10 Antibody Than by 10D1

Figure 4:
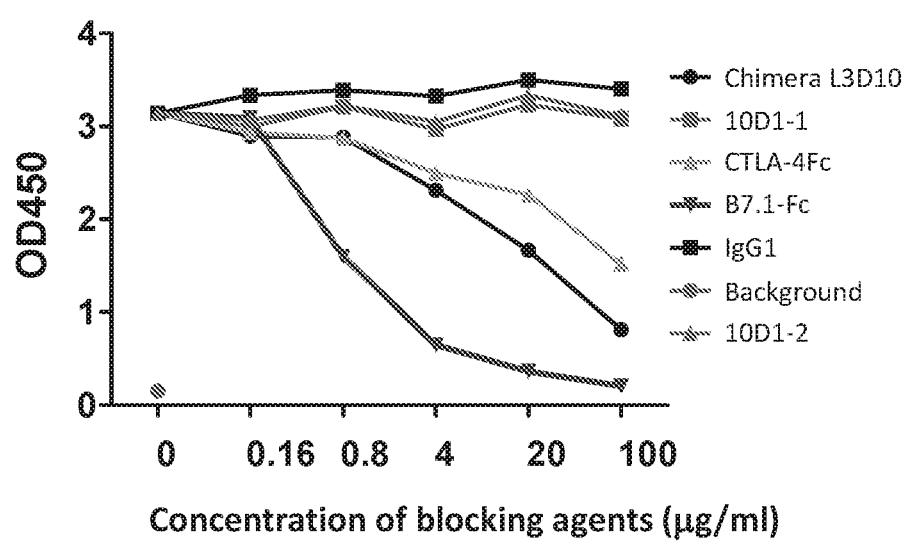
FIG. 4. Blocking CTLA4 binding to plate immobilized B7.1. B7.1 Fc protein was coated onto ELISA plates at 0.5 μg/ml. After washing and blocking, biotinylated CTLA4-Fc protein was added at 0.25 μg/ml in the presence of given concentrations of the competing proteins. Data shown are means of duplicate optical density at 405 nM. Whereas B7.1-Fc, chimeric L3D10 and CTLA4-Fc all block the CTLA4:B7.1 interaction in a dose-dependent manner, two separate lots of 10D1 antibody failed to block at all doses tested. Biotinylation of CTLA4 does not destroy 10D1 epitopes on CTLA4 as both lots of 10D1 show strong binding to biotinylated CTLA4 (data not shown).
Figure 5:
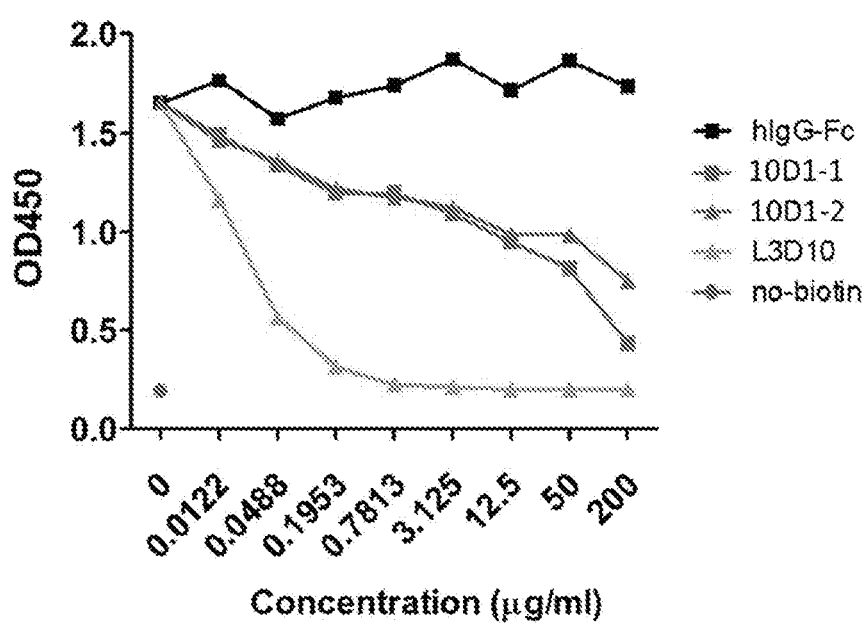
FIG. 5. Blocking CTLA4 binding to plate immobilized B7.2. B7.2Fc protein was coated onto ELISA plates at 0.5 μg/ml. After washing and blocking, biotinylated CTLA4-Fc protein was added at 0.25 μg/ml in the presence of given concentrations of the competing proteins. Whereas chimeric L3D10 blocks the CTLA4:B7.2 interaction in a dose-dependent manner, two separate lots of 10D1 antibody failed to completely block the CTLA4:B7.2 interaction even at the highest concentration.
Figure 6:
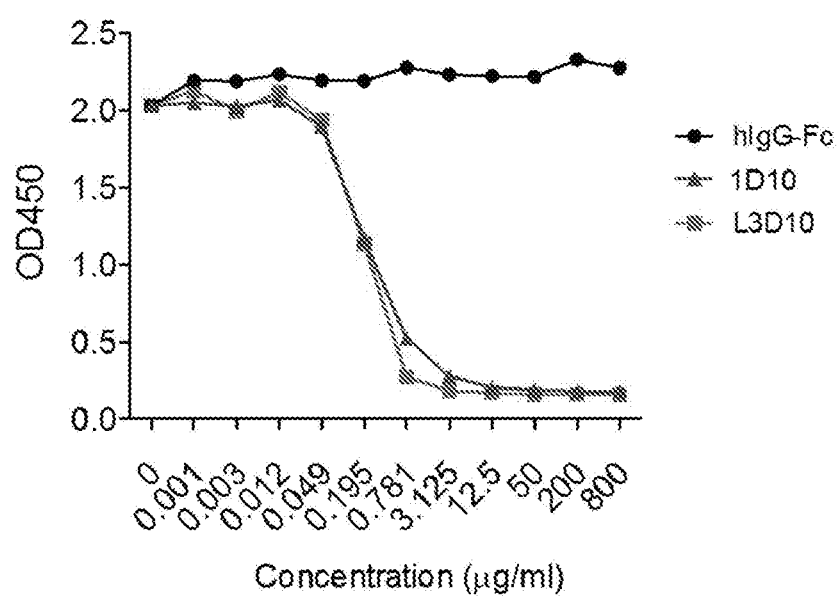
FIG. 6. Both 10D1 and L3D10 potently block B7-CTLA4 interaction using soluble B7-1 and B7-2 and immobilized CTLA4-Fc. Varying doses of anti-human CTLA4 mAbs were added along with 0.25 μg/ml of biotinylated human CTLA4-Fc to plate-coated with human B7-1 Fc. The amounts of CTLA4 bound to plates were measured using HRP-conjugated streptavidin. Data shown are means of duplicates and are representative of two independent experiments.

It has been reported that anti-human CTLA4 mAb, 10D1, can block B7-CTLA4 interaction if soluble B7-1 and B7-2 was used to interact with immobilized CTLA4 (49). Since B7-1 and B7-2 function as cell surface co-stimulatory molecules, we evaluated the ability of anti-CTLA4 antibodies to block the B7-CTLA4 interaction using immobilized B7-1 and B7-2. Using a competitive ELISA assay format, the abilities of L3D10 and 10D1 to block binding of the CTLA4 fusion protein, CTLA4-Ig, to both plate-immobilized- and cell membrane-expressed B7.1 and B7.2. For these experiments a chimeric anti-human CTLA4-mAb with an affinity (2.3 nM) that is similar to 10D1 (4 nM) (49) was used. For the plate immobilized assays, B7.1 Fc or B7.2Fc were coated onto the ELISA plate at 1 µg/ml over night at 4° C. or 2 hours at 37° C. Biotinylated CTLA4-Fc were mixed with given concentrations of either B7.1-Fc, 10D1 or chimeric L3D10. The amounts of the CTLA4-Fc bound to B7.1 on the plate is determined using horse-radish peroxidase-conjugated streptavidin. As shown in FIG. 4, while chimeric L3D10, B7.1 Fc and CTLA4-Fc all efficiently blocked CTLA4-Fc:B7.1 interaction, two separate material lots of 10D1 failed to block the interaction. L3D10 shows significant blocking of plate-immobilized B7.1 binding at concentrations as low as 0.2 µg/ml, achieving 50% inhibition ($IC_{50}$) at around 3 µg/ml. Similarly, L3D10 blocked binding of CTLA4-Fc binding to plate immobilized B7.2 with an $IC_{50}$ of 0.03 µg/ml, whereas 10D1 from two different material lots displayed minimal blocking with an $IC_{50}$ of approximately 200 µg/ml (FIG. 5). However, consistent with the previous report (49), antibody 10D1 potently inhibited B7-1-CTLA4 interaction in the reverse experiment when plate immobilized CTLA4 is used to interact with soluble B7-1 (FIG. 6).

Figure 7:
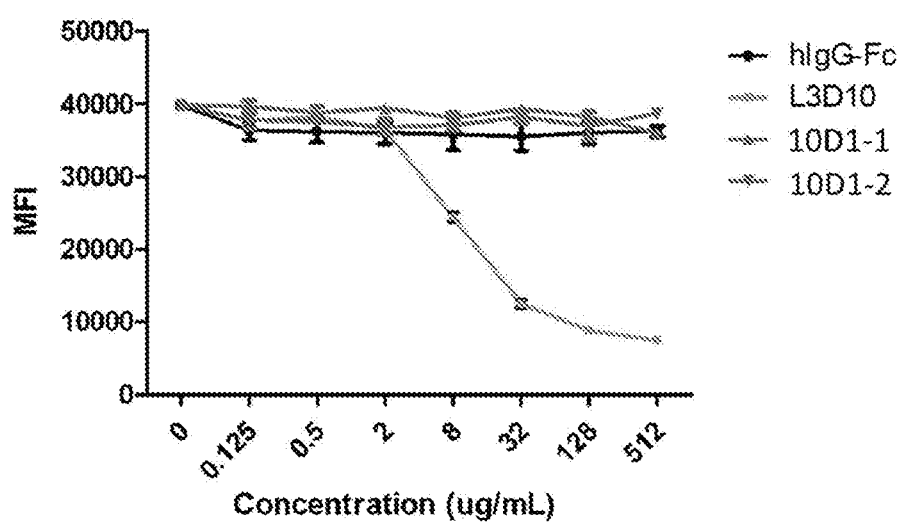
FIG. 7. Blocking CTLA4 binding to cell surface expressed B7.1. Biotinylated CTLA4-Fc protein was added to B7.1 expressing CHO cells at 0.5 μg/ml in the presence of the given concentration of the competing proteins. Binding of biotinylated fusion protein to CHO cells transfected with mouse or human B7-1 and B7-2 was detected by flow cytometry. The amounts of bound receptors were measured using phycoethrythorin-conjugated streptavidin. Data shown are means fluorescence intensity of triplicate samples. Whereas chimeric L3D10 blocks the CTLA4:B7.1 interaction in a dose-dependent manner, two separate lots of 10D1 antibody failed to block at all doses tested.
Figure 8:
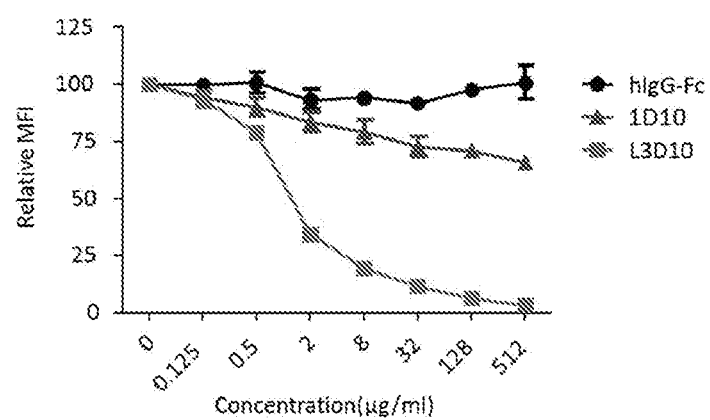
FIG. 8. Blocking CTLA4 binding to cell surface expressed murine B7.1. Modest but detectable blocking of mouse B7-1-human CTLA4 interaction by 10D1 when mB7-1 is expressed on CHO cells. Varying doses of anti-human CTLA4 mAbs were added along with 0.25 μg/ml of human CTLA4-Fc to CHO cells expressing mouse B7-1. Data shown are means and SEM or triplicate data and are representative of two independent experiments.
Figure 9:
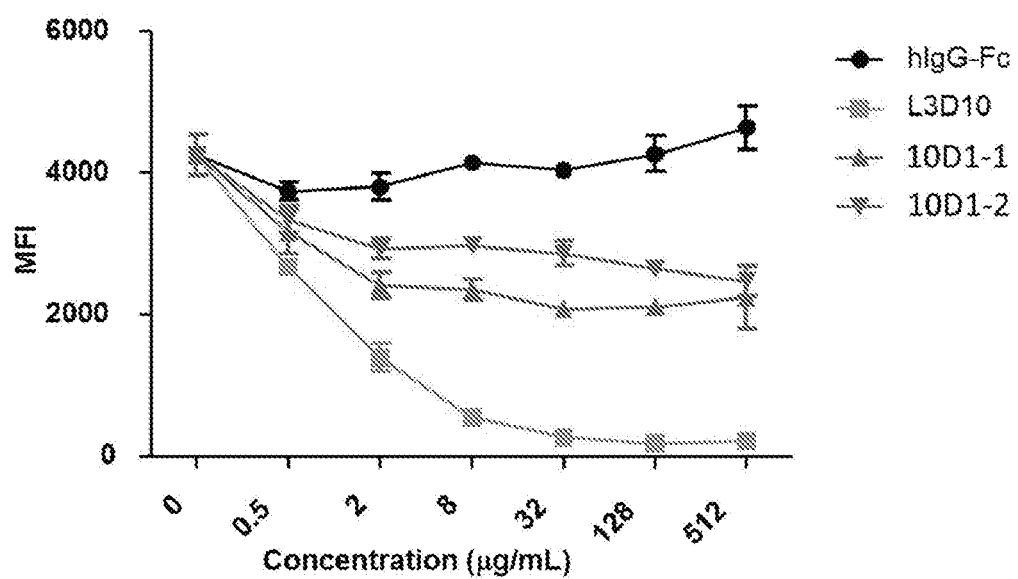
FIG. 9. Blocking CTLA4 binding to cell surface expressed B7.2. Biotinylated CTLA4-Fc protein was added to B7.2 expressing CHO cells at 0.5 μg/ml in the presence of the given concentration of the competing proteins. Whereas chimeric L3D10 blocks the CTLA4:B7.2 interaction in a dose-dependent manner, two separate lots of 10D1 antibody failed to completely block the CTLA4:B7.2 interaction even at the highest concentration. Data shown in this figure has been repeated at least 5 times.

For the cell membrane protein binding experiments, when B7.1 is expressed on the surface of CHO cells, L3D10 blocks binding of CTLA4-Fc but 10D1 from two different material lots did not, even when used at 512 µg/ml (FIG. 7). While much less potent than L3D10, high doses of 10D1 achieved approximately 25% blocking between human CTLA4 and mouse B7-1 (FIG. 8). For B7.2 expressed on the CHO cell surface, L3D10 was again blocking whereas 10D1 was only partially blocking, with less than 50% inhibition observed even when 10D1 was used at 512 µg/ml (FIG. 9).

A potential caveat is that biotinylation may have affected binding of 10D1 to CTLA4-Fc. To address this issue, we compared binding of L3D10 and 10D1 to biotinylated CTLA4-Fc used in the blocking studies. As shown in FIG. 10, 10D1 is more effective than L3D10 in binding the biotinylated CTLA4-Fc. Therefore, the failure in blockade by 10D1 was not due to insufficient binding to biotinylated CTLA4-Fc. A similar pattern is observed when polyhistidine-tagged CTLA4 was used to interact with human B7-1 transfected CHO cells (FIG. 11). Taken together, our data suggest that ability of antibody 10D1 to block B7-CTLA4 interaction is highly dependent on the assay employed, with minimal to no detectable blocking activity if B7-1 and B7-2 are immobilized, while antibody L3D10 is a robust blocker for B7-CTLA4 interaction regardless of whether the B7 protein is immobilized.

Example 4. Chimeric L3D10 Antibody is More Efficient than Unmodified L3D10 in Causing Tumor Rejection It was previously reported that mouse L3D10 failed to cause complete remission of MC38 tumors, even though significant delays were observed (19, 20). To determine if chimeric L3D10 can cause complete remission in syngeneic mice, 1×10⁶ MC38 tumor cells were transplanted into syngeneic C57BL/6 mice. One week later, when the tumor reaches around 5 mm in diameter, mice were treated with either control IgG or chimeric L3D10 mAb at a dose that is only half of what was used in the previous studies with the mouse L3D10. As shown in FIG. 12, despite possible immunogenity of the human Ig sequence, it was found that the chimeric L3D10 caused complete remission in all mice tested. Since the treatment was initiated when large tumor burdens have been established, which is much more difficult than when tumors were not palpable (19), these experiments show that chimeric L3D10 is more efficient than unmodified L3D10.

Example 5. Chimeric L3D10 Antibody has Equivalent Activity as 10D1 in Causing Tumor Rejection The availability of human CTLA4 gene knockin mice (20) provided with an unprecedented opportunity to test biological activity of the chimeric anti-human CTLA-4 antibody with clinically used anti-CTLA-4 mAb, 10D1. In this humanized mouse model, a CTLA4 gene encoding a product with 100% identity to human CTLA-4 protein is expressed under the control of endogenous mouse Ctla4 locus When the anti-tumor activity of the chimeric L3D10 and 10D1 were directly compared in the MC38 tumor model in human CTLA4-knockin mice, it is clear that both antibodies were comparable in causing tumor rejection, whereas the tumors grew progressively in IgG control group. FIG. 13 shows the results of antibody treatment on tumor size from duplicate experiments.

An interesting question is whether anti-CTLA-4 mAbs need to interact with all CTLA-4 (i.e. achieve target saturation) in order to exert immunotherapeutic effect. F1 mice from $CTLA4^{h/h}$ and $CTLA4^{m/m}$ mice expresses both mouse and human CTLA-4 protein in a co-dominant manner. Interestingly, as shown in FIG. 14, both chimeric L3D10 and 10D1 effectively induced tumor rejection, even though approximately 50% of the CTLA-4 protein (i.e. the murine version of the protein) cannot be bound by anti-human CTLA-4 mAbs. Importantly, L3D10 is more therapeutically effective than 10D1 in this setting i.e. when gene doses are limited ($P<0.05$).

Previous studies have demonstrated that anti-mouse Ctla-4 mAbs cannot induce rejection of melanoma cell line B16-F1 without combination with other therapeutic modalities. Therefore, the anti-tumor effect of the chimeric L3D10 and 10D1 antibodies was also tested using this more challenging B16 tumor model in the human CTLA4 knockin mice. As shown in FIG. 15, whereas neither L3D10 nor Ipilimumab were capable of causing rejection of established tumors, both cause statistically significant retardation of tumor growth, while the differences between different antibodies are not statistically significant.

Example 6. CTLA4 Blocking In Vivo

CTLA4 is expressed predominately among the Treg where it suppresses autoimmune diseases by down-regulating B7-1 and B7-2 expression on dendritic cells (50). Since targeted mutation of Ctla4 (50) and treatment with blocking anti-CTLA4 mAb (51) upregulated expression of B7-1 and B7-2 on dendritic cells, it has been suggested that physiological function of CTLA4 on Treg is to down-regulate B7 on DC. Therefore, upregulation of B7 was used as a readout for the in vivo blockade of B7-CTLA4 interactions and developed an assay using T cells from the $Ctla4^{h/h}$ mice which had homozygous knockin of the human CTLA4 gene.

As outlined in FIG. 16, surface expressed B7.1 or B7.2 binds CTLA4 on the surface of T cells, which leads to a downregulation in B7.1 and B7.2 expression. However, binding of blocking anti-CTLA4 antibodies prevents B7.1/B7.2 binding, which prevents the downregulation of B7.1 and B7.2, resulting in a net increase in B7.1/B7.2 expression. However, with chimeric T cells expressing both human and mouse CTLA4, antibodies that bind human CTLA4 do not prevent B7.1/B7.2 binding to the murine CTLA4, which restores B7.1/B7.2 inhibition.

CTLA4 humanized mice that express the CTLA4 gene with 100% identify to human CTLA4 protein under the control of endogenous mouse Ctla4 locus has been described (20). The homozygous knock-in mice (CTLA4$^{h/h}$) were backcrossed to C57BL/6 background for at least 10 generations. Heterozygous mice (CTLA4$^{h/m}$) were produced by crossing the CTLA4$^{h/h}$ mice with WT BALB/c mice.

To test clinically proven therapeutic anti-CTLA4 mAb, 10D1, we injected very high doses of anti-CTLA4 mAb (500 µg/mouse, which is roughly 25 mg/kg or 8-times the highest dose used in the clinic) into Ctla4$^{h/h}$ or Ctla4$^{m/h}$ mice and harvested spleen cells to measure levels of B7-1 and B7-2 on Cd11c$^{hi}$ DC at 24 hours after injection (FIGS. 17A-B). As shown FIGS. 17C-E, in comparison to Ctla4$^{h/h}$ mice that received human IgG1-Fc, DC from chimeric L3D10 treated mice had a statistically significant increase in B7.1 expression in T cells expressing human CTLA4 but not in T cells expressing both human and mouse CTLA4. Similar results were seen for B7.2 as shown in FIGS. 17C-E. The magnitude of upregulation in B7-2 is comparable to what was achieved using a blocking anti-CTLA4 mAb in human Treg-DC co-culture (66).

To further confirm the specificity of the in vivo assay, we tested if L3D10 can upregulate B7 in Ctla4$^{m/h}$ mice in which mouse and human CTLA4 are expressed co-dominantly. Since at least 50% of the CTLA4 does not bind to anti-human CTLA4 antibodies, it is expected that they would be less potent in blocking B7-CTLA4 interaction. Indeed, neither antibody caused upregulation of B7-1 and B7-2 on DC from Ctla4$^{m/h}$ mice (FIG. 17C, D, F). The complete lack of blockade by L3D10 in the Ctla4$^{m/h}$ mice suggests that CTLA4 encoded by the mouse allele, which does not bind to L3D10 (FIG. 18), is sufficient to down-regulate B7 expression. Thus, our data demonstrated that at doses that are at least 8-times higher than the highest dose used in clinic, 10D1 does not block B7-CTLA4 interaction when B7 are either immobilized on plate or anchored on cell membrane, both in vivo and in vitro.

The complete lack of blockade by L3D10 in the Ctla4$^{m/h}$ mice suggests that CTLA4 encoded by the mouse allele, which does not bind to L3D10 (FIG. 18), is sufficient to down-regulate B7 expression. In contrast, 10D1 did not increase B7.1 or B7.2 expression. According to the model, this suggests that L3D10 blocks CTLA4 activity in vivo whereas 10D1 does not.

Figure 20:
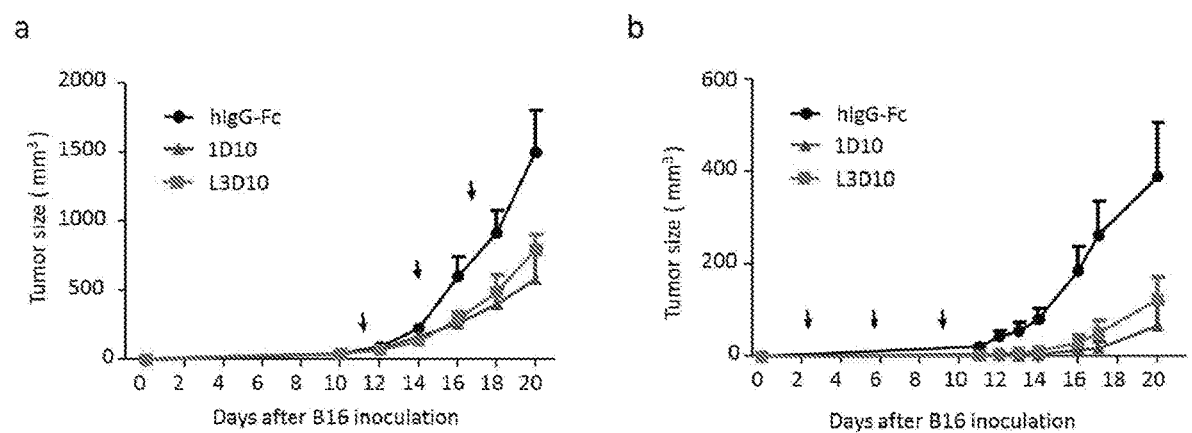

However, despite these apparent differences in blocking activity, both L3D10 and 10D1 display strong anti-tumor activity against the MC38 model in chimeric CTLA4$^{m/h}$ mice, as shown in FIG. 19. While the tumor grew progressively in the control Ig-treated mice, complete rejection was achieved by either anti-CTLA4 mAb. In multiple experiments, the two antibodies are comparable in causing tumor rejection. In another tumor model, B16 melanoma, both antibodies induced similar retardation of tumor growth, although complete rejection was not achieved by either antibody (FIG. 20).

Example 7. Anti-Tumor Effects are Associated with Intra-Tumoral Treg Depletion

Immune regulation in vivo results from a balance between immune cell activation and immune checkpoints. In particular, regulatory T cells (Tregs) are a subpopulation of T cells which regulate the immune system, maintain tolerance to self-antigens, and abrogate autoimmune disease. Recent studies have demonstrated that therapeutic efficacy of anti-mouse CTLA4 mAb is affected by the Fc subclass and host Fc receptor, which in turn affect antibody-dependent cytotoxicity of Treg selectively within tumor microenvironment (52, 53). As differential CTLA4 blocking activity in vivo does not appear to translate to differences in anti-tumor activity, we attempted to establish the mechanism of action(s) by which the anti-tumor occurs and looked at Tregs within the tumor microenvironment. To do this, we sacrificed MC38 tumor-bearing mice before the rejections were completed (FIG. 21) and analyzed the frequency of Treg in Ctla4$^{h/h}$ knockin mice that received control Ig, 10D1 or L3D10. While neither antibody reduces Treg in the spleen (FIG. 22C), both reduced Treg in the tumor microenvironment (FIG. 22E). Interestingly, 10D1 but not L3D10 expanded Treg in the spleen. Expansion of Treg in the spleen by 10D1 recapitulates a clinical finding that Ipilimumab increased FOXP3 expression by the peripheral blood leukocytes (54). Since the blocking and non-blocking antibodies are comparable in depletion of Treg in the tumor microenvironment, blockade of B7-CTLA4 interaction does not contribute to Treg depletion. Since 10D1 does not block B7-CTLA4 interaction in vivo and yet confer therapeutic effect in the Ctla4$^{h/h}$ mice and in melanoma patients, blockade of this interaction is not required for its therapeutic effect. Furthermore, since two mAbs with drastically different blocking effect have comparable therapeutic effect and selective Treg depletion in tumor microenvironment, blocking CTLA4-B7 interaction does not enhance therapeutic effect of an antibody.

To substantiate this observation, we tested the therapeutic effect of the two anti-CTLA4 mAbs in the Ctla4$^{m/h}$ mice in which the anti-human CTLA4 mAbs can bind to at maximal of 50% of CTLA4 molecules and in which neither antibody can block B7-CTLA4 interaction to achieve upregulation of B7 on dendritic cells (FIG. 16). Again, both antibodies cause rapid rejection of the MC38 tumors, although L3D10 is somewhat more effective than 10D1 (FIG. 22B). Correspondingly, both antibodies selectively depleted Treg in tumor microenvironment (FIGS. 22D and 21F). These genetic data further demonstrated the irrelevance of CTLA4 blockade in tumor rejection and local Treg depletion and thus refute the prevailing hypothesis that anti-CTLA4 mAb induce cancer immunity through blocking B7-CTLA4 interaction (10).

Example 8. Evaluation of Blocking Activities of Commonly Used Anti-Mouse CTLA4 mAbs 9H10 and 9D9

The concept that CTLA4 is a cell-intrinsic negative regulator for T cell regulation was proposed based on stimulatory effect of both intact and Fab of two anti-mouse CTLA4 mAbs (30, 31), 4F10 and 9H10, although no data were presented to demonstrate that these antibodies block B7-CTLA4 interaction. More recently, a third anti-mouse CTLA4 mAb, 9D9, was reported to have therapeutic effect in tumor bearing mice and cause local depletion of Treg in tumor microenvironment (52). We therefore set out to test all three commercially available anti-mouse CTLA4 mAbs that had been shown to induce tumor rejection for their ability to block B7-CTLA4 interaction under physiologically relevant configurations. As a first test, we used increasing amounts of anti-CTLA4 mAbs (up to 2,000 fold molar excess over CTLA4-Fc) to block binding of biotinylated CTLA4-Fc to plate-immobilized B7-1 and B7-2. As shown in FIG. 23A, anti-mouse CTLA4 mAb 9H10 did not block the B7-1-

Figure 24:
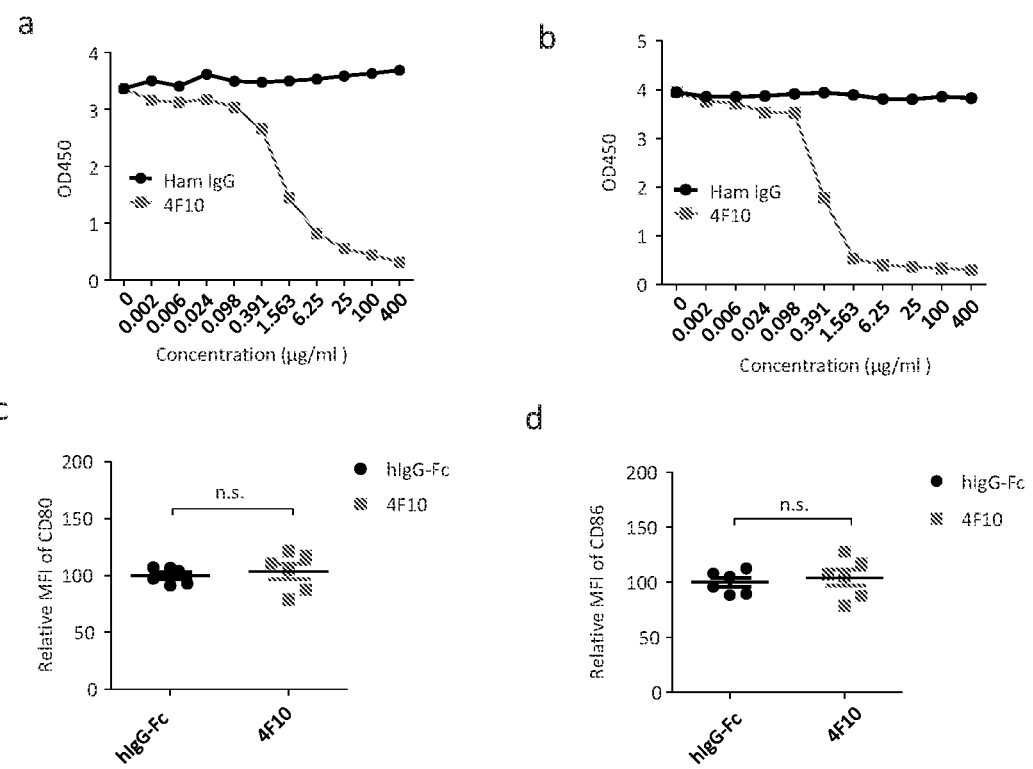

CTLA4 interaction even at the highest concentration tested, although a modest blocking was observed when 9D9 was used at very high concentrations. While mAb 9D9 effectively blocked the B7-2-CTLA4 interaction, 9H10 failed to do so (FIG. 23B). Interestingly, while 9D9 shows strong binding to soluble CTLA4-Fc, 9H10 showed poor binding (FIG. 23c), even though it is more potent than 9D9 in binding immobilized mouse CTLA4-Fc (FIG. 23D). Since lack of any blocking activity by 9H10 in this assay may simply reflect its poor binding to soluble CTLA4-Fc, we again used up-regulation of B7-1 and B7-2 on dendritic cells in WT mice (CTLA4$^{m/m}$) to measure in vivo blocking of B7-CTLA4 interaction. As shown in FIGS. 23E and F, 9H10 did not upregulate B7-1 expression on DC, while 9D9 increased B7-1 level by 15% (P<0.05). Interestingly, while 9D9 clearly upregulated B7-2 on DC, 9H10 failed to do so. Therefore, 9H10, the first and most extensively studied tumor immunotherapeutic anti-CTLA4 mAb does not block B7-CTLA4 interaction. Therefore, blocking B7-CTLA4 interaction does not contribute to induction of anti-tumor immunity by anti-mouse CTLA4 mAbs. Since both mAbs show comparable immunotherapeutic effect and comparable deletion of Treg in the tumor microenvironment (52), local deletion of Treg, rather than blockade of B7-CTLA4 interaction, provides a unifying explanation for therapeutic effect of anti-mouse CTLA4 mAbs. Interestingly, while 4F10 blocked B7-CTLA4 interaction in vitro, it failed to induce upregulation of B7 on DC in vivo (FIG. 24).

Taken together, we have demonstrated that clinically proven therapeutic anti-human CTLA4 mAb (10D1) and two anti-mouse CTLA4 mAbs (9H10 and 4F10) confers immunotherapeutic effect without blocking B7-CTLA4 interaction under physiologically relevant conditions. Furthermore, such blockade was not necessary for tumor rejection even for the mAb (L3D10) that can potently block B7-CTLA4 interaction. Since the therapeutic effect is substantially the same for antibodies with 1000-fold differences in blocking B7-CTLA4 interaction, such blockade does not contribute to cancer therapeutic effect of the anti-CTLA4 mAbs. These data refute the hypothesis that anti-CTLA4 mAb confers immunotherapeutic effect through checkpoint blockade (55). By refuting the prevailing hypothesis, our data suggest that the therapeutic effect of anti-CTLA4 mAb cannot be optimized by improving the blocking activities of the anti-CTLA4 mAbs. In this context, it is particular interest to note that Tremelimumab, which is superior in blocking B7-CTLA4 interaction (56), did not reach clinical endpoint in a phase III clinical trial (57). Meanwhile, by demonstrating strong correlation between tumor rejection of local Treg depletion and by refuting the involvement of blockade of B7-CTLA4 interaction in tumor immunity, our work favor the hypothesis that local deletion of Treg within the tumor environment is the main mechanism for therapeutic anti-CTLA4 mAb, and hence suggest new approaches to develop next generation of anti-CTLA4 mAb for cancer immunotherapy.

Finally, accumulating genetic data in the mice suggest that the original concept (30, 31) that CTLA4 negatively regulates T cell activation and that such regulation was achieved through SHP-2 (58, 59) may need to be revisited (60). Thus, while the severe autoimmune diseases in the Ctla4$^{-/-}$ mice have been used to support the notion of CTLA4 as a cell-intrinsic negative regulator for T cell activation (61, 62), at least three lines of genetic data have since emerged that are not consistent with this view. First, lineage-specific deletion of the Ctla4 gene in Treg but not in the effector T cells is sufficient to recapitulate the autoimmune phenotype observed in mice with germline deletion of the Ctla4 gene (50). These data suggest that the autoimmunity in the Ctla4$^{-/-}$ mice was not due to lack of cell-intrinsic negative regulator CTLA4 in effector T cells. Second, in chimera mice consisting of both WT and Ctla4$^{-/-}$ T cells, the autoimmune phenotype was prevented by co-existence of WT T cells (63). These data again strongly argue that autoimmune diseases were not caused by lack of cell-intrinsic negative regulator. The lack of cell-intrinsic negative regulator effect is also demonstrated by the fact that in the chimera mice, no preferential expansion of Ctla4$^{-/-}$ T cells was observed during viral infection (64). Third, T-cell specific deletion of Shp2, which was proposed to be mediating negative regulation of CTLA4 (58, 59), turned out to reduce rather than enhance T cell activation (65). In the context of these genetic data reported since the proposal of CTLA4 as negative regulator for T cell activation, our data reported herein call for a reappraisal of CTLA4 checkpoint blockade in cancer immunotherapy.

Example 9. Chimeric L3D10 Demonstrates Reduced Immune Adverse Events when Used in Combination with Other Immunotherapeutic Antibodies Recent clinical studies have revealed that combination therapy between anti-PD-1 and anti-CTLA4 mAb further increase the survival of end-stage melanoma patients. However, 55% of the patients that received the combination therapy developed grades 3 and 4 immune related adverse events (irAEs). It is therefore critical to develop antibodies with less toxicity. We have developed an in vivo model that recapitulates the irAEs associated with the combination therapy of anti-CTLA-4 and anti-PD-1 mAbs observed in the clinic. In this model we treated human CTLA4 gene knockin mice (CTLA4$^{h/h}$) during the perinatal period with high doses of anti-PD-1 and anti-CTLA-4 mAbs. We found that while the young mice tolerate treatment of individual mAbs, combination therapy with anti-PD-1 and 10D1 causes severe irAE with multiple organ inflammation, anemia and, as shown in FIG. 25, severely stunted growth. In contrast, when combined with anti-PD-1, chimeric L3D10 exhibits only mild irAE as demonstrated by normal weight gain.

To further examine to relative toxicity of chimeric L3D10 compared to 10D1 when administered in combination with anti-PD-1, we looked at the pathological effects in the CTLA4$^{h/h}$ knockin mice at 42 days after administration. As shown in FIG. 26, terminal body weight (day 42) in mice treated with L3D10+anti-PD-1 was similar to mice treated with hIgG negative control antibody. However, by comparison, the weight of mice treated with 10D1+anti-PD-1 was much lower. Accordingly, when we looked at the gross anatomy of these mice, the Uterus/Ovary/Bladder and thymus were noticeably smaller in mice treated with 10D1+PD-1 (FIG. 27). Again, the organs in mice treated with L3D10+anti-PD-1 was comparable to hIgG control. In contrast, the hearts dissected from mice treated with 10D1 appeared slightly larger in size with a noticeably whiter appearance. As a result we decided to look at erythropoiesis within the mice and observed clear differences in the mice treated with 10D1+anti-PD-1 relative to the groups treated with L3D10+anti-PD-1 or control antibody, which were fairly similar. As shown in FIG. 27A, the bone marrow from mice treated with 10D1+anti-PD-1 had a noticeably whiter color and the isolated blood was almost completely white in color (FIG. 28b). In accordance with this, when we took at closer look at the cells undergoing the different stages of blood development using CD71 and CD119 markers. Representative FACS profiles are shown in FIG. 28C, while summary data are presented in FIG. 28D. These data revealed a statistically significant reduction in the number of cells undergoing Stage IV development in the 10D1+anti-PD-1 treated mice (FIG. 28D).

To explore the potential mechanism of anemia in the 10D1-treated mice, we tested if 10D1+PD-1 treatment induces anti-red blood cell antibodies. As shown in FIG. 29, no anti-red blood cell antibodies are detected. Thus, development of red cell-specific autoantibodies are not responsible for anemia in the anti-PD-1+10D1-treated mice.

To further determine the toxicology of L3D10 vs 10D1 in combination with anti-PD-1, we performed histological analysis of the heart (FIG. 30), lung (FIG. 31), salivary gland (FIG. 32) and the kidney and liver (FIG. 33) following fixation in 10% formalin for at least 24 hours. In each of the tissues studied, mice treated with 10D1+anti-PD-1 displayed a high level of T cell infiltration. The toxicity score, based on severity of inflammation, are summarized in FIG. 34, which shows the high toxicity scores of mice treated with 10D1+anti-PD-1 relative to L3D10+anti-PD-1 which has scores only marginally higher than the hIgG control mouse group.

Example 10. L3D10 has Reduced Binding for Soluble CTLA4

L3D10 and 10D1 display similar binding patterns for plate immobilized CTLA4 (FIG. 36). As a possible explanation for the reduced toxicity of L3D10 relative to 10D1, particularly the increased T cell infiltration/activity associated with 10D1, we decided to look at the binding to soluble CTLA4. We chose to look at this because the association between CTLA4 polymorphism and multiple autoimmune diseases relates to the defective production of soluble CTLA4 (nature 2003, 423: 506-511) and genetic silencing of the sCTLA4 isoform increased the onset of type I diabetes in mice (Diabetes 2011, 60: 1955-1963). Furthermore, soluble CTLA4 (abatacept and belatacept) is a widely used drug for immune suppression. In accordance with this idea, when we looked at the relative binding to soluble CTLA4, we observed a marked decrease in the binding of L3D10 (FIG. 37).

We have demonstrate that anti-CTLA-4 mAb induce robust tumor injection in heterozygous Ctla4$^{h/m}$ mice in which only 50% of CTLA-4 molecules can bind to anti-human CTLA-4 mAbs. To determine if engagement of 50% of CTLA-4 is sufficient to induce irAE, we treated the Ctla4$^{h/m}$ mice with anti-PD-1+10D1. As shown in FIG. 35, anti-PD-1+10D1 failed to induce weight loss in the Ctla4$^{h/m}$ mice. Therefore, irAE and cancer immunity can be uncoupled genetically.

In vivo activity demonstrates that the L3D10 antibody retains its anti-tumor activity but displays reduced autoimmune adverse effect observed with other immunotherapeutic antibodies such as 10D1, indicating it is possible to enhance anti-tumor activity without exacerbating autoimmune adverse events. Accordingly, autoimmune side effects are not a necessary price for cancer immunity and that it is possible to uncouple these two activities. Characterization of L3D10 demonstrated that its ability to block the interaction of CTLA4 with B7.1 and B7.2 is more effective than by 10D1 and that this relates to a difference in the CTLA4 binding site between the antibodies. Furthermore, L3D10 was fused to a modified human IgG1 Fc domain that has mutations conferring strong ADCC activity that enhances the therapeutic effect of the antibody. Further characterization demonstrates that L3D10 and 10D1 bind to immobilized CTLA4 with a similar binding profile. However, L3D10 demonstrates much lower binding affinity to soluble CTLA4 than 10D1. Taken together, our data demonstrate that antibody L3D10 has great potential for clinical use in treating cancer patients with less severe adverse events.

Example 11. Humanization of L3D10

The humanization process begins by generating a homology modeled antibody 3D structure and creating a profile of the parental antibody based on structure modeling. Acceptor frameworks to utilize were identified based on the overall sequence identity across the framework, matching interface position, similarly classed CDR canonical positions, and presence of N-glycosylation sites that would have to be removed. One light chain (LC) and one heavy chain (HC) framework were selected for the humanization design.

Humanized antibodies were designed by creating multiple hybrid sequences that fuse select parts of the parental antibody sequence with the human framework sequences, including grafting of the CDR sequences into the acceptor frameworks. The predicted CDR sequences of the of parent antibody L3D10 are provided as SEQ ID NOS: 21-26 as indicated in Table 1A below:

TABLE 1A

The predicted CDR sequences of the parental antibody L3D10

| Antibody Chain | CDR | SEQ ID NO |
|---|---|---|
| Variable Light | 1 | 21 |
|  | 2 | 22 |
|  | 3 | 23 |
| Variable Heavy | 1 | 24 |
|  | 2 | 25 |
|  | 3 | 26 |

Using the 3D model, these humanized sequences were methodically analyzed by eye and computer modeling to isolate the sequences that would most likely retain antigen binding. The goal was to maximize the amount of human sequence in the final humanized antibodies while retaining the original antibody specificity.

Three humanized light chains (LC1, LC2 and LC3) and three humanized heavy chains (HC1, HC2 and HC3) were designed based on the selected acceptor frameworks. Each of the three HC or three LC sequences were from the same germline, with different back mutations to the murine parental sequence as shown in FIG. 38. The humanized variable region amino acid sequences and their optimized coding nucleotide sequence are listed in Seq ID NOS: 9-20. The CDR2 sequences of both the humanized heavy and light chains contain amino acid changes relative to the parental L3D10 antibody sequence and are listed in SEQ ID NOS 33-38 as indicated in Table 1B below.

TABLE 1B

CDR2 sequences of the humanized antibody variable regions.

| Antibody Sequence | CDR2 Sequence | SEQ ID NO |
|---|---|---|
| HC1 | YIWYDGNTNFHPSLKSR | 33 |
| HC2 | YIWYDGNTNFHSSLKSR | 34 |

TABLE 1B-continued

CDR2 sequences of the humanized antibody variable regions.

| Antibody Sequence | CDR2 Sequence | SEQ ID NO |
|---|---|---|
| HC3 | YIWYDGNTNFHSPLKSR | 35 |
| LC1 | AATNLQS | 36 |
| LC2 | AATNLQD | 37 |
| LC3 | AATSLQS | 38 |

The light and heavy humanized chains can now be combined to create variant fully humanized antibodies. All possible combinations of humanized light and heavy chains were tested for their expression level and antigen binding affinity to identify antibodies that perform similar to the parental antibody.

A new tool to calculate humanness scores for monoclonal antibodies (24) were used. This score represents how human-like an antibody variable region sequence looks, which is an important factor when humanizing antibodies. The humanness scores for the parental and humanized antibodies are shown in Tables 2 and 3 below. Based on our method, for heavy chains a score of 79 or above is indicative of looking human-like; for light chains a score of 86 or above is indicative of looking human-like.

TABLE 2

Humanized light chain information and humanness scores.

| Chain Name | Note | Full-length (Framework + CDR) Cutoff = 86 | Framework Only Cutoff = 90 |
|---|---|---|---|
| L2872 (Chimeric Parental) | Light chain | 71.3 | 78.2 |
| L3106 (LC1) | Regular humanized | 86.5 | 96.8 |
| L3107 (LC2) | Regular humanized | 83.6 | 94.0 |
| L3108 (LC3) | Regular humanized | 88.8 | 98.1 |

TABLE 3

Humanized heavy chain information and humanness scores.

| Chain Name | Note | Full-length (Framework + CDR) Cutoff = 79 | Framework Only Cutoff = 84 |
|---|---|---|---|
| H2872 (Chimeric Parental) | Parental | 62.0 | 70.3 |
| H3106 (HC1) | Regular humanized | 80.4 | 90.7 |
| H3107 (HC2) | Regular humanized | 78.9 | 89.4 |
| H3108 (HC3) | Regular humanized | 80.5 | 93.0 |

Full-length antibody genes were constructed by first synthesizing the variable region sequences. The sequences were optimized for expression in mammalian cells. These variable region sequences were then cloned into expression vectors that already contain human Fc domains; for the heavy chain, the hIgG1 (M252Y, S254T, T256E, S298A, E333A, K334A) backbone was utilized. In addition, for comparison the variable region of the chimeric parental heavy and light chains were constructed as full-length chimeric chains using the same backbone Fc sequences.

All 9 humanized antibodies underwent 0.01 liter small scale production. The chimeric parental antibody was also scaled-up for direct comparison. Plasmids for the indicated heavy and light chains were transfected into suspension HEK293 cells using chemically defined media in the absence of serum to make the antibodies. Whole antibodies in the conditioned media were purified using MabSelect SuRe Protein A medium (GE Healthcare). The 10 antibodies tested are shown in Table 4 below.

TABLE 4

Ten antibodies produced transiently in HEK293 cells

| Antibody name | Heavy Chain | Light Chain | PP # | Yield (mg/L) |
|---|---|---|---|---|
| Humanized HC1 + LC1 | H3106 | L3106 | 4630 | 54 |
| Humanized HC1 + LC2 | H3106 | L3107 | 4631 | 50 |
| Humanized HC1 + LC3 | H3106 | L3108 | 4632 | 45 |
| Humanized HC2 + LC1 | H3107 | L3106 | 4633 | 37 |
| Humanized HC2 + LC2 | H3107 | L3107 | 4634 | 44 |
| Humanized HC2 + LC3 | H3107 | L3108 | 4635 | 40 |
| Humanized HC3 + LC1 | H3108 | L3106 | 4636 | 46 |
| Humanized HC3 + LC2 | H3108 | L3107 | 4637 | 55 |
| Humanized HC3 + LC3 | H3108 | L3108 | 4638 | 53 |
| Chimeric Parental | H2872 | L2872 | 4629 | 28 |

The affinity of 9 humanized antibody combinations and the chimeric parental antibody to the antigen (huCTLA4) was evaluated by Octet. Multi-concentration kinetic experiments were performed on the Octet Red96 system (ForteBio). Anti-hIgG Fc biosensors (ForteBio, #18-5064) were hydrated in sample diluent (0.1% BSA in PBS and 0.02% Tween 20) and preconditioned in pH 1.7 Glycine. The antigen was diluted using a 7-point, 2-fold serial dilution starting at 600 nM with sample diluent. All antibodies were diluted to 10 μg/mL with sample diluent and then immobilized onto anti-hIgG Fc biosensors for 120 seconds. After baselines were established for 60 seconds in sample diluent, the biosensors were moved to wells containing the antigen at a series of concentrations to measure the association. Association was observed for 120 seconds and dissociation was observed for 180 seconds for each protein of interest in the sample diluent. The binding affinities were characterized by fitting the kinetic sensorgrams to a monovalent binding model (1:1 binding). The full kinetic measurements are summarized in Table 5 below.

TABLE 5

Kinetic measurements of the humanized antibodies and the parental antibody

| Loading Sample ID | Sample ID | KD (M) | kon(1/Ms) | kdis(1/s) | Full $X^2$ | Full $R^2$ |
|---|---|---|---|---|---|---|
| PP4629 | huCTLA4 | 2.3E−09 | 3.5E+05 | 8.0E−04 | 0.0033 | 0.9981 |
| PP4630 | huCTLA4 | 1.3E−08 | 1.3E+05 | 1.8E−03 | 0.0127 | 0.9848 |
| PP4631 | huCTLA4 | 6.9E−09 | 2.4E+05 | 1.6E−03 | 0.0120 | 0.9918 |
| PP4632 | huCTLA4 | 1.2E−08 | 1.6E+05 | 1.9E−03 | 0.0109 | 0.9915 |
| PP4633 | huCTLA4 | 7.1E−09 | 2.0E+05 | 1.4E−03 | 0.0106 | 0.9933 |
| PP4634 | huCTLA4 | 6.8E−09 | 2.8E+05 | 1.9E−03 | 0.0116 | 0.9866 |
| PP4635 | huCTLA4 | 8.4E−09 | 2.4E+05 | 2.0E−03 | 0.0077 | 0.9934 |
| PP4636 | huCTLA4 | 8.7E−09 | 2.5E+05 | 2.2E−03 | 0.0111 | 0.9905 |
| PP4637 | huCTLA4 | 6.4E−09 | 3.2E+05 | 2.1E−03 | 0.0173 | 0.9884 |
| PP4638 | huCTLA4 | 8.1E−09 | 2.9E+05 | 2.3E−03 | 0.0122 | 0.9920 |

Example 12. Anti-Tumor Activity of the Humanized Anti-CTLA4 Antibodies

Based on the relative binding affinity and humanness scores, we chose 3 antibodies for further evaluation:

PP4631—high affinity and good expression
PP4637—high affinity and good expression
PP4638—slightly lower affinity but highest humanization score Material for each of these antibodies was produced by transient production in HEK293 cells at the 0.1 liter scale followed by protein A purification. Binding affinity of the purified antibodies was confirmed by Octet analysis as shown in Table 6 below.

TABLE 6

Kinetic measurements of the humanized antibodies and the parental antibody

| Replicate | Loading Sample ID | Sample ID | KD (M) | kon(1/Ms) | kdis(1/s) | Full $X^2$ | Full $R^2$ |
|---|---|---|---|---|---|---|---|
| 1 | PP4631 | huCTLA4 | 7.2E−09 | 2.3E+05 | 1.6E−03 | 0.0274 | 0.9894 |
| 1 | PP4637 | huCTLA4 | 7.1E−09 | 2.7E+05 | 1.9E−03 | 0.0294 | 0.9899 |
| 1 | PP4638 | huCTLA4 | 9.4E−09 | 2.3E+05 | 2.1E−03 | 0.0211 | 0.9919 |
| 2 | PP4631 | huCTLA4 | 7.4E−09 | 2.3E+05 | 1.7E−03 | 0.0191 | 0.9919 |
| 2 | PP4637 | huCTLA4 | 8.4E−09 | 2.6E+05 | 2.2E−03 | 0.0248 | 0.9899 |
| 2 | PP4638 | huCTLA4 | 1.1E−08 | 2.1E+05 | 2.2E−03 | 0.0150 | 0.9934 |

We evaluated the anti-tumor activity of these three humanized antibodies compared to 10D1 and the chimeric L3D10 antibody using the syngeneic MC38 mouse tumor model in human CTLA4-knockin mice described in Example 5 above. FIG. 39A shows the treatment schedule of the in vivo experiment; mice were given a total of 4 doses of antibody every 3 days starting on day 7 after inoculation. As shown in FIG. 39B, all humanized antibodies completely eradicated the tumor and were comparable to 10D1.

In a another experiment we evaluated the anti-tumor activity of the humanized antibodies PP4631 and PP4637 compared to 10D1 and the chimeric L3D10 antibody using the syngeneic MC38 mouse tumor model in the heterozygous Ctla4$^{h/m}$ mice described in Example 5 (FIG. 14) at two different doses. As shown in FIG. 40, whereas all mAbs are indistinguishable when used at 30 mcg/mouse/injection (1.5 mg/kg), PP4637 was more effective at 10 mcg/mouse/injection (0.5 mg/kg), whereas PP4631 and 10D1 showed comparable activity.

The anti-tumor activity of the humanized antibodies compared to 10D1 and the chimeric L3D10 antibody was also demonstrated using the syngeneic B16-F1 melanoma mouse tumor model in human CTLA4-knockin mice as shown in FIG. 41. Mice were given a total of 3 doses of antibody every 3 days starting on day 2 after inoculation. As shown in FIG. 41, L3D10 and the humanized antibodies delayed tumor growth and were comparable to 10D1.

Example 13. Humanized Clones of L3D10 Maintain Superior Safety Profiles Over 10D1

To test if the superior safety profiles of L3D10 can be maintained after humanization, we compared PP4631 and PP4637 with 10D1 for their adverse effects when used in combination with anti-PD-1. As shown in FIG. 42, both PP4631 and PP4637 are less toxic than 10D1 when used in combination with anti-PD-1.

Figure 28:
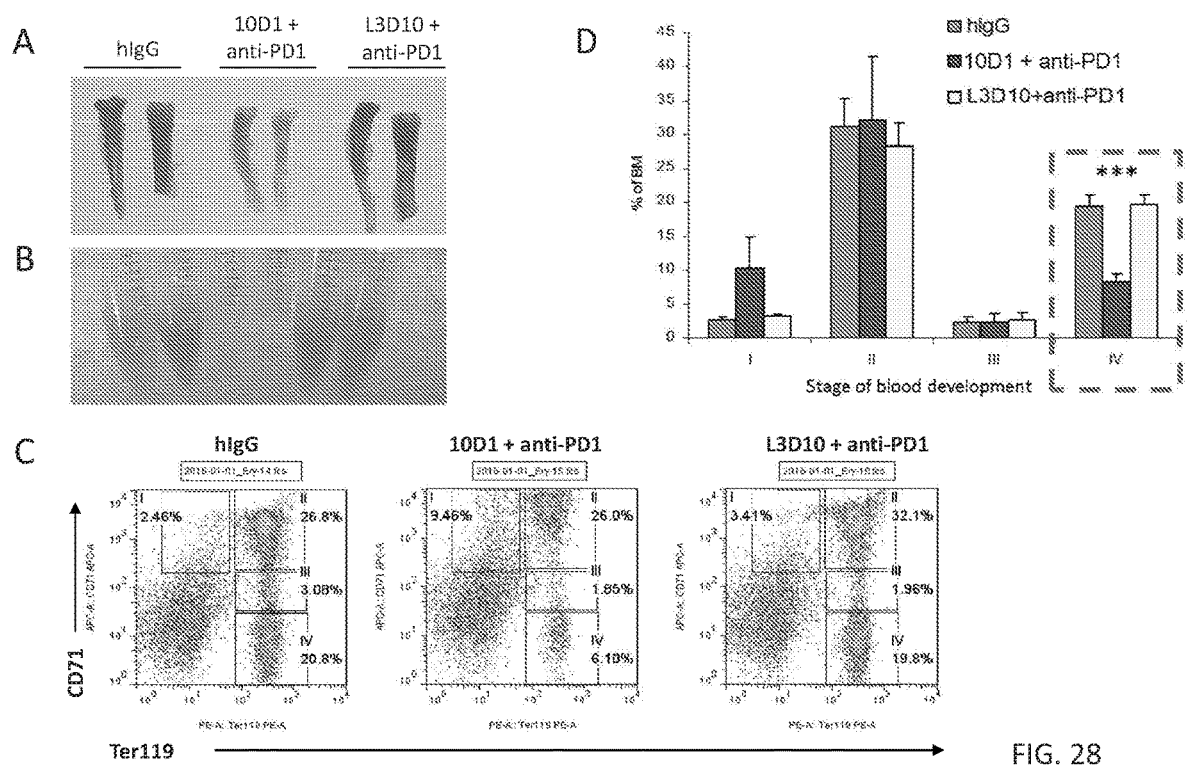

Consistent with the defective erythropoiesis described in FIG. 28, mice treated with 10D1 plus anti-PD-1 are anemic based on complete blood cell counts (CBC), while those that received anti-PD-1+PP4631 and anti-PD-1+PP4637 have largely normal CBC profiles as shown in FIG. 43. Moreover, analysis of the T cell profiles in the PBL reveal a robust systemic activation of both CD4 and CD8 T cells in mice that received 10D1+anti-PD-1, but not those that received anti-PD-1+PP4631 or anti-PD-1+PP4637 (FIG. 44), further supporting the notion that L3D10-based anti-CTLA-4 mAbs do not cause systemic T cell activation.

Example 14. Binding Characteristics of the Humanized Anti-CTLA4 Antibodies

In order to confirm that the humanized antibodies retained their CTLA4 binding characteristics, we looked at binding to immobilized and plate bound CTLA4. As shown in FIG. 45, humanization does not affect binding to immobilized CTLA4 and all 3 humanized antibodies demonstrated similar binding to the parental chimeric L3D10 antibody. However, humanization further reduces L3D10 binding to soluble CTLA4 as shown in FIG. 46. Based on reduced binding to soluble CTLA4, it is anticipated that the 3 humanized antibodies will induce equal tumor rejection with even less autoimmune side effects than L3D10.

Figure 47:
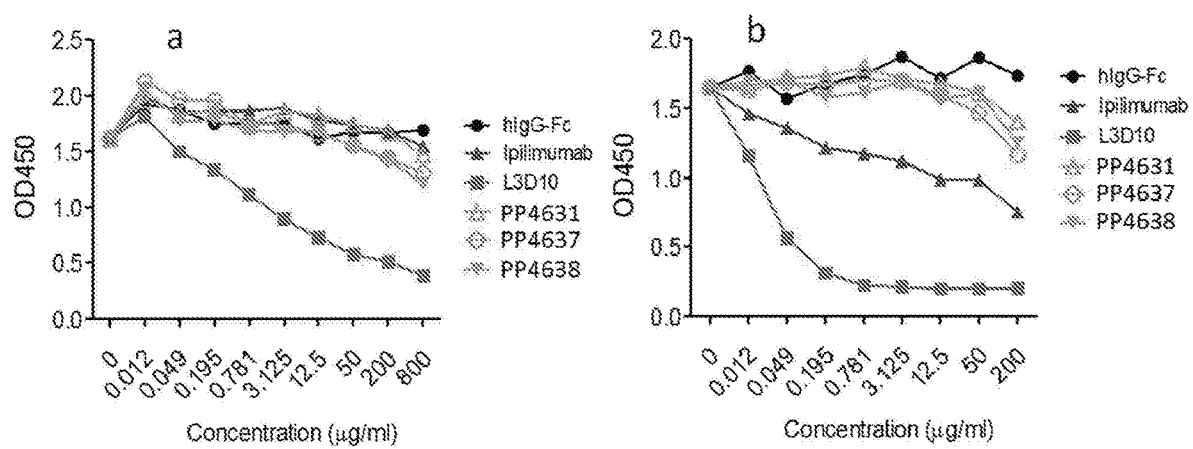

We have demonstrated that chimeric L3D10 has a 1000-fold higher blocking activity than 10D1. This raised an interesting possibility that blocking B7-CTLA-4 interactions may explain its lack of irAE. As shown in FIGS. 47 and 48, neither PP4631 nor PP4637 block B7-CTL-A4 interactions in vitro and in vivo. The fact that PP4631 and PP4637 show diminished irAE further supported the notion that blocking B7-CTLA-4 interaction is not responsible for improved safety of L3D10.

Given the proposed role for CTLA-4 in the protection against autoimmune diseases, we proposed reduced binding to soluble CTLA-4 as an underlying mechanism for improved safety profiles. To test this hypothesis, we used the growth weight gain among the female mice that received anti-PD-1+anti-CTLA-4 mAbs during the perinatal period as the basic indicator for irAE. As shown in FIG. 42, severe reduction in weight gain was observed in the mice that received both 10D1 and anti-PD-1, whereas those that received PP4637+anti-PD-1 had the lowest irAE, followed by PP4631 and then L3D10. The strict inverse correlation with reduced binding to sCTLA-4 are consistent with the central hypothesis.

Example 15. Processability Evaluation of the Humanized Anti-CTLA4 Antibodies

In order to evaluate the development and manufacturing potential of the three different humanized antibodies, a number of analytical methods were performed to characterize the different antibodies.

| Characteristic | Method |
|---|---|
| Production | Transient expression in HEK293 cells, followed by 1-step Protein A purification |
| Purity | Size exclusion chromatography (SEC) |
| Purity | Capillary Electrophoresis (reduced and non-reduced) |
| Non-Glyco | Capillary Electrophoresis (reduced) |
| Deamidation | Capillary isoelectric focusing (cIEF) and liquid chromatography-mass spectrometry (LC-MS) following DM stress treatment |
| Thermostability | Differential Scanning Calorimetry (DSC) |
| Oxidation | Peptide mapping |
| Binding specificity | CHO, 293 blank cell FACS |

As an initial assessment, the predicted molecular weights and isoelectric point of the three lead candidate antibodies was calculated based on amino acid sequences. As shown in Table 7, all antibodies were fairly similar, although antibody had a slightly lower PI.

TABLE 7

Theoretical parameters of the three humanized antibodies

| Protein Name | Theoretical MW (Da) | Theoretical PI |
|---|---|---|
| PP4631 | (49647.8 + 23483.1) × 2 = 96614.0 | 7.9 |
| PP4637 | (49644.9 + 23483.1) × 2 = 96611.1 | 7.65 |
| PP4638 | (49644.9 + 23311.9) × 2 = 96568.7 | 7.9 |

Product Yield Assessment

In order to assess the productivity of the different antibodies, HEK293 cells were transiently transfected with vectors expressing the heavy and light chains of the different antibodies. These cells were then cultured in shake flasks for 6 days using serum-free medium. After 6 days, the supernatant was collected and the antibodies were purified by one-step Protein A chromatography. As should in Table 8 below, antibodies PP4631 and PP4637 demonstrated similar protein yields whereas antibody PP4638 was produced at a much lower relative yield.

TABLE 8

Humanized antibody production yield assessment.

| Antibody | Concentration (mg/mL) | OD 260/280 | Yield (mg/L) |
|---|---|---|---|
| PP4631 | 1.280 | 0.53 | 126 |
| PP4637 | 4.532 | 0.53 | 118 |
| PP4638 | 0.729 | 0.57 | 56 |

In order to assess the purity of the transiently expressed antibodies, samples were analyzed by reducing and non-reducing SDS-PAGE. As shown in FIG. 50, samples from all 3 antibodies produced gel bands indicative of an antibody molecule and that the samples were relatively pure following Protein A purification.

Size Exclusion Chromatography

To further examine the purity and aggregation of the different antibodies following transient expression, we performed size exclusion chromatography of the purified proteins. Briefly, 50 μg of filtered (using 0.22 μm filter) sample was used for SE-HPLC separation using a TOSOH G3000 SWxl 5 μm column. PBS pH 7.4 was used as the mobile phase. As shown in Table 9 below, all the humanized antibodies show >90% purity after protein A purification. Antibodies PP4631 and PP4637 demonstrated similarly low levels of higher molecular weight (MW) aggregates and degradation present with the antibody samples with most of the protein within the main peak. In contrast, antibody PP4638 had higher levels of aggregation and some degradation. The SE-HPLC chromatograms are shown in FIG. 51.

TABLE 9

Size Exclusion Chromatography

| Antibody | Aggregation | Main Peak | Degradation |
|---|---|---|---|
| PP4631 | 2.6% | 97.4% | 0 |
| PP4637 | 3.0% | 97.0% | 0 |
| PP4638 | 6.5% | 92.4% | 1.1% |

Capillary Electrophoresis (CE)

Capillary electrophoresis was used to quantitate the amount of protein within the peak bands under both reduced and non-reduced conditions, as well as the amount of unglycosylated heavy chain protein. Briefly, 100 μg of sample was diluted into CE-SDS sample buffer along with Iodoacetamide (non-reduced conditions) or K-mercaptoethanol (reduced conditions), along with 2 μL of a 10 kDa standard protein. Samples were then treated for 10 min at 70° C. For separation, PA-800, 50 μm I.D. bare-fused silica capillary was used; running length 20.2 cm; separating voltage 15 kV; $OD_{220}$ for detection. As shown in Table 10 below, all three proteins demonstrated high levels of purity, consistent with SDS-PAGE, and all were highly glycosylated. The CE-SDS chromatograms are shown in FIG. 52.

TABLE 10

Capillary Electrophoresis

| Antibody | Non-reduced % | Reduced % | Unglycosylated Heavy Chain |
|---|---|---|---|
| PP4631 | 97.3 | 99.5 | 0.3 |
| PP4637 | 97.2 | 99.5 | 0.4 |
| PP4638 | 96.9 | 99.4 | 0.4 |

Deamidation: Capillary Isoelectric Focusing (cIEF) and Liquid Chromatography-Mass Spectrometry (LC-MS)

The level of protein deamidation under high pH stress was determined by comparing the antibodies with and without high pH stress treatment over two different time periods (5 hrs and 12.5 hrs), followed by cIEF and LC-MS analysis.

The charge isoform profile and isoelectric points of the different antibodies was determined by capillary isoelectric focusing (cIEF). Briefly, samples underwent buffer exchange into 20 mM Tris pH 8.0 and then 100 μg of sample protein was mixed with the amphoteric electrolyte, methyl cellulose, along with PI 7.05 and PI 9.77 markers. iCE3™ was used for analysis, with a 100 μm I.D. capillary; 1.5 kV plus 3 kV; $OD_{280}$ for detection. For deamidation stress treatment, samples were treated with 500 mM $NaHCO_3$ for 5 hr or 12.5 hr, then examined with cIEF and LC-MS. The results of the analysis are shown in Table 11 below and the LC-MS graphs are shown in FIG. 53. All three antibodies show a predicted increase in the amount of deamidated species with stress conditions and a corresponding drop in the main peak. As predicted from the amino acid sequence, the pI of antibody PP4637 is a little lower than for PP4631 and PP4638 (Table 7) and the higher observed pI compared to the predicted pI presumably indicates glycosylation.

TABLE 11

Isoelectric focusing and deamidation

| Antibody | Peak PI | DM treatment time | DM % | Main peak % | Basic % |
|---|---|---|---|---|---|
| PP4631 | 8.28 | Untreated | 17.3 | 71.9 | 3.0 |
|  |  | 5 h | 27.1 | 65.4 | 3.0 |
|  |  | 12.5 h | 40.3 | 53.2 | 2.5 |
| PP4637 | 8.11 | Untreated | 18.1 | 79.0 | 2.9 |
|  |  | 5 h | 31.5 | 65.7 | 2.8 |
|  |  | 12.5 h | 44.0 | 53.8 | 2.2 |
| PP4638 | 8.36 | Untreated | 22.5 | 69.6 | 2.3 |
|  |  | 5 h | 34.4 | 57.6 | 2.7 |
|  |  | 12.5 h | 45.9 | 46.5 | 2.3 |

Differential Scanning Calorimetry (DSC) Thermal Analysis

Figure 54:
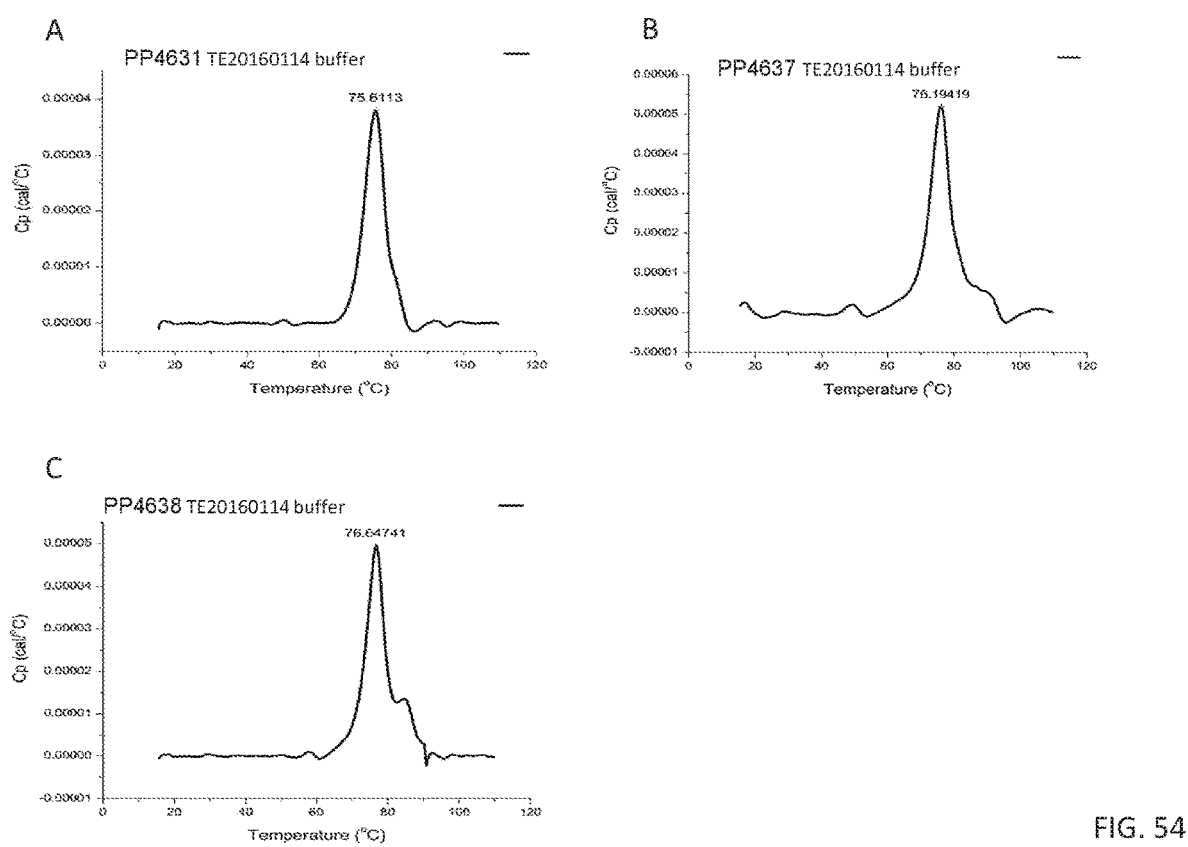

In order to determine the thermal stability and melting temperatures of the different antibodies, they were subject to Differential Scanning Calorimetry (DSC) Thermal Analysis. Briefly, 2 mg/mL samples in PBS pH 7.4 were subject to temperature ramping from 15° C. to 105° C. at a rate of 1° C./min. Cp changing with temperature was monitored for both samples and buffer (as background). Cp vs temperature curves were obtained with background subtraction, and peaks indicated the Tm of the analytes. As shown in Table 12 below, all three antibodies demonstrated a similarly high melting temperature. DSC curves for the three antibodies are shown in FIG. 54.

TABLE 12

Size Exclusion Chromatography

| Antibody | $T_M$ (° C.) |
|---|---|
| PP4631 | 75.6 |
| PP4637 | 76.2 |
| PP4638 | 76.6 |

Oxidation: Peptide Mapping

Oxidative modification of the humanized antibodies was evaluated by peptide mapping using LC-MS with or without oxidative stress. The samples were denatured at 65° C. in the presence of 6 M GnCl and 5 mM K-ME, then acetylated with iodacetamide. The processed samples are then digested with Trypsin (Promega, sequencing grade) at 55° C. and the digested mixture was separated on a C18 reversed phase LC column (ACQUITY UPLC BEH130 C18, 2.1×100 mm, 1.7 —m) and analyzed by mass spectrometry (Waters XEVO-G2S QTOF) using Masslynx and Biophatmlynx analysis tools. For the oxidation stress analysis, samples treated with 0.05% or 0.1% $H_2O_2$ for 1 hr, then examined with LC-MS. The results are shown in Tables 13-16 below.

TABLE 13

Oxidation of the humanized antibodies at Methionine sites. Top panel: antibody PP4631. Middle panel: antibody PP4637. Bottom panel: antibody PP4638.

| | | | | | | PP4631 oxidation (%) | | |
| | | | | | | Oxidation | 0.05% $H_2O_2$ Oxidation | 0.1% $H_2O_2$ Oxidation |
| Modifiers | Fragment Number | start | end | Modification sites | Sequence | 0 h | 1 h | 1 h |
|---|---|---|---|---|---|---|---|---|
| Oxidation M(1) | 1: T001 | 1 | 18 | 4 | DIQMTQSPSSLSASVGDR (SEQ ID NO: 74) | 0.4 | 0.5 | 0.4 |
| | 2: T037 | 425 | 447 | 436 | WQQGNVFSCSVMHEALHNHYTQK (SEQ ID NO: 75) | 0.6 | 1.6 | 2.7 |

| | | | | | | PP4637 oxidation (%) | | |
| | | | | | | Oxidation | 0.05% $H_2O_2$ Oxidation | 0.1% $H_2O_2$ Oxidation |
| Modifiers | Fragment Number | start | end | Modification sites | Sequence | 0 h | 1 h | 1 h |
|---|---|---|---|---|---|---|---|---|
| Oxidation M(1) | 1: T001 | 1 | 18 | 4 | DIQMTQSPSSLSASVGDR (SEQ ID NO: 74) | 0.4 | 0.5 | 0.5 |
| | 2: T036 | 425 | 447 | 436 | WQQGNVFSCSVMHEALHNHYTQK (SEQ ID NO: 75) | 0.7 | 1.7 | 3.0 |

| | | | | | | PP4638 oxidation (%) | | |
| | | | | | | Oxidation | 0.05% $H_2O_2$ Oxidation | 0.1% $H_2O_2$ Oxidation |
| Modifiers | Fragment Number | start | end | Modification sites | Sequence | 0 h | 1 h | 1 h |
|---|---|---|---|---|---|---|---|---|
| Oxidation M(1) | 1: T001 | 1 | 18 | 4 | DIQMTQSPSSLSASVGDR (SEQ ID NO: 74) | 0.7 | 0.7 | 0.6 |
| | 2: T036 | 425 | 447 | 436 | WQQGNVFSCSVMHEALHNHYTQK (SEQ ID NO: 75) | 0.9 | 1.6 | 2.8 |

TABLE 14

Oxidation of the humanized antibody PP4631 at Tryptophan sites. Red numbers indicate evidence of fragmentation found; "—" indicates none detected; "0" indicates detected at extremely low levels.

| | | | | | | PP4631 oxidation (%) | | |
| | | | | | | Oxidation | 0.05% $H_2O_2$ oxidation | 0.1% $H_2O_2$ oxidation |
| Modifiers | Fragment Number | start | end | position | Sequence | 0 h | 1 h | 1 h |
|---|---|---|---|---|---|---|---|---|
| Oxidation W(1) | 1: T003 | 25 | 39 | 35 | ASENIYSNLAWYQQK (SEQ ID NO: 76) | 0.2 | 0.2 | 0.2 |
| | 1: T007 | 62 | 103 | 92 | FSGSGSGTDYTLTISSLQPEDFATYFCQHL WGTPYTFGQGTK (SEQ ID NO: 77) | — | 0 | 0 |
| | 1: T013 | 146 | 149 | 148 | VQWK (SEQ ID NO: 78) | 0.2 | 0.2 | 0.1 |
| | 2: T001 | 1 | 38 | 36 | QVQLQESGPGLVKPSETLSLTCTVSGFSLT SYGLSWIR (SEQ ID NO: 79) | 0 | — | — |

TABLE 14-continued

Oxidation of the humanized antibody PP4631 at Tryptophan sites.
Red numbers indicate evidence of fragmentation found;
"—" indicates none detected; "0" indicates detected at extremely low levels.

| Modifiers | Fragment Number | start | end | position | Sequence | PP4631 oxidation (%) Oxidation 0 h | 0.05% H₂O₂ oxidation 1 h | 0.1% H₂O₂ oxidation 1 h |
|---|---|---|---|---|---|---|---|---|
| | 2: T003 | 44 | 64 | 47/52 | GLEWIGYIWYDGNTNFHPSLK (SEQ ID NO: 80) | 0 | 0.2 | 0.2 |
| | 2: T009 | 98 | 129 | 115 | TEGHYYGSNYGYYALDYWGQGTSVTVSSAS TK (SEQ ID NO: 81) | 0 | 0.1 | 0 |
| | 2: T012 | 156 | 218 | 166 | DYFPEPVTVSWNSGALTSGVHTFPAVLQSS GLYSLSSVVTVPSSSLGTQTYICNVNHKPS NTK (SEQ ID NO: 82) | 0.1 | 0.1 | 0.1 |
| | 2: T020 | 283 | 296 | 285 | FNWYVDGVEVHNAK (SEQ ID NO: 83) | 4.5 | 3.9 | 3.9 |
| | 2: T023 | 310 | 325 | 321 | VVSVLTVLHQDWLNGK (SEQ ID NO: 84) | 0 | 0 | 0 |
| | 2: T033 | 379 | 400 | 389 | GFYPSDIAVEWESNGQPENNYK (SEQ ID NO: 85) | 2.2 | 2.6 | 2.7 |
| | 2: T037 | 425 | 447 | 425 | WQQGNVFSCSVMHEALHNHYTQK (SEQ ID NO: 75) | 0.1 | 0.1 | 0.1 |

TABLE 15

Oxidation of the humanized antibody PP4637 at Tryptophan sites.
Red numbers indicate evidence of fragmentation found;
"—" indicates none detected; "0" indicates detected at extremely low levels.

| Modifiers | Fragment Number | start | end | position | Sequence | PP4637 oxidation (%) Oxidation 0 h | 0.05% H₂O₂ oxidation 1 h | 0.1% H₂O₂ oxidation 1 h |
|---|---|---|---|---|---|---|---|---|
| Oxidation W(1) | 1: T003 | 25 | 39 | 35 | ASENIYSNLAWYQQK (SEQ ID NO: 76) | 0.2 | 0.2 | 0.2 |
| | 1: T007 | 62 | 103 | 92 | FSGSGSGTDYTLTISSLQPEDFATYFCQH LWGTPYTFGQGTK (SEQ ID NO: 77) | — | — | 0 |
| | 1: T013 | 146 | 149 | 148 | VQWK (SEQ ID NO: 78) | 0.1 | 0.1 | 0.1 |
| | 2: T001 | 1 | 38 | 36 | QVQLQESGPGLVKPSETLSLTCTVSGFSL TSYGLSWIR (SEQ ID NO: 79) | — | 0.1 | — |
| | 2: T003 | 44 | 64 | 47/52 | GLEWIGYIWYDGNTNFHSPLK (SEQ ID NO: 86) | 0 | 0 | 0.1 |
| | 2: T008 | 98 | 129 | 115 | TEGHYYGSNYGYYALDYWGQGTLVTVSSA STK (SEQ ID NO: 87) | 0.2 | 0.2 | 0.1 |
| | 2: T011 | 156 | 218 | 166 | DYFPEPVTVSWNSGALTSGVHTFPAVLQS SGLYSLSSVVTVPSSSLGTQTYICNVNHK PSNTK (SEQ ID NO: 82) | — | 0 | 0 |
| | 2: T019 | 283 | 296 | 285 | FNWYVDGVEVHNAK (SEQ ID NO: 83) | 4.0 | 4.0 | 4.0 |
| | 2: T022 | 310 | 325 | 321 | VVSVLTVLHQDWLNGK (SEQ ID NO: 84) | 0 | 0 | 0 |
| | 2: T032 | 379 | 400 | 389 | GFYPSDIAVEWESNGQPENNYK (SEQ ID NO: 85) | 2.5 | 2.5 | 2.7 |
| | 2: T036 | 425 | 447 | 425 | WQQGNVFSCSVMHEALHNHYTQK (SEQ ID NO: 75) | 0.2 | 0 | 0.1 |

TABLE 16

Oxidation of the humanized antibody PP4638 at Tryptophan sites.
Red numbers indicate evidence of fragmentation found;
"—" indicates none detected; "0" indicates detected at extremely low levels.

| Modifiers | Fragment Number | start | end | position | Sequence | PP4638 oxidation (%) Oxidation 0 h | 0.05% H₂O₂ oxidation 1 h | 0.1% H₂O₂ oxidation 1 h |
|---|---|---|---|---|---|---|---|---|
| Oxidation W(1) | 1: T003 | 25 | 42 | 35 | ASENIYSNLAWYQQKPGK (SEQ ID NO: 88) | — | — | — |
| | 1: T006 | 62 | 103 | 92 | FSGSGSGTDFTLTISSLQPEDFATYYCQH LWGTPYTFGGGTK (SEQ ID NO: 89) | 0 | 0 | 0 |
| | 1: T012 | 146 | 149 | 148 | VQWK (SEQ ID NO: 78) | 0.1 | — | — |
| | 2: T001 | 1 | 38 | 36 | QVQLQESGPGLVKPSETLSLTCTVSGFSL TSYGLSWIR (SEQ ID NO: 79) | 0 | — | — |

TABLE 16-continued

Oxidation of the humanized antibody PP4638 at Tryptophan sites.
Red numbers indicate evidence of fragmentation found;
"—" indicates none detected; "0" indicates detected at extremely low levels.

| Modifiers | Fragment Number | start | end | position | Sequence | PP4638 oxidation (%) | | |
|---|---|---|---|---|---|---|---|---|
| | | | | | | Oxidation 0 h | 0.05% H₂O₂ oxidation 1 h | 0.1% H₂O₂ oxidation 1 h |
| 2: | T003 | 44 | 64 | 47/52 | GLEWIGYIWYDGNTNFHSPLK (SEQ ID NO: 86) | 0.1 | 0.2 | 0.2 |
| 2: | T008 | 98 | 129 | 115 | TEGHYYGSNYGYYALDYWGQGTLVTVSSASTK (SEQ ID NO: 87) | 0.3 | 0.3 | 0.4 |
| 2: | T011 | 156 | 218 | 166 | DYFPEPVTVSWNSGALTSGVHTFPAVLQSSGLYSLSSVVTVPSSSLGTQTYICNVNHKPSNTK (SEQ ID NO: 82) | 0 | 0 | 0.2 |
| 2: | T019 | 283 | 296 | 285 | FNWYVDGVEVHNAK (SEQ ID NO: 83) | 3.7 | 4.1 | 4.1 |
| 2: | T022 | 310 | 325 | 321 | VVSVLTVLHQDWLNGK (SEQ ID NO: 84) | 0 | 0 | 0 |
| 2: | T032 | 379 | 400 | 389 | GFYPSDIAVEWESNGQPENNYK (SEQ ID NO: 85) | 2.6 | 2.9 | 2.7 |
| 2: | T036 | 425 | 447 | 425 | WQQGNVFSCSVMHEALHNHYTQK (SEQ ID NO: 75) | 0 | 0 | 0 |

Binding Specificity

The binding specificity of the different antibodies was determined by assessing the ability to detect non-specific binding to two different cell lines that do not express CTLA4 (CHO and HEK293) relative to 10D1 at two different concentrations. Briefly, 100 µg/mL or 20 µg/mL samples (or reference mAb) in PBS was incubated with $3 \times 10e^6$ cells/ml (CHO or HEK293). FITC labeled rabbit-anti-human-IgG antibody (Boster, Wuhuan, China) was used for detection and the binding of target mAb to cells was measured by FACS. As shown in Table 17 below, antibodies PP4631 and PP4637 demonstrate very low binding and good specificity, whereas antibody PP4638 displayed non-specific binding activity to the control cell lines.

TABLE 17

Binding Specificity to CHO and HEK293 cell lines

| | MFI | |
|---|---|---|
| Samples | CHO | HEK 293 |
| CELL only | 3.50583 | 4.16546 |
| 2ⁿᵈ Ab only | 4.00062 | 4.68083 |
| 10D1 (100 ug/ml) | 3.82459 | 5.49435 |
| 10D1 (20 ug/ml) | 3.70334 | 4.95407 |
| PP4631 (100 ug/ml) | 10.8065 | 7.76113 |
| PP4631 (20 ug/ml) | 5.03402 | 5.5862 |
| PP4637 (100 ug/ml) | 15.0944 | 10.5987 |
| PP4637 (20 ug/ml) | 5.89652 | 5.78233 |
| PP4638 (100 ug/ml) | 83.4742 | 36.8002 |
| PP4638 (20 ug/ml) | 15.3381 | 9.86523 |

Example 16. Epitope Mapping of the L3D10 and Humanized Antibodies

In order to map the CTLA-4 binding epitope of the L3D10 parent antibody and the humanized variants, PP4631 and PP4637, we took advantage of the fact that the mouse and human CTLA4 proteins are cross-reactive to B7-1, but not to the anti-CTLA-4 antibodies. Accordingly, we designed a number of mutants of the human CTLA-4Fc protein in which clusters of amino acids from the human CTLA-4 protein were replaced with amino acids from the murine Ctla-4 protein. As the anti-CTLA-4 antibodies used in this study do not bind to murine Ctla-4, binding of the anti-human CTLA-4 antibodies should be abolished when key residues of the antibody binding epitope are replaced with murine amino acids.

DNA vectors encoding 11 CTLA-4Fc mutant proteins (M1-M11)(SEQ ID NOS: 40-50) were constructed based on the wild type human CTLA-4Fc sequence and proteins were produced by transient transfection in HEK293 at the 0.01 mL scale followed by one-step Protein A chromatography purification.

Binding of the anti-CTLA4 antibodies to CTLA4Fc proteins was performed by ELISA. Plates were coated with CTLA-4Fc proteins at 1 µg/mL and biotinylated antibodies or B7-1 Fc fusion protein were then used in soluble phase in the binding assay, with the amounts of protein bound measured using horse-radish peroxidase (HRP)-conjugated streptavidin.

The anti-human CTLA-4 antibodies do not cross react with murine Ctla-4, which presumably reflects differences in the amino acid sequence between human and mouse CTLA-4 in the extracellular domain. FIG. 55 shows the alignment of the human, macaque and mouse CTLA-4 extracellular domains and highlight the sequence conservation between human and macaque, while showing the numerous differences between the murine and primate sequences. Due to conservation of the MYPPPY binding motif, mouse and human CTLA4 proteins are cross-reactive to B7-1 (72).

In order to map the binding epitope of the anti-human CTLA-4 antibodies we generated a number of non-overlapping CTLA-4Fc mutant proteins that incorporate clusters of murine-specific amino acids into the human CTLA-4 sequence. The amino acids incorporated into each of the 11 mutants is shown in FIG. 55, and the amino acids sequences of the WT and mutant CTLA-4Fc proteins is shown in FIG. 56. These proteins were produced by transient transfection in HEK293 cells and the yield is provided in Table 18. Many of the mutations appear to affect protein expression as indicated by their yields relative to the WT human CTLA-4Fc protein.

TABLE 18

WT and mutant CTLA-4Fc proteins produced transiently in HEK293 cells.

| Protein name | Yield (mg) |
|---|---|
| CTLA-4Fc WT control | 0.72 |
| Mutant 1 | 1.29 |
| Mutant 2 | 0.03 |
| Mutant 3 | 0.21 |
| Mutant 4 | 0.11 |
| Mutant 5 | 1.89 |
| Mutant 6 | 0.38 |
| Mutant 7 | 0.25 |
| Mutant 8 | 1.61 |
| Mutant 9 | 0.01 |
| Mutant 10 | 0.04 |
| Mutant 11 | 1.70 |

The capacity of chimeric L3D10 and the humanized antibodies PP4631 and PP4637 to bind the immobilized CTLA-4Fc mutant constructs was then determined by ELISA in which plates were coated with the CTLA-4 mutant constructs and biotinylated anti-CTLA-4 antibodies, or B7-1Ig control protein, were added and binding measured using HRP-conjugated streptavidin. The results of binding assays are shown in Tables 19-22. As expected, all 4 binding proteins demonstrated nice dose-dependent binding for the WT CTLA-4Fc protein. However, mutations that were introduced into the M9 and M10 proteins appear to alter the overall structure and these mutants failed to bind B7-1 Fc. Mutations introduced in M2 and M4 also partially altered CTLA-4 conformation as indicated by reduced binding relative to the WT protein. Consistent with this notion, all 4 of these mutants (M2, M4, M9 and M10) were expressed at much lower yield (Table 18). In contrast, using binding to the WT CTLA-4Fc protein and binding of the B7-1Fc proteins as references, M11 clearly stands out as a protein that is expressed well, binds B7-1Fc efficiently but failed to bind two humanized anti-CTLA-4 antibodies. Its binding to original L3D10 is also reduced by approximately 100-fold (Table 20). As expected, the mutations that affect the overall confirmation also affected the binding to the anti-CTLA-4 antibodies.

TABLE 19

Integrity of CTLA4Ig mutants as indicated by their binding to B7-1 Ig fusion protein. Binding to CTLA4Fc proteins was performed by ELISA, with the amounts of biotinylated protein bound measured by horse-radish peroxidase (HRP)-conjugated streptavidin. Values shown are the OD450 measurements. WT = wild type CTLA-4Fc. M1-M11 are CTLA-4Fc mutant proteins.

| Protein Conc. | WT | M1 | M2 | M3 | M4 | M5 | M6 | M7 | M8 | M9 | M10 | M11 |
|---|---|---|---|---|---|---|---|---|---|---|---|---|
| 0 | 0.193 | 0.196 | 0.202 | 0.184 | 0.182 | 0.182 | 0.184 | 0.185 | 0.18 | 0.172 | 0.175 | 0.174 |
| 0 | 0.19 | 0.182 | 0.177 | 0.175 | 0.171 | 0.171 | 0.173 | 0.17 | 0.168 | 0.164 | 0.162 | 0.163 |
| 10 ng/ml | 0.259 | 0.328 | 0.204 | 0.267 | 0.199 | 0.286 | 0.255 | 0.218 | 0.293 | 0.166 | 0.167 | 0.22 |
| 10 ng/ml | 0.257 | 0.311 | 0.187 | 0.249 | 0.184 | 0.271 | 0.244 | 0.22 | 0.276 | 0.154 | 0.159 | 0.217 |
| 100 ng/ml | 1.137 | 1.594 | 0.316 | 1.087 | 0.359 | 1.513 | 1.093 | 0.785 | 1.468 | 0.164 | 0.164 | 0.884 |
| 100 ng/ml | 1.111 | 1.553 | 0.299 | 1.082 | 0.34 | 1.221 | 1.049 | 0.695 | 1.375 | 0.155 | 0.15 | 1.045 |
| 1 ug/ml | 2.813 | 3.147 | 1.179 | 3.147 | 1.375 | 2.877 | 3.053 | 2.703 | 3.253 | 0.199 | 0.171 | 3.053 |
| 1 ug/ml | 2.651 | 3.053 | 0.986 | 2.864 | 1.413 | 3.025 | 2.983 | 2.716 | 2.93 | 0.218 | 0.172 | 3.159 |

TABLE 20

Epitope mapping of chimeric L3D10 antibody. Binding to CTLA4Fc proteins was performed by ELISA, with the amounts of biotinylated protein bound measured by horse-radish peroxidase (HRP)-conjugated streptavidin. Values shown are the OD450 measurements. WT = wild type CTLA-4Fc. M1-M11 are CTLA-4Fc mutant proteins

| Protein Conc. | WT | M1 | M2 | M3 | M4 | M5 | M6 | M7 | M8 | M9 | M10 | M11 |
|---|---|---|---|---|---|---|---|---|---|---|---|---|
| 0 | 0.202 | 0.196 | 0.2 | 0.187 | 0.184 | 0.189 | 0.192 | 0.198 | 0.187 | 0.179 | 0.179 | 0.183 |
| 0 | 0.195 | 0.187 | 0.185 | 0.18 | 0.176 | 0.176 | 0.176 | 0.176 | 0.17 | 0.166 | 0.166 | 0.167 |
| 10 ng/ml | 1.433 | 2.47 | 0.375 | 0.62 | 0.507 | 1.539 | 1.033 | 0.714 | 1.233 | 0.18 | 0.18 | 0.202 |
| 10 ng/ml | 1.518 | 2.432 | 0.317 | 0.587 | 0.356 | 1.366 | 0.976 | 0.738 | 1.237 | 0.171 | 0.169 | 0.203 |
| 100 ng/ml | 3.053 | 3.253 | 1.384 | 2.318 | 2.142 | 2.841 | 2.699 | 2.495 | 2.909 | 0.295 | 0.215 | 0.635 |
| 100 ng/ml | 3.025 | 3.239 | 1.164 | 2.354 | 1.409 | 2.991 | 2.771 | 2.483 | 2.841 | 0.304 | 0.216 | 0.759 |
| 1 ug/ml | 3.373 | 3.268 | 2.387 | 3.184 | 2.651 | 3.025 | 3.092 | 3.147 | 3.136 | 0.916 | 0.804 | 2.841 |
| 1 ug/ml | 3.114 | 2.967 | 2.619 | 3.124 | 2.659 | 3.034 | 3.072 | 2.991 | 3.034 | 0.916 | 0.868 | 2.983 |

TABLE 21

Epitope mapping of humanized antibody PP4631. Binding to CTLA4Fc proteins was performed by ELISA, with the amounts of biotinylated protein bound measured by horse-radish peroxidase (HRP)-conjugated streptavidin. Values shown are the OD450 measurements. WT = wild type CTLA-4Fc. M1-M11 are CTLA-4Fc mutant proteins

| Protein Conc. | WT | M1 | M2 | M3 | M4 | M5 | M6 | M7 | M8 | M9 | M10 | M11 |
|---|---|---|---|---|---|---|---|---|---|---|---|---|
| 10 ng/ml | 0.312 | 2.264 | 0.207 | 0.198 | 0.194 | 0.407 | 0.22 | 0.194 | 0.247 | 0.177 | 0.181 | 0.172 |
| 10 ng/ml | 0.29 | 2.297 | 0.184 | 0.178 | 0.174 | 0.378 | 0.202 | 0.185 | 0.222 | 0.154 | 0.16 | 0.164 |
| 100 ng/ml | 1.077 | 2.827 | 0.203 | 0.27 | 0.219 | 1.371 | 0.459 | 0.281 | 0.725 | 0.171 | 0.17 | 0.172 |
| 100 ng/ml | 0.841 | 3.061 | 0.194 | 0.264 | 0.208 | 1.589 | 0.42 | 0.277 | 0.801 | 0.154 | 0.155 | 0.159 |
| 1 ug/ml | 2.51 | 2.881 | 0.339 | 0.882 | 0.473 | 2.79 | 1.992 | 1.169 | 2.33 | 0.175 | 0.17 | 0.178 |
| 1 ug/ml | 2.471 | 2.958 | 0.263 | 1.121 | 0.573 | 2.795 | 2.016 | 1.243 | 2.642 | 0.167 | 0.169 | 0.185 |

TABLE 22

Epitope mapping of humanized antibody PP4637. Binding to CTLA4Fc proteins was performed by ELISA, with the amounts of biotinylated protein bound measured by horse-radish peroxidase (HRP)-conjugated streptavidin. Values shown are the OD450 measurements. WT = wild type CTLA-4Fc. M1-M11 are CTLA-4Fc mutant proteins

| Protein Conc. | WT | M1 | M2 | M3 | M4 | M5 | M6 | M7 | M8 | M9 | M10 | M11 |
|---|---|---|---|---|---|---|---|---|---|---|---|---|
| 10 ng/ml | 0.597 | 2.307 | 0.195 | 0.544 | 0.189 | 1.239 | 0.603 | 0.19 | 0.5 | 0.373 | 0.169 | 0.157 |
| 10 ng/ml | 0.535 | 2.244 | 0.162 | 0.195 | 0.435 | 1.188 | 0.516 | 0.535 | 0.47 | 0.148 | 0.15 | 0.152 |
| 100 ng/ml | 1.947 | 2.632 | 0.182 | 0.389 | 0.248 | 2.601 | 1.296 | 0.521 | 2.001 | 0.15 | 0.15 | 0.152 |
| 100 ng/ml | 2.229 | 2.186 | 0.175 | 0.364 | 0.221 | 2.425 | 0.875 | 0.405 | 2 | 0.137 | 0.139 | 0.148 |
| 1 ug/ml | 2.724 | 2.05 | 0.259 | 1.662 | 0.725 | 2.654 | 2.355 | 1.418 | 2.548 | 0.157 | 0.151 | 0.162 |
| 1 ug/ml | 2.742 | 2.297 | 0.274 | 1.549 | 0.724 | 2.84 | 2.374 | 1.369 | 2.69 | 0.147 | 0.143 | 0.165 |

TABLE 23

Raw data from a repeat study showing specific loss of antigenic epitope only in M11. As in Table 2-5, except that additional controls were included to shown specificity of the binding.

| May 3, 2016 | Ab Conc | hCTLA4-Fc | M1 | M2 | M3 | M4 | M5 | M6 | M7 | M8 | M9 | M10 | M11 |
|---|---|---|---|---|---|---|---|---|---|---|---|---|---|
| | 0 | 0.18 | 0.187 | 0.377 | 0.183 | 0.22 | 0.177 | 0.183 | 0.186 | 0.368 | 0.15 | 0.215 | 0.171 |
| | 0 | 0.177 | 0.222 | 0.538 | 0.167 | 0.18 | 0.229 | 0.177 | 0.142 | 0.217 | 0.293 | 0.114 | 0.155 |
| | 10 ng/ml | 1.705 | 2.692 | 0.469 | 0.623 | 0.817 | 1.853 | 1.244 | 0.837 | 1.27 | 0.158 | 0.169 | 0.19 |
| | 10 ng/ml | 1.799 | 2.779 | 0.333 | 0.593 | 0.563 | 1.802 | 1.331 | 0.884 | 1.454 | 0.213 | 0.157 | 0.194 |
| Biotin-L3D10 | 100 ng/ml | 3.316 | 3.195 | 1.313 | 2.244 | 2.233 | 3.251 | 3.032 | 2.672 | 3.015 | 0.419 | 0.26 | 0.752 |
| | 100 ng/ml | 3.458 | 3.567 | 1.37 | 2.535 | 2.356 | 3.316 | 3.032 | 2.875 | 3.157 | 0.346 | 0.272 | 0.746 |
| | 1000 ng/ml | 3.567 | 3.509 | 2.833 | 3.333 | 3.08 | 3.413 | 3.282 | 3.299 | 3.352 | 1.124 | 0.945 | 2.888 |
| | 1000 ng/ml | 3.672 | 3.509 | 2.755 | 3.299 | 3.145 | 3.537 | 3.316 | 3.352 | 3.435 | 1.181 | 0.941 | 2.914 |
| | 0 | 0.195 | 0.2 | 0.202 | 0.193 | 0.192 | 0.197 | 0.195 | 0.198 | 0.192 | 0.186 | 0.185 | 0.186 |
| | 0 | 0.192 | 0.185 | 0.181 | 0.192 | 0.178 | 0.178 | 0.178 | 0.187 | 0.173 | 0.169 | 0.168 | 0.161 |
| | 10 ng/ml | 0.316 | 0.37 | 0.216 | 0.304 | 0.22 | 0.345 | 0.279 | 0.258 | 0.326 | 0.177 | 0.176 | 0.239 |
| Biotin-HB7-1 | 10 ng/ml | 0.31 | 0.356 | 0.21 | 0.414 | 0.26 | 0.331 | 0.279 | 0.253 | 0.297 | 0.159 | 0.167 | 0.236 |
| | 100 ng/ml | 1.581 | 1.882 | 0.333 | 1.245 | 0.527 | 1.813 | 1.235 | 0.899 | 1.557 | 0.176 | 0.172 | 1.092 |
| | 100 ng/ml | 1.525 | 1.928 | 0.323 | 1.345 | 0.489 | 1.735 | 1.385 | 0.987 | 1.643 | 0.162 | 0.155 | 1.283 |
| | 1000 ng/ml | 3.76 | 3.6 | 1.167 | 3.435 | 1.973 | 3.316 | 3.413 | 3.101 | 3.635 | 0.232 | 0.185 | 3.568 |
| | 1000 ng/ml | 3.6 | 3.673 | 1.316 | 3.51 | 2.009 | 3.459 | 3.413 | 3.183 | 3.635 | 0.215 | 0.181 | 3.673 |
| | 10 ng/ml | 0.451 | 2.812 | 0.207 | 0.202 | 0.194 | 0.626 | 0.23 | 0.207 | 0.327 | 0.197 | 0.205 | 0.181 |
| | 10 ng/ml | 0.417 | 2.693 | 0.181 | 0.179 | 0.177 | 0.642 | 0.22 | 0.195 | 0.32 | 0.158 | 0.182 | 0.162 |
| | 100 ng/ml | 1.868 | 3.568 | 0.212 | 0.29 | 0.256 | 2.618 | 0.589 | 0.345 | 1.532 | 0.172 | 0.174 | 0.171 |
| | 100 ng/ml | 1.938 | 3.317 | 0.203 | 0.274 | 0.247 | 2.126 | 0.571 | 0.305 | 1.419 | 0.155 | 0.155 | 0.162 |
| Biotin-HL12 | 1000 ng/ml | 2.99 | 3.568 | 0.268 | 1.181 | 0.712 | 2.922 | 2.187 | 1.329 | 2.817 | 0.181 | 0.17 | 0.177 |
| | 1000 ng/ml | 3.033 | 3.51 | 0.268 | 1.184 | 0.759 | 3.071 | 2.358 | 1.475 | 2.869 | 0.144 | 0.171 | 0.187 |
| | 10 ng/ml | 0.983 | 2.654 | 0.202 | 0.218 | 0.197 | 1.409 | 0.429 | 0.218 | 0.727 | 0.176 | 0.176 | 0.17 |
| | 10 ng/ml | 0.955 | 2.604 | 0.184 | 0.2 | 0.168 | 1.359 | 0.389 | 0.21 | 0.761 | 0.148 | 0.154 | 0.152 |
| | 100 ng/ml | 2.669 | 3.007 | 0.232 | 0.534 | 0.319 | 2.908 | 1.839 | 0.523 | 2.669 | 0.145 | 0.161 | 0.16 |
| Biotin-HL32 | 100 ng/ml | 2.741 | 3.158 | 0.203 | 0.554 | 0.374 | 2.895 | 1.741 | 0.478 | 2.604 | 0.145 | 0.148 | 0.157 |
| | 1000 ng/ml | 3.183 | 3.146 | 0.327 | 1.837 | 1.019 | 2.966 | 2.817 | 1.72 | 3.042 | 0.173 | 0.163 | 0.174 |
| | 1000 ng/ml | 3.209 | 3.316 | 0.321 | 1.867 | 1.015 | 3.196 | 2.857 | 1.766 | 3.051 | 0.143 | 0.163 | 0.187 |
| | | Biotin-L3D10 | Biotin-L3D10 | Biotin-HB7-1 | Biotin-hB7-1 | Biotin-HL12 | Biotin-HL12 | Biotin-HL32 | | | | | |
| | Ab conc | mCTLA4-Fc | hIg-Fc | mCTLA4-Fc | hIg-Fc | | | | | | | | |
| | 0 | 0.19 | 0.198 | 0.202 | 0.191 | | | | | | | | |
| | 0 | 0.189 | 0.184 | 0.18 | 0.185 | | | | | | | | |
| | 10 ng/ml | 0.201 | 0.201 | 0.338 | 0.181 | 0.179 | 0.188 | 0.185 | 0.179 | | | | |
| | 10 ng/ml | 0.18 | 0.182 | 0.318 | 0.164 | 0.165 | 0.162 | 0.17 | 0.181 | | | | |
| | 100 ng/ml | 0.303 | 0.315 | 1.635 | 0.176 | 0.171 | 0.177 | 0.185 | 0.176 | | | | |
| | 100 ng/ml | 0.314 | 0.326 | 1.668 | 0.165 | 0.162 | 0.163 | 0.165 | 0.171 | | | | |
| | 1000 ng/ml | 0.942 | 1.385 | 3.569 | 0.18 | 0.177 | 0.182 | 0.184 | 0.183 | | | | |
| | 1000 ng/ml | 0.94 | 1.475 | 3.353 | 0.179 | 0.172 | 0.177 | 0.176 | 0.187 | | | | |
| | | mCTLA4 | hIgG | mCTLA4 | hIgG | mCTLA4 | hIgG | mCTLA4 | hIgG | | | | |
| | | Biotin-L3D10 | | Biotin-hB7-1 | | Biotin HL12 | | Biotin-HL32 | | | | | |

Since L3D10 retained significant binding to M11, we tested if the binding is specific. We coated plate with human CTLA4-Fc (hCTLA4Fc), mouse CTLA4-Fc (mCTLA4-Fc), Control IgG1-Fc or all mutant hCTLA4-Fc and measured their binding to B7-1 Fc along with L3D10, PP4631 and PP4637. The bulk of the data are presented in Table 23. As shown in FIG. 57, biotinylated B7-1 binds hCTLA-4, mCTLA-4 and M11, equally well. The specificity of the assay is demonstrated by lack of binding to IgG1-Fc. Interesting, while L3D10-binding to M11 is stronger than those to IgG1-Fc and mCTLA4-Fc, significant binding to IgG1-Fc suggest that the chimeric antibody binding to M11 maybe non-specific. In contrast, none of the humanized antibodies bind to M11, mCTLA-4, and IgG1-Fc control. These data demonstrate that mutations introduced in M11 selectively ablated L3D10, PP4631 and PP4637 binding to CTLA-4.

Using known complex structure 133, we mapped the CTLA-4 epitope in a 3-D structure. As shown in FIG. 58, the epitope recognized by these mAbs localized within the area covered by B7-1. As such, L3D10, PP4631 and PP4637 binding to CTLA-4 would be mutually exclusive to that of B7-1. The poor blocking PP4631 and PP4637 is due to lower avidity rather than distinctive binding domains.

Taking advantage of the fact that the mouse and human CTLA4 proteins are cross-reactive to B7-1, but that anti-human CTLA-4 antibodies do not cross react with murine Ctla-4 protein, we were able to map the binding epitope of the L3D10 derived antibodies by ELISA. Using a number of mutants of the human CTLA-4Fc protein in which clusters of amino acids from the human CTLA-4 protein were replaced with amino acids from the murine Ctla-4 protein, we clearly demonstrate that when we replace 4 amino acids that immediately follow the known B7-1 binding domain of CTLA-4, dose-dependent binding of the antibodies is largely abolished. The fact that the binding epitope maps directly adjacent to the B7-1 binding domain correlates well with the demonstrated ability of the L3D10 antibodies to block B7-CTLA-4 interactions both in vitro and in vivo. Since soluble CTLA4 is produced by fusion of C-terminal amino acids of the extracellular IgV domain to intracellular domain, it is tempting to speculate that antibody that binds to polymorphic C-terminal domain residues (only 18 amino acid from the C-terminus) is more likely to lose reactivity to soluble CTLA-4, in which a large intracellular domain is fused to the C-terminus of the extracellular domain.

To further investigate the binding domain of the anti-CTLA4 antibodies, 6 additional mutant CTLA4-Fc fusion proteins, designated M12-M17 (SEQ ID NOS: 51-56), were designed (FIG. 59) and used to compare the binding of anti-CTLA4 antibodies 10D1 (FIG. 60A), PP4631 (FIG. 60B) and PP4637 (FIG. 60C). As shown in FIG. 60, mutations in M11, which are at positions $Y^{103}L^{104}I^{106}$, abrogated binding to 10D1, PP4631 and PP4637, demonstrating that binding sites for 10D1, PP4631 and PP4637 include residues $Y^{103}L^{104}I^{106}$. Importantly, additional mutation in A29>Y restored binding of CTLA-4 with mutations in $Y^{103}L^{104}I^{106}$ to PP4631 and PP4637. These data demonstrate that position $A^{29}$ in CTLA4 is important for the binding of antibodies PP4631 and PP4637, but not 10D1.

Example 17. Anti-CTLA-4 mAb Synergizes with Anti-4-1BB in Inducing Tumor Rejection Studies in animal models have indicated that the anti-tumor response elicited by anti-CTLA-4 monoclonal antibody (mAb) is, at least in part, due to an antigen-specific T cell response against normal "self" differentiation antigens (73, 74). The tendency of anti-CTLA-4 antibodies to exacerbate autoimmune diseases is well documented in the mouse (75-78). This notion was further corroborated and proved to be a major limitation in more recent human trials in which the patients developed severe autoimmune manifestations that required discontinuation of treatment (79). On the other hand, cancer therapeutic anti-4-1 BB mAbs have been shown to abrogate the development of autoimmune diseases in lupus prone mice (24, 25).

The fact that anti-4-1BB mAbs can both stimulate anti-tumor responses and decrease autoimmune manifestations raises the intriguing possibility that the combination of this antibody with anti-CTLA-4 mAb may result in cancer rejection without autoimmunity. In this study anti-CTLA-4 and anti-4-1BB were combined to induce rejection of large established tumors.

Combined Effect of Anti-Murine-CTLA-4 and Anti-Murine-4-1 BB Antibodies in the Induction of CD8 T Cell-Mediated Tumor Rejection Two models, one of minimal disease and one of large established tumors, were used to test the anti-tumor effect of combining anti-murine-4-1 BB and anti-murine-CTLA-4 mAb treatments. C57BL/6 mice were challenged with a subcutaneous inoculation of MC38 colon cancer cells, and at different times after tumor cell inoculation, antibodies were injected into tumor-challenged mice and the tumor size and incidence were monitored by physical examination.

In the minimal disease model, the mice were treated with hamster IgG plus rat IgG, anti-4-1BB plus hamster IgG (anti-4-1 BB alone group), anti-CTLA-4 plus rat IgG (anti-CTLA-4 alone group), or anti-4-1 BB combined with anti-CTLA-4 starting at 48 hours after inoculation of tumor cells. The antibodies were administered intraperitoneally (i.p.) on days 2, 9, and 16. Treatment with either anti-4-1 BB or anti-CTLA-4 mAb alone resulted in a delay in tumor growth with 1 out of 5 mice in each group rejecting tumors, while 4 out of 5 mice treated with both anti-CTLA-4 and anti-4-1 BB mAbs were tumor-free at the conclusion of the experiment. FIG. 61A displays the tumor growth measurements for each mouse. To compare growth rates between groups, a linear random-effects model was applied to the data. The combination therapy significantly reduced the daily growth in tumor size by 4.6 $mm^2$/day over anti-CTLA-4 alone ($p=0.0094$). Furthermore, the combination therapy significantly reduced growth by 8.4 $mm^2$/day over anti-4-1 BB alone ($p=0.0006$). In addition to the growth rate, the actual tumor sizes were compared between the treatment groups at six weeks after the initial tumor challenge. The average tumor size at six weeks was significantly smaller for mice given the combination therapy (27.5 $mm^2$) compared to mice given either anti-CTLA-4 (137.8 $mm^2$, $p=0.0251$) or anti-4-1BB separately (287.6, $p=0.0006$). Thus, in the setting of minimal tumor-burden, the combination of anti-4-1BB and anti-CTLA-4 mAbs results in significant delays in tumor growth over anti-4-1BB or anti-CTLA-4 given separately.

To determine if the anti-tumor effects of combination mAb treatment against small tumor burden could be extended to therapeutic applications against larger tumor burdens, mice with established tumors were treated with antibodies. Wild type C57BL/6 mice were challenged with a subcutaneous inoculation of MC38 colon cancer cells. Tumors were allowed to grow for 14 days, at which point, mice with established tumors (usually >7 mm in diameter) were selected and divided randomly into four treatment groups: hamster IgG plus rat IgG, anti-4-1BB plus hamster IgG, anti-CTLA-4 plus rat IgG, and anti-4-1 BB mAb combined with anti-CTLA-4 mAb. The antibodies were administered i.p. on days 14, 21, and 28 after tumor challenge. As shown in FIG. 61B, treatment with anti-CTLA-4 mAb did not impede tumor growth when compared to control IgG treatment, although rejection was seen in one of the eight mice in the group. Treatment with anti-4-1BB mAb slowed tumor growth somewhat, but only one in eight mice rejected the tumor. In contrast, combination therapy with both anti-CTLA-4 and anti-4-1BB mAbs led to the eradication of tumors in 7 out of 8 mice and prevention of further tumor growth in the remaining mouse. As above, growth rates between groups were compared by applying a linear random-effects model to the data. The combination therapy significantly reduced the daily growth in tumor size by 10.6 $mm^2$/day over anti-CTLA-4 alone ($p<0.0001$). Furthermore, the combination therapy significantly reduced growth by 6.2 $mm^2$/day over anti-4-1BB alone ($p=0.0002$). In addition to the growth rate, the actual tumor sizes were compared between the treatment groups at eight weeks after the initial tumor challenge. The estimated average tumor size at eight weeks was significantly smaller for mice given the combination therapy (−1.7 mm², 95% CI: −10.8, 7.5 mm²) compared to mice given either anti-CTLA-4 (404.9 mm², 95% CI: 285.4, 524.4 mm²; p<0.0001) or anti-4-1BB separately (228.4 mm², 95% CI: 200.4, 689.9 mm²; p=0.0004). Therefore, the combination mAb also appears to significantly delay tumor growth over anti-CTLA-4 or anti-4-1BB separately in larger tumor burdens as well.

MC38 is known to form liver metastasis.[80] To evaluate the effect of therapeutic antibodies on liver metastasis, all mice enrolled in the experiments were analyzed for liver metastasis by histology. As shown in Table 24, approximately 60% of the control Ig-treated mice had micro-metastasis in the liver. Treatments with either anti-CTLA-4 or anti-4-1BB antibodies alone reduced the rate of metastasis somewhat, although the reduction did not reach statistical significance. Remarkably, only 1/22 mice in the group treated with both antibodies had liver metastases. Using a logistic regression model, we found that the odds of liver metastasis for mice given anti-4-1BB alone were approximately 4.7 times higher than the odds for mice given both anti-4-1 BB and anti-CTLA-4 (95% CI: 1.6, 13.7; p=0.0050). Similarly, the odds of liver metastasis were 3.6 times higher for mice given anti-CTLA-4 only compared to mice given both treatments (95% CI: 1.3, 10.2; p=0.0174). Thus, combination therapy significantly reduces liver metastasis by MC38 when compared to treatment with either antibody alone.

TABLE 24

Combination therapy substantially reduces liver metastases*

| Group | Treatment | n | Number of mice with metastasis (%) | Group comparison p-value |
|---|---|---|---|---|
| G1 | Hamster IgG + Rat IgG | 19 | 11 (57.8%) | |
| G2 | Anti-CTLA-4 + Rat IgG | 18 | 6 (33.3%) | vs.G1: 0.1383 |
| G3 | Anti-4-1BB + Hamster IgG | 21 | 8 (38.1%) | vs.G1: 0.2136 |
| G4 | Anti-CTLA-4 + Anti-4-1BB | 22 | 1 (4.5%) | vs.G1: 0.0007 vs.G2: 0.0174 vs.G3: 0.0050 |

*Data are summarized from 4 independent experiments. At least two sections per liver were examined after H&E staining.

To determine which subset of immune cells was contributing to the anti-tumor effect elicited by combination mAb treatment, the major subsets of lymphocytes were depleted with monoclonal antibodies. MC38 tumor cells were injected subcutaneously. Once tumors were palpable, tumor-bearing mice were separated into four groups. Each group had a series of intraperitoneal antibody injections to deplete differing subsets of immune cells, including no depletion with normal rat IgG, CD4 T cell depletion with anti-CD4 mAb (GK 1.5), CD8 T cell depletion with anti-CD8 mAb (2.4.3), and NK cell depletion with anti-NK1.1 mAb (PK136). In addition, all mice in all groups were treated with anti-CTLA-4 plus anti-4-1BB mAbs once weekly for three weeks. Adequate depletion of immune cell subsets was evaluated by flow cytometry of peripheral blood taken from mice immediately prior to completion of the experiment (data not shown). As expected, mice with no depletion of immune cells responded to treatment with anti-CTLA-4 combined with anti-4-1BB mAb (FIG. 62). Similarly, depletion of NK cells and CD4 T cells did not affect the anti-tumor activity of combination anti-CTLA-4 plus anti-4-1BB mAb therapy. The depletion of CD8 T cells, however, abrogated the anti-tumor activity of combination antibody therapy. At day 28, the estimated average tumor size for mice with depletion of CD8 T cells (92.3 mm², 95% CI: 64.5, 120.1 mm²) was significantly higher than the average tumor sizes for mice with no depletion of immune cells (28.7 mm2, 95% CI: −17.1, 74.4 mm²), mice with depleted CD4 T cells (16.7 mm², 95% CI: 1.0, 32.4 mm²), and mice with depleted NK cells (9.3 mm², 95% CI: −8.3, 26.9 mm²). These data demonstrate that the tumor-eradicating effect of anti-CTLA-4 and anti-4-1BB mAb treatment is CD8 T cell-dependent.

Anti-4-1BB Antibody Reduced Antibody Response to Xenogeneic Anti-CTLA-4 Antibodies.

Figure 63:
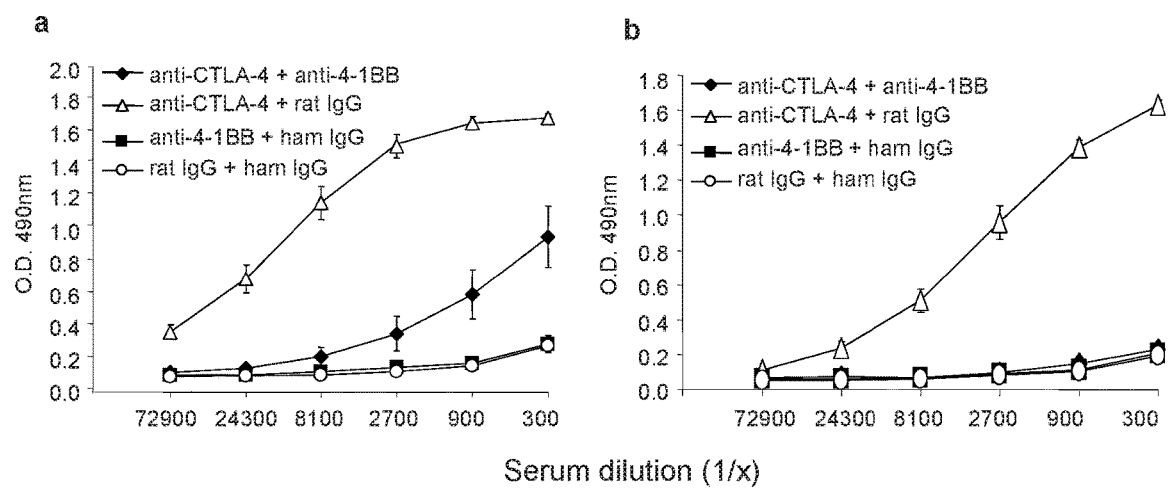

One of the obstacles to repeated antibody therapy is the enhancement of host antibody responses to the therapeutic antibodies.[81] Since 4-1BB is known to reduce antibody response to proteins, we evaluated the effect of anti-4-1BB antibodies on host response to anti-CTLA-4 antibodies. As shown in FIG. 63, very little, if any anti-antibody response was detected in mice treated with either control IgG or anti-4-1BB. Consistent with the ability of anti-CTLA-4 mAb to facilitate CD4 T cell responses[82], mice treated with anti-CTLA-4 plus rat IgG developed strong host antibody responses against the administered 4F10 antibody and rat IgG (FIGS. 63A-B). This response was reduced by more than 30-fold when anti-4-1 BB was co-administered with anti-CTLA-4 mAb. These data suggest that anti-4-1BB antibodies can potentially increase the duration of other co-administrated therapeutic proteins by reducing host responses to the therapeutics.

In Human CTLA-4 Knock-in Mice, a Combination of Anti-Mouse 4-1BB and Anti-Human CTLA-4 Antibodies Induced Tumor Rejection and Long-Lasting Cancer Immunity.

Since anti-4-1BB reduces the production of antibodies against the anti-CTLA-4 antibodies, an interesting issue is whether the enhancement of tumor rejection by anti-4-1BB is solely due to its effect in suppressing antibody response. This human CTLA4 gene knock-in mouse allowed us to test if the anti-tumor effect of the anti-human CTLA4 antibodies can be enhanced by anti-4-1BB antibody. As shown in FIG. 64A, while both anti-human CTLA-4 (L3D10) and anti-4-1BB antibody (2A) alone caused delayed tumor growth, a combination of the two antibodies resulted in the most significant tumor rejection. Respectively, in the groups treated with anti-CTLA-4, 4-1BB or the two antibodies, 1/7, 2/7, 5/7 mice never developed tumors, while all mice in the untreated group developed tumors. Since the anti-human CTLA-4 antibody is of mouse origin, the impact of 4-1BB antibody cannot be attributed to its suppression of antibodies to therapeutic anti-CTLA-4 antibodies. Moreover, our data also demonstrated that the superior effect of combination therapy will likely be applicable to anti-human CTLA-4 antibody-based immunotherapy.

To test whether the double antibody treated mice were immune to further tumor cell challenge, we challenged them with tumor cells at 110 days after their first tumor cell challenge. As shown in FIG. 64B, all of the five double antibody-treated mice that had rejected the tumor cells in the first round remained tumor-free, while control naïve mice had progressive tumor growth. Thus, combination therapy also induced long-lasting immunity to the cancer cells.

One of the obstacles to protein-based immunotherapy is host immunity to the therapeutic proteins. In the case of antibodies, the host can mount antibodies to xenotypic, allotypic and idiotypic epitopes.[81] The xenotypic response can be eliminated by complete humanization, although other anti-antibody responses require special considerations. The obstacle is more obvious for anti-CTLA-4 antibody as it is an adjuvant in itself. Previous work by Mittler et al. demonstrated a significant suppression of T-cell dependent humoral immune response.[83] Our data demonstrate that co-administration of anti-4-1BB antibodies reduces host responses to the anti-CTLA-4 antibody, which suggests another advantage of combination therapy using anti-CTLA-4 and anti-4-1BB antibody.

Taken together, our data demonstrate that combination therapy with anti-CTLA-4 and anti-4-1BB antibodies offers three major advantages, namely, an increased effect in cancer immunity, mutual suppression of autoimmune side effects, and amelioration of anti-antibody responses.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

REFERENCES CITED

1. Townsend A R M, Tothbard J, Gotch F M, Bahadur G, Wraith D, McMichael A J. The epitope of influenza nucleoprotein recognized by cytotoxic lymphocytes can be defined with short synthetic peptides. Cell. 1986; 44: 959-68.
2. Zinkernagel R M, Doherty P C. Restriction of in vitro T cell-mediated cytotoxicity in lymphocytic choriomeningitis within a syngeneic or semiallogeneic system. Nature. 1974; 248: 701-2.
3. Lafferty K J, Prowse S J, Simeonovic C J, Warren H S. Immunobiology of tissue transplantation: a return to the passenger leukocyte concept. Annu Rev Immunol. 1983; 1: 143-73.
4. Liu Y, Linsley P S. Costimulation of T-cell growth. Curr Opin Immunol. 1992; 4(3): 265-70.
5. Schwartz R H. Costimulation of T lymphocytes: the role of CD28, CTLA4, and B7/BB1 in interleukin-2 production and immunotherapy. Cell. 1992; 71(7): 1065-8.
6. Freeman G J, Freedman A S, Segil J M, Lee G, Whitman J F, Nadler L M. B7, a new member of the Ig superfamily with unique expression on activated and neoplastic B cells. J Immunol. 1989; 143(8): 2714-22.
7. Freeman G J, Gribben J G, Boussiotis V A, Ng J W, Restivo V A, Jr., Lombard L A, et al. Cloning of B7-2: a CTLA4 counter-receptor that costimulates human T cell proliferation [see comments]. Science. 1993; 262(5135): 909-11.
8. Hathcock K S, Laszlo G, Dickler H B, Bradshaw J, Linsley P, Hodes R J. Identification of an alternative CTLA4 ligand costimulatory for T cell activation [see comments]. Science. 1993; 262(5135): 905-7.
9. Wu Y, Guo Y, Liu Y. A major costimulatory molecule on antigen-presenting cells, CTLA4 ligand A, is distinct from B7. J Exp Med. 1993; 178(5): 1789-93.
10. Leach D R, Krummel M F, Allison J P. Enhancement of antitumor immunity by CTLA4 blockade [see comments]. Science. 1996; 271(5256): 1734-6.
11. Linsley P S, Brady W, Urnes M, Grosmaire L S, Damle N K, Ledbetter J A. CTLA4 is a second receptor for the B cell activation antigen B7. J Exp Med. 1991; 174(3): 561-9.
12. Linsley P S, Clark E A, Ledbetter J A. T-cell antigen CD28 mediates adhesion with B cells by interacting with activation antigen B7/BB-1. Proc Natl Acad Sci USA. 1990; 87(13): 5031-5.
13. Hodi F S, Mihm M C, Soiffer R J, Haluska F G, Butler M, Seiden M V, et al. Biologic activity of cytotoxic T lymphocyte-associated antigen 4 antibody blockade in previously vaccinated metastatic melanoma and ovarian carcinoma patients. Proc Natl Acad Sci USA. 2003; 100(8): 4712-7. PubMed PMID: 12682289.
14. Hodi F S, O'Day S J, McDermott D F, Weber R W, Sosman J A, Haanen J B, et al. Improved survival with ipilimumab in patients with metastatic melanoma. N Engl J Med. 2010; 363(8): 711-23. Epub 2010 Jun. 8. doi: 10.1056/NEJMoa1003466. PubMed PMID: 20525992; PubMed Central PMCID: PMC3549297.
15. Larkin J, Chiarion-Sileni V, Gonzalez R, Grob J J, Cowey C L, Lao C D, et al. Combined Nivolumab and Ipilimumab or Monotherapy in Untreated Melanoma. N Engl J Med. 2015; 373(1): 23-34. Epub 2015 Jun. 2. doi: 10.1056/NEJMoa1504030. PubMed PMID: 26027431.
16. Ribas A, Hodi F S, Callahan M, Konto C, Wolchok J. Hepatotoxicity with combination of vemurafenib and ipilimumab. N Engl J Med. 2013; 368(14): 1365-6. Epub 2013 Apr. 5. doi: 10.1056/NEJMc1302338. PubMed PMID: 23550685.
17. Delyon J, Mateus C, Lambert T. Hemophilia A induced by ipilimumab. N Engl J Med. 2011; 365(18): 1747-8. Epub 2011 Nov. 4. doi: 10.1056/NEJMc1110923. PubMed PMID: 22047582.
18. Fadel F, El Karoui K, Knebelmann B. Anti-CTLA4 antibody-induced lupus nephritis. N Engl J Med. 2009; 361(2): 211-2. Epub 2009 Jul. 10. doi: 10.1056/NEJMc0904283. PubMed PMID: 19587352.
19. Kocak E, Lute K, Chang X, May K F, Jr., Exten K R, Zhang H, et al. Combination therapy with anti-CTL antigen-4 and anti-4-1BB antibodies enhances cancer immunity and reduces autoimmunity. Cancer Res. 2006; 66(14): 7276-84. Epub 2006 Jul. 20. doi: 10.1158/0008-5472.CAN-05-2128. PubMed PMID: 16849577.
20. Lute K D, May K F, Lu P, Zhang H, Kocak E, Mosinger B, et al. Human CTLA4-knock-in mice unravel the quantitative link between tumor immunity and autoimmunity induced by anti-CTLA4 antibodies. Blood. 2005. PubMed PMID: 16037385.
21. May K F, Roychowdhury S, Bhatt D, Kocak E, Bai X F, Liu J Q, et al. Anti-human CTLA4 monoclonal antibody promotes T cell expansion and immunity in a hu-PBL-SCID model: a new method for preclinical screening of costimulatory monoclonal antibodies. Blood. 2005; 105: 1114-20. PubMed PMID: 15486062.
22. Shields R L, Namenuk A K, Hong K, Meng Y G, Rae J, Briggs J, et al. High resolution mapping of the binding site on human IgG1 for Fc gamma RI, Fc gamma RII, Fc gamma RIII, and FcRn and design of IgG1 variants with improved binding to the Fc gamma R. J Biol Chem. 2001; 276(9): 6591-604. Epub 2000 Nov. 30. doi: 10.1074/jbc.M009483200. PubMed PMID: 11096108.
23. Dall'Acqua W F, Woods R M, Ward E S, Palaszynski S R, Patel N K, Brewah Y A, et al. Increasing the affinity of a human IgG1 for the neonatal Fc receptor: biological consequences. J Immunol. 2002; 169(9): 5171-80. Epub 2002 Oct. 23. PubMed PMID: 12391234.

24. Gao S H, Huang K, Tu H, Adler A S. Monoclonal antibody humanness score and its applications. BMC biotechnology. 2013; 13: 55. Epub 2013 Jul. 6. doi: 10.1186/1472-6750-13-55. PubMed PMID: 23826749; PubMed Central PMCID: PMC3729710.
25. Sun Y, Chen H M, Subudhi S K, et al. Costimulatory molecule-targeted antibody therapy of a spontaneous autoimmune disease. Nat Med 2002.8: 1405-13
26. Foell J, Strahotin S, O'Neil S P, et al. CD137 costimulatory T cell receptor engagement reverses acute disease in lupus-prone NZBxNZW F1 mice. J Clin Invest 2003.111: 1505-18
27. Melero I, Shuford W W, Newby S A, et al. Monoclonal antibodies against the 4-1BB T-cell activation molecule eradicate established tumors. Nat Med 1997.3: 682-5
28. May K F, Jr., Chen L, Zheng P and Liu Y Anti-4-1BB monoclonal antibody enhances rejection of large tumor burden by promoting survival but not clonal expansion of tumor-specific CD8+ T cells. Cancer Res 2002.62: 3459-65
29. Ye Z, Hellstrom I, Hayden-Ledbetter M, et al. Gene therapy for cancer using single-chain Fv fragments specific for 4-1 BB. Nat Med 2002.8: 343-8
30. Walunas, T. L., et al., CTLA4 can function as a negative regulator of T cell activation. Immunity, 1994. 1(5): p. 405-13.
31. Krummel, M. F. and J. P. Allison, CD28 and CTLA4 have opposing effects on the response of T cells to stimulation. J Exp Med, 1995. 182(2): p. 459-65.
32. Anderson, D. E., et al., Paradoxical inhibition of T-cell function in response to CTLA4 blockade; heterogeneity within the human T-cell population. Nat Med, 2000. 6(2): p. 211-4.
33. Coyle, A. J. et al. (2001) "The Expanding B7 Superfamily: Increasing Complexity In Costimulatory Signals Regulating T Cell Function," Nature Immunol. 2(3): 203-209.
34. Sharpe, A. H. et al. (2002) "The B7-CD28 Superfamily," Nature Rev. Immunol. 2: 116-126.
35. Collins, M. et al. (2005) "The B7 Family Of Immune-Regulatory Ligands," Genome Biol. 6: 223.1-223.7.
36. Flajnik, M. F. et al. (2012) "Evolution Of The B7 Family: Co-Evolution Of B7H6 And Nkp30, Identification Of A New B7 Family Member, B7H7, And Of B7's Historical Relationship With The MHC," Immunogenetics epub doi.org/10.1007/s00251-012-0616-2.
37. Martin-Orozco, N. et al. (2007) "Inhibitory Costimulation And Anti-Tumor Immunity," Semin. Cancer Biol. 17(4): 288-298.
38. Flies, D. B. et al. (2007) "The New B7s: Playing a Pivotal Role in Tumor Immunity," J. Immunother. 30(3): 251-260
39. Ishida, Y. et al. (1992) "Induced Expression Of PD-1, A Novel Member Of The Immunoglobulin Gene Superfamily, Upon Programmed Cell Death," EMBO J. 11: 3887-3895.
40. Agata, Y. et al. (1996) "Expression Of The PD-1 Antigen On The Surface Of Stimulated Mouse T And B Lymphocytes," Int. Immunol. 8(5): 765-772.
41. Yamazaki, T. et al. (2002) "Expression Of Programmed Death 1 Ligands By Murine T Cells And APC," J. Immunol. 169: 5538-5545.
42. Nishimura, H. et al. (2000) "Facilitation Of Beta Selection And Modification Of Positive Selection In The Thymus Of PD-1-Deficient Mice," J. Exp. Med. 191: 891-898.
43. Martin-Orozco, N. et al. (2007) "Inhibitory Costimulation And Anti-Tumor Immunity," Semin. Cancer Biol. 17(4): 288-298.
44. Kabat et al., Sequences of Proteins of Immunological Interest, 5th Ed. Public Health Service, National Institutes of Health, Bethesda, Md. (1991).
45 Chothia and Lesk, 1987, J. Mol. Biol. 196: 901-917.
46. Padlan, 1991, Molecular Immunology 28(4/5): 489-498.
47. Studnicka et al., 1994, Protein Engineering 7: 805.
48. Roguska et al., 1994, Proc. Natl. Acad. Sci. USA 91: 969
49. Keler, T. et al. Activity and safety of CTLA4 blockade combined with vaccines in cynomolgus macaques. J. Immunol. 171, 6251-6259 (2003).
50. Wing, K. et al. CTLA4 control over Foxp3+ regulatory T cell function. Science 322, 271-275, doi: 10.1126/science.1160062 (2008).
51. Schwartz, R. S. The new immunology—the end of immunosuppressive drug therapy? N. Engl. J. Med. 340, 1754-1756, doi: 10.1056/NEJM199906033402209 (1999).
52. Simpson, T. R. et al. Fc-dependent depletion of tumor-infiltrating regulatory T cells co-defines the efficacy of anti-CTLA4 therapy against melanoma. J. Exp. Med. 210, 1695-1710, doi: 10.1084/jem.20130579 (2013).
53. Selby, M. J. et al. Anti-CTLA-4 antibodies of IgG2a isotype enhance antitumor activity through reduction of intratumoral regulatory T cells. Cancer immunology research 1, 32-42, doi: 10.1158/2326-6066.CIR-13-0013 (2013).
54. Maker, A. V., Attia, P. & Rosenberg, S. A. Analysis of the cellular mechanism of antitumor responses and autoimmunity in patients treated with CTLA4 blockade. J. Immunol. 175, 7746-7754 (2005).
55. Korman, A. J., Peggs, K. S. & Allison, J. P. Checkpoint blockade in cancer immunotherapy. Adv. Immunol. 90, 297-339, doi: 10.1016/S0065-2776(06)90008-X (2006).
56. Ribas, A. et al. Tremelimumab (CP-675,206), a cytotoxic T lymphocyte associated antigen 4 blocking monoclonal antibody in clinical development for patients with cancer. Oncologist 12, 873-883, doi: 10.1634/theoncologist.12-7-873 (2007).
57. Ribas, A. et al. Phase III randomized clinical trial comparing tremelimumab with standard-of-care chemotherapy in patients with advanced melanoma. J. Clin. Oncol. 31, 616-622, doi: 0.1200/JCO.2012.44.6112 (2013).
58. Lee, K. M. et al. Molecular basis of T cell inactivation by CTLA4 [In Process Citation]. Science 282, 2263-2266 (1998).
59. Marengere, L. E. et al. Regulation of T cell receptor signaling by tyrosine phosphatase SYP association with CTLA4 [published errata appear in Science 1996 Dec. 6; 274(5293)1597 and 1997 Apr. 4; 276(5309): 21]. Science 272, 1170-1173 (1996).
60. Liu, Y. Is CTLA4 a negative regulator for T-cell activation? Immunol. Today 18, 569-572 (1997).
61. Tivol, E. A. et al. Loss of CTLA4 leads to massive lymphoproliferation and fatal multiorgan tissue destruction, revealing a critical negative regulatory role of CTLA4. Immunity 3, 541-547 (1995).
62. Waterhouse, P. et al. Lymphoproliferative disorders with early lethality in mice deficient in CTLA4 [see comments]. Science 270, 985-988 (1995).
63. Bachmann, M. F., Kohler, G., Ecabert, B., Mak, T. W. & Kopf, M. Cutting edge: lymphoproliferative disease in the absence of CTLA4 is not T cell autonomous. J. Immunol. 163, 1128-1131 (1999).

64. Bachmann, M. F. et al. Normal pathogen-specific immune responses mounted by CTLA4-deficient T cells: a paradigm reconsidered. Eur. J. Immunol. 31, 450-458 (2001).
65. Nguyen, T. V., Ke, Y., Zhang, E. E. & Feng, G. S. Conditional deletion of Shp2 tyrosine phosphatase in thymocytes suppresses both pre-TCR and TCR signals. J. Immunol. 177, 5990-5996 (2006).
66. Qureshi, O. S. et al. Trans-endocytosis of CD80 and CD86: a molecular basis for the cell-extrinsic function of CTLA-4. Science 332, 600-603, doi: 10.1126/science.1202947 (2011).
67. Ueda, H. et al. Association of the T-cell regulatory gene CTLA4 with susceptibility to autoimmune disease. Nature 423, 506-511 (2003).
68. Magistrelli, G. et al. A soluble form of CTLA-4 generated by alternative splicing is expressed by nonstimulated human T cells. Eur. J. Immunol. 29, 3596-3602, doi: 10.1002/(SICI)1521-4141(199911)29:11< 3596:: AID-IMMU3596> 3.0.CO; 2-Y (1999).
69. Kremer, J. M. et al. Treatment of rheumatoid arthritis by selective inhibition of T-cell activation with fusion protein CTLA4Ig. N. Engl. J. Med. 349, 1907-1915, doi: 10.1056/NEJMoa035075 (2003).
70. Abrams, J. R. et al. CTLA4Ig-mediated blockade of T-cell costimulation in patients with psoriasis vulgaris. J. Clin. Invest. 103, 1243-1252, doi: 10.1172/JCI5857 (1999).
71. Gerold, K. D. et al. The soluble CTLA-4 splice variant protects from type 1 diabetes and potentiates regulatory T-cell function. Diabetes 60, 1955-1963, doi: 10.2337/db11-0130 (2011).
72. Peach R J, Bajorath J, Brady W, Leytze G, Greene J, Naemura J, et al. Complementarity determining region 1 (CDR1)- and CDR3-analogous regions in CTLA-4 and CD28 determine the binding to B7-1. J Exp Med 1994; 180(6): 2049-58.
73. van Elsas, A., Hurwitz, A. A. & Allison, J. P. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J. Exp. Med. 190, 355-366 (1999).
74. van Elsas, A. et al. Elucidating the autoimmune and antitumor effector mechanisms of a treatment based on cytotoxic T lymphocyte antigen-4 blockade in combination with a B16 melanoma vaccine: comparison of prophylaxis and therapy. J. Exp. Med. 194, 481-489. (2001).
75. Karandikar, N. J., Vanderlugt, C. L., Walunas, T. L., Miller, S. D. & Bluestone, J. A. CTLA-4: a negative regulator of autoimmune disease. J. Exp. Med. 184, 783-788 (1996).
76. Luhder, F., Chambers, C., Allison, J. P., Benoist, C. & Mathis, D. Pinpointing when T cell costimulatory receptor CTLA-4 must be engaged to dampen diabetogenic T cells. Proc. Natl. Acad. Sci. U.S.A. 97, 12204-12209 (2000).
77. Hurwitz, A. A., Sullivan, T. J., Sobel, R. A. & Allison, J. P. Cytotoxic T lymphocyte antigen-4 (CTLA-4) limits the expansion of encephalitogenic T cells in experimental autoimmune encephalomyelitis (EAE)-resistant BALB/c mice. Proc. Natl. Acad. Sci. U.S.A. 99, 3013-3017 (2002).
78. Piganelli, J. D., Poulin, M., Martin, T., Allison, J. P. & Haskins, K. Cytotoxic T lymphocyte antigen 4 (CD152) regulates self-reactive T cells in BALB/c but not in the autoimmune NOD mouse. J. Autoimmun. 14, 123-131 (2000).
79. Phan, G. Q. et al. Cancer regression and autoimmunity induced by cytotoxic T lymphocyte-associated antigen-4 blockade in patients with metastatic melanoma. Proc Natl Acad Sci U.S.A. 100, 8372-8377 (2003).
80. Eisenthal, A. et al. Antitumor effects of recombinant interleukin-6 expressed in eukaryotic cells. Cancer Immunol. Immunother. 36, 101-107 (1993).
81. Schroff, R. W., Foon, K. A., Beatty, S. M., Oldham, R. K. & Morgan, A. C., Jr. Human anti-murine immunoglobulin responses in patients receiving monoclonal antibody therapy. Cancer Res. 45, 879-885 (1985).
82. Kearney, E. R. et al. Antigen-dependent clonal expansion of a trace population of antigen-specific CD4+ T cells in vivo is dependent on CD28 costimulation and inhibited by CTLA-4. J. Immunol. 155, 1032-1036 (1995).
83. Mittler, R. S., Bailey, T. S., Klussman, K., Trailsmith, M. D. & Hoffmann, M. K. Anti-4-1BB monoclonal antibodies abrogate T cell-dependent humoral immune responses in vivo through the induction of helper T cell energy. J. Exp. Med. 190, 1535-1540 (1999).

The invention claimed is:

1. An anti-CTLA4 antibody comprising: (a) a light chain variable region comprising (i) a complementarity determining region (CDR) 1 comprising the amino acid sequence set forth in SEQ ID NO: 21, (ii) a CDR2 region comprising the amino acid sequence set forth in SEQ ID NO: 36, 37 or 38, and (iii) a CDR3 region comprising the amino acid sequence set forth in SEQ ID NO: 23; and, (b) a heavy chain variable region comprising (i) a CDR1 region comprising the amino acid sequence set forth in SEQ ID NO: 24, (ii) a CDR2 region comprising the amino acid sequence set forth in SEQ ID NO: 33, 34 or 35, and (iii) a CDR3 region comprising the amino acid sequence set forth in SEQ ID NO: 26.

2. The anti-CTLA4 antibody of claim 1, wherein the heavy chain variable region comprises the amino acid sequence set forth in SEQ ID NO: 62, 63 or 64; and (b) the light chain variable region comprises the amino acid sequence set forth in SEQ ID NO: 70, 71 or 72.

3. The anti-CTLA4 antibody of claim 1, wherein, (a) the light chain CDR2 region comprises the amino acid sequence set forth in SEQ ID NO: 37 and the heavy chain CDR2 region comprises the amino acid sequence set forth in SEQ ID NO: 33; (b) the light chain CDR2 region comprises the amino acid sequence set forth in SEQ ID NO: 37 and the heavy chain CDR2 region comprises the amino acid sequence set forth in SEQ ID NO: 35; or, (c) the light chain CDR2 region comprises the amino acid sequence set forth in SEQ ID NO: 38 and the heavy chain CDR2 region comprises the amino acid sequence set forth in SEQ ID NO: 35.

4. The anti-CTLA4 antibody of claim 3, wherein the heavy chain comprises the amino acid sequence set forth in SEQ ID NO: 62 and the light chain comprises the amino acid sequence set forth in SEQ ID NO: 71.

5. The anti-CTLA4 antibody of claim 3, wherein the heavy chain comprises the amino acid sequence set forth in SEQ ID NO: 64 and the light chain comprises the amino acid sequence set forth in SEQ ID NO: 71.

6. The anti-CTLA4 antibody of claim 3, wherein the heavy chain comprises the amino acid sequence set forth in SEQ ID NO: 64; and the light chain comprises the amino acid sequence set forth in SEQ ID NO: 72.

7. The anti-CTLA4 antibody of claim 1, wherein the antibody is capable of binding human CTLA4.

8. The anti-CTLA4 antibody of claim 1, wherein the antibody is characterized by reduced binding to soluble CTLA4.

9. An antigen binding fragment of the anti-CTLA4 antibody of claim 1.

10. A pharmaceutical composition comprising a therapeutically effective amount of the anti-CTLA4 antibody of claim 1 or an antigen binding fragment thereof, and a physiologically acceptable carrier or excipient.

11. A method for treating cancer in a subject in need thereof comprising administering an effective amount of the pharmaceutical composition of claim 10 to the subject.

12. The method of claim 11, further comprising administering an additional agent selected from the group consisting of anti-PD-1 and anti-4-1BB antibodies.

13. The method of claim 12, wherein the anti-PD-1 or anti-4-1BB antibodies, and the anti-CTLA4 antibody are combined in a single molecule as bi-specific antibodies.

14. The method of claim 11, wherein the pharmaceutical composition induces strong deletion of Treg and local T cell activation in tumor microenvironment but minimal systemic T cell activation.

* * * * *